(12) United States Patent
Nishitani et al.

(10) Patent No.: US 6,518,263 B1
(45) Date of Patent: Feb. 11, 2003

(54) IMIDAZO[4,5-B]PYRIDINIUMMETHYL-CONTAINING CEPHEM COMPOUNDS HAVING BROAD ANTIBACTERIAL SPECTRUM

(75) Inventors: Yasuhiro Nishitani, Osaka (JP); Hikaru Itani, Osaka (JP); Tadashi Irie, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/856,712

(22) PCT Filed: Nov. 25, 1999

(86) PCT No.: PCT/JP99/06562

§ 371 (c)(1),
(2), (4) Date: May 25, 2001

(87) PCT Pub. No.: WO00/32606

PCT Pub. Date: Jun. 8, 2000

(30) Foreign Application Priority Data

Nov. 27, 1998 (JP) .......................................... 10-336707

(51) Int. Cl.$^7$ .................... C07D 501/46; A61K 31/546; A61P 31/04
(52) U.S. Cl. ........................................ 514/203; 540/224
(58) Field of Search ........................... 514/203; 540/224

(56) References Cited

U.S. PATENT DOCUMENTS

| | | |
|---|---|---|
| 3,585,199 A | 6/1971 | Cragoe, Jr. et al. |
| 4,002,623 A | 1/1977 | Kadlin |
| 4,406,899 A | 9/1983 | Aburaki et al. |
| 4,525,473 A | 6/1985 | Aburaki et al. |
| 4,547,573 A | 10/1985 | Jung et al. |
| 4,590,186 A | 5/1986 | Takaya et al. |
| 4,609,653 A | 9/1986 | Dürckheimer et al. |
| 4,748,171 A | 5/1988 | Yamauchi et al. |
| 4,804,658 A | 2/1989 | Manley et al. |
| 4,864,022 A | 9/1989 | Miyake et al. |
| 5,281,589 A | 1/1994 | Kim et al. |
| 5,332,744 A | 7/1994 | Chakravarty et al. |
| 5,334,598 A | 8/1994 | Bagley et al. |
| 5,382,586 A | 1/1995 | Merce-Vidal et al. |
| 5,389,634 A | 2/1995 | Fortin et al. |
| 5,486,525 A | 1/1996 | Summers, Jr. et al. |
| 5,506,238 A | 4/1996 | Miyake et al. |
| 5,635,485 A | 6/1997 | Agouridas et al. |
| 5,635,514 A | 6/1997 | Khanna et al. |
| 5,719,306 A | 2/1998 | Chandrakumar et al. |
| 5,739,147 A | 4/1998 | Hemmerle et al. |
| 5,846,990 A | 12/1998 | Murugesan et al. |
| 6,100,404 A * | 8/2000 | Agouridas et al. .......... 544/264 |

FOREIGN PATENT DOCUMENTS

| | | |
|---|---|---|
| EP | 0 042 154 | 12/1981 |
| EP | 0 062 321 | 10/1982 |
| EP | 0 074 268 | 3/1983 |
| EP | 0 137 440 | 4/1985 |
| EP | 0 137 441 | 4/1985 |
| EP | 0 138 552 | 4/1985 |
| EP | 0 160 252 | 11/1985 |
| EP | 0 203 271 | 12/1986 |
| EP | 0 434 038 A1 | 6/1991 |
| EP | 0 934 941 A1 | 8/1999 |
| JP | 60-120889 | 6/1985 |
| JP | 2-48587 | 2/1990 |
| JP | 5-201991 | 8/1993 |
| JP | 5-222058 | 8/1993 |
| JP | 5-331149 | 12/1993 |
| JP | 6-41149 | 2/1994 |
| JP | 6-157542 | 6/1994 |
| JP | 7-101958 | 4/1995 |
| JP | 7-101960 | 4/1995 |
| JP | 9-165371 | 6/1997 |
| WO | WO 91/13070 | 9/1991 |
| WO | WO 92/06086 | 4/1992 |
| WO | WO 94/22859 | 10/1994 |
| WO | WO 97/41128 | 11/1997 |

OTHER PUBLICATIONS

Oak K. Kim et al.: "Synthesis and Structure–Activity Relationship of C–3 Quaternary Ammonium Cephalosporins Exhibiting Anti–MRSA Activities," Biorganic & Medicinal Chemistry Letters, 1997, pp. 2753–2758, vol. 7, No. 21, Elsevier Science Ltd., Pergamon.

\* cited by examiner

Primary Examiner—Mark L. Berch
(74) Attorney, Agent, or Firm—Foley & Lardner

(57) ABSTRACT

A cefem compound of the formula (I) shows wide antibacterial spectrum against various pathogenic bacteria including MRSA.

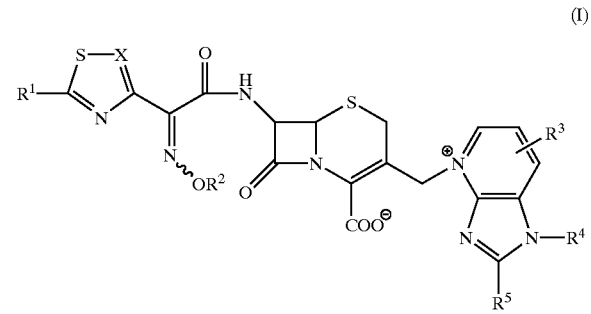

(I)

wherein, X is N or CY and Y is H or halogen; $R^1$ is amino or protected amino; $R^2$ is hydrogen or optionally substituted lower alkyl etc.; $R^3$ is hydrogen etc.; $R^4$ is hydrogen, optionally substituted lower alkyl, or optionally substituted N-containing heterocyclic group etc.; $R^5$ is hydrogen etc.; and a wavy line means syn- or anti-isomerism or a mixture thereof.

9 Claims, No Drawings

IMIDAZO[4,5-B]PYRIDINIUMMETHYL-CONTAINING CEPHEM COMPOUNDS HAVING BROAD ANTIBACTERIAL SPECTRUM

TECHNICAL FIELD

The present invention relates to cephem compounds having a broad antibacterial spectrum over various pathogenic bacteria and to pharmaceutical compositions containing the same. The compounds of the present invention are particularly efficacious against MRSA (methicillin resistant S. aureus).

BACKGROUND ART

Study of so-called broad spectrum cephem compounds having potent antibacterial activities against various Gram-positive and Gram-negative bacteria has recently been focused on cephem compounds at which 7-side chain is substituted with aminothiazole or aminothiadiazole and 3-position with a cyclic-type quarternary ammoniummethyl group. For example, the known 7-aminothiazole types include cefepime hydrochloride (U.S. Pat. No. 4,406,899), cefpirome sulfate (U.S. Pat. No. 4,609,653, JP(A) S57-192394), and cefoselis sulfate (JP(A) H07-196665, WO97/41128), and the 7-aminothiadiazole types include cefclidin (U.S. Pat. No. 4,748,171), and cefozopran hydrochloride (U.S. Pat. No. 4,864,022, JP(A) S62-149682, JP(A) H03-47189). These cephem compounds show almost none or extremely weak activities against MRSA which has been a clinical concern.

The other documents, disclosing the same types of cephem compounds, include, for example, JP(A) 4789/1983, JP(A) 155183/1985, JP(A) 97982/1985, JP(A) 97983/1985, JP(A) 24389/1982, JP(A) 57390/1983, JP(B) 65350/1991, JP(B) 14117/1992, JP(A) 231684/1985, JP(A) 30786/1987, WO92/22556, JP(A) 222058/1993, JP(A) 157542/1994, JP(A) 101958/1995, and JP(A) 101960/1995.

Among them, JP(A) 4789/1983 discloses cephem compounds which have an optionally substituted and 2 or more N atoms-containing heterocycle cation at the 3-position. JP(A) 155183/1985 discloses cephem compounds which have a 2 or more N atoms-containing and unsaturated condensed heterocycle cation at the 3-position. These documents, however, describe or suggest no concrete embodiment of a cephem compound having an imidazopyridiniummethyl group at the 3-position.

Though JP(A) 105685/1985, equivalent to J. Med. Chem. 1990, 33, P2114–2121, discloses cephem compounds having an imidazopyridiniummethyl group at the 3-position, any of the 3-substituents of the working example compounds is limited to imidazo[4,5-c]pyridiniummethyl. On the other hand, a compound having an imidazo[4,5-b] pyridiniummethyl group at the 3-position is shown by the chemical name without any physical data or the like. Further, the [4,5-b]-type compounds have only aminothiazole group as part of the 7-side chain. Namely, the document does not concretely describe a cephem compound at which 3-position is substituted with an imidazo[4,5-b] pyridiniummethyl group and 7-side chain with aminothiadiazole.

Therefore, it has been desired to develop cephem compounds of broad antibacterial spectrum which have anti-MRSA activity applicable enough to clinical use.

DISCLOSURE OF INVENTION

The present inventors have intensively studied to find out that introduction of an imidazo[4,5-b]pyridiniummethyl group into the 3-position of cephem compounds leads to broad antibacterial spectrum and excellent anti-MRSA activity, and have accomplished the present invention shown below.

(1) a compound of the formula (I):

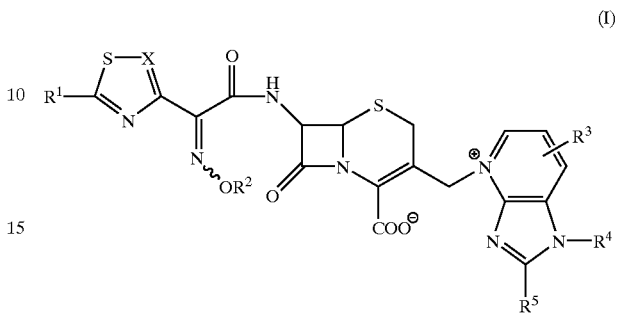

wherein,

X is N or CY and Y is H or halogen;

$R^1$ is amino or protected amino;

$R^2$ is hydrogen, optionally substituted lower alkyl or optionally substituted cycloalkyl;

$R^3$ is hydrogen, hydroxy, halogen, optionally substituted lower alkyl, optionally substituted lower alkoxy, optionally substituted lower alkylthio or optionally substituted amino;

$R^4$ is hydrogen, hydroxy, optionally substituted lower alkyl, optionally substituted lower alkenyl, optionally substituted lower alkoxy, optionally substituted cycloalkyl, optionally substituted cycloalkyl(lower) alkyl or an optionally substituted N-containing heterocyclic group;

$R^5$ is hydrogen, amino, optionally substituted lower alkyl, optionally substituted lower alkoxy or optionally substituted lower alkylthio, or $R^4$ and $R^5$ taken together may form lower alkylene in which an optional hetero atom(s) intervene; and a wavy line means syn- or anti-isomerism or a mixture thereof, an ester, a pharmaceutically acceptable salt, a prodrug, or a solvate thereof (herein after may be referred to as compound (I)).

(2) the compound described in above (1) wherein X is N.

(3) the compound described in above (1) wherein $R^1$ is amino.

(4) the compound described in above (1) wherein $R^2$ is hydrogen or optionally substituted lower alkyl.

(5) the compound described in above (4) wherein $R^2$ is lower alkyl optionally substituted with halogen.

(6) the compound described in above (1) wherein $R^3$ is hydrogen.

(7) the compound described in above (1) wherein $R^4$ is hydrogen, optionally substituted lower alkyl or an optionally substituted N-containing heterocyclic group.

(8) the compound described in above (7) wherein $R^4$ is hydrogen, lower alkyl optionally substituted with amino, lower alkylamino or hydroxy(lower) alkylamino, or an optionally substituted 4- to 6-membered N-containing saturated heterocyclic group.

(9) the compound described in above (1) wherein $R^5$ is hydrogen.

(10) the compound described in above (1) wherein the wavy line means syn-isomerism.

(11) the compound described in above (1) wherein X is N; $R^1$ is amino; $R^2$ is hydrogen or optionally substituted lower alkyl; R³ is hydrogen; R⁴ is hydrogen, optionally substituted lower alkyl or an optionally substituted N-containing heterocyclic group; R⁵ is hydrogen; and the wavy line means syn-isomerism.

(12) the compound described in above (11) wherein X is N; R¹ is amino; R² is hydrogen or lower alkyl optionally substituted with halogen; R³ is hydrogen; R⁴ is hydrogen, lower alkyl optionally substituted with amino, lower alkylamino or hydroxy(lower)alkylamino, or an optionally substituted 4- to 6-membered N-containing saturated heterocyclic group; R⁵ is hydrogen; and the wavy line means syn-isomerism.

(13) the compound described in above (12) wherein X is N; R¹ is amino; R² is hydrogen, —CH₃, —CH₂F, —CH₂CH₃ or —CH₂CH₂F; R³ is hydrogen; R⁴ is hydrogen, —CH₃, —CH₂CH₃, —(CH₂)₂CH₃, —(CH₂)₃NH₂, —(CH₂)₃NHCH₃, —(CH₂)₃NH(CH₂)₂OH, azetidinyl, pyrrolidinyl or piperidyl; R⁵ is hydrogen; and the wavy line means syn-isomerism.

(14) the compound described in above (13) wherein X is N; R¹ is amino; R² is hydrogen, —CH₂F or —CH₂CH₃; R³ is hydrogen; R⁴ is hydrogen, —(CH₂)₃NH₂, —(CH₂)₃NHCH₃ or —(CH₂)₃NH(CH₂)₂OH; R⁵ is hydrogen; and the wavy line means syn-isomerism.

(15) the compound described in above (14), a pharmaceutically acceptable salt or hydrate thereof wherein X is N; R⁵ is amino; R² is —CH₂F; R³ is hydrogen; R⁴ is —(CH₂)₃NHCH₃; R⁵ is hydrogen; and the wavy line means syn-isomerism.

(16) the compound described in above (15) which is a sulfate or a hydrate thereof.

(17) the compound described in any of above (1) to (16), which shows an antibacterial activity against Gram-positive bacteria including MRSA and Gram-negative bacteria.

(18) the compound described in (17) of which MIC₅₀ value against MRSA is 50 μg/ml or less.

(19) A method for preparing the compound described in any of above (1) to (18), which comprises reacting a compound of the formula(V):

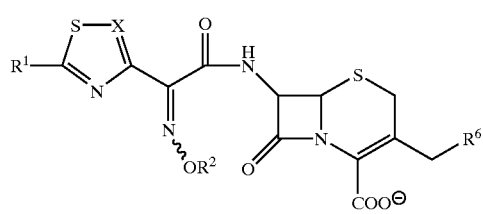

wherein R⁶ is a leaving group and the other symbols are the same as defined above, an ester, or a salt thereof with a compound of the formula(IV):

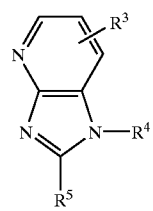

wherein each symbol is the same as defined above, followed by optional deprotection.

(20) a compound of the formula(IV):

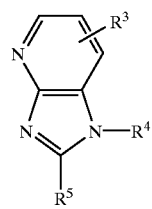

wherein each symbol is the same as defined above.

(21) the compound described in above (20) wherein R³ is hydrogen; R⁴ is —(CH₂)₃NRᵃCH₃ wherein Rᵃ is H or an amino-protecting group; and R⁵ is hydrogen,

(22) a pharmaceutical composition which contains a compound described in any of above (1) to (18).

(23) a composition for use as an antibacterial agent which contains a compound described in any of above (1) to (18).

(24) a method for preventing or treating bacterial infectious diseases, which comprises administering a compound described in any of above (1) to (18).

(25) use of the compound described in any of above (1) to (18) for preparing a composition for use as an antibacterial agent.

BEST MODE FOR CARRYING OUT THE INVENTION

Terms used herein are explained below. Unless otherwise mentioned, each term, by itself or as part of another, has a common meaning.

(Definition of X)

X is preferably N or CH, and more preferably N. Examples of halogen shown by Y include F, Cl, and Br and preferred is Cl.

(Definition of R¹)

The protecting group of protected amino may be that known in the present field, such as C1~C6 alkanoyl (e.g., formyl, acetyl, propionyl, butyryl, valeryl, pivaroyl, and succinyl), C3~C5 alkenoyl (e.g., acryloyl, crotnoyl, and cinnamoyl), C6~C10 arylcarbonyl (e.g., benzoyl, naphthoyl, p-toluoyl, and p-hydroxybenzoyl), heterocyclylcarbonyl group (example of the heterocyclyl: e.g., 2-pyrrolyl, 3-pyrazolyl, 4-imidazolyl, 1,2,3-triazolyl, 1H-tetrazolyl, 2-furyl, 3-thienyl, 4-oxazolyl, 3-isooxazolyl, 2-pyrrolidinyl, 3-pyridyl, and 4-pyridazinyl), C1~C6 alkylsulfonyl (e.g., methanesulfonyl and ethanesulfonyl), C6~C10 arylsulfonyl (e.g., benzenesulfonyl, naphthalenesulfonyl, and p-toluenesulfonyl), substituted oxycarbonyl (e.g., methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, benzyloxycarbonyl, p-methylbenzyloxycarbonyl, p-methoxybenzyloxycarbonyl, p-chlorobenzyloxycarbonyl, p-nitrobenzyloxycarbonyl, t-butoxycarbonyl (Boc), and 2-propenyloxycarbonyl), substituted silyl (e.g., trimethylsilyl and tert-butyldimethylsilyl), and optionally substituted aralkyl (e.g., p-methoxybenzyl (PMB) and benzhydryl (BH)). One or two of the protecting group, preferably one, may bond to an amino group. A preferred R¹ is amino in the light of the antibacterial activity.

(Definition of R²)

Lower alkyl includes a straight or branched C1 to C6 alkyl such as methyl, ethyl, n-propyl, i-propyl, t-butyl, n-pentyl, and n-hexyl, and preferred is C1 to C3 alkyl, more preferred is methyl, ethyl or n-propyl.

Cycloalkyl includes C3 to C7 cycloalkyl such as cyclopropyl, cyclobutyl, cyclopentyl, cyclohexyl, and cycloheptyl.

When the above lower alkyl or cycloalkyl is substituted, examples of the substituent include halogen (e.g., F, Cl, and Br), hydroxy, carboxy, cyano, amino, carbamoyloxy, sulfamoyl, lower alkoxycarbonyl (e.g., methoxycarbonyl, and ethoxycarbonyl), lower alkylthio (e.g., methylthio, and ethylthio), and preferred is halogen, esp., F. The number of the substituent is one or more.

Preferable $R^2$ includes hydrogen and optionally substituted lower alkyl (e.g., $CH_3$, $CH_2F$, $CH_2CH_3$, and $CH_2CH_2F$), and more preferred is lower alkyl substituted with halogen (e.g., $CH_2F$). The wavy line of "—OR2" preferably means syn-isomerism for the 7-amido bond part.
(Definition of $R^3$)

Examples of halogen include F, Cl, Br and I.

Examples of lower alkyl include the above lower alkyl defined for $R^2$, and preferred is methyl.

Examples of lower alkoxy include oxy bonding to lower alkyl, such as methoxy, ethoxy, n-propoxy, i-propoxy, t-butoxy, n-pentyloxy, and n-hexyloxy.

Examples of lower alkylthio include thio bonding to the lower alkyl, such as methylthio, ethylthio, n-propoxy, i-propylthio, t-butylthio, n-pentylthio, and n-hexylthio.

When the above lower alkyl, lower alkoxy or lower alkylthio is substituted, examples of the substituent include halogen (e.g., F, Cl, and Br), hydroxy, carboxy, cyano, amino, carbamoyloxy, sulfamoyl, lower alkoxycarbonyl (e.g., methoxycarbonyl and ethoxycarbonyl), and lower alkylthio (e.g., methylthio and ethylthio).

Examples of the substituent of "optionally substituted amino" include the above-described lower alkyl (e.g., methyl and ethyl) and the above-described amino-protecting group, and one or two of the substituents may be located on the amino.

$R_3$ may be located at any of the 2- to 4-positions of the pyridinium ring. $R_3$ is preferably hydrogen.
(Definition of $R^4$)

Lower alkyl and cycloalkyl are the same as the above-described lower alkyl and cycloalkyl, respectively, which are defined for $R^2$. Cycloalkyl(lower)alkyl means lower alkyl bonding to the cycloalkyl, such as cyclopropylmethyl, 1-cyclopropylethyl, 3-cyclopropylpropyl, cyclobutylmethyl, cyclopentylethyl and 3-cyclohexylpropyl.

Examples of lower alkenyl include a straight or branched C2 to C6 alkenyl, such as vinyl, aryl, 1-propenyl, i-propenyl, 1-butenyl, 2-butenyl, 3-butenyl, 2-methyl1-propenyl, 2-methyl2-propenyl, 1-pentenyl, and 2-hexenyl, and preferred is aryl.

Lower alkoxy is the same as the above-described lower alkoxy defined for $R^3$.

When each of the above lower alkyl, lower alkenyl, lower alkoxy, cycloalkyl and cycloalkyl(lower)alkyl is substituted, examples of the substituent include one or more, same or different, group(s) selected from hydroxy, optionally substituted carbamoyl (wherein the substituent is methyl, ethyl, propyl or —$(CH_2)_3CH(NH_2)CONH_2$), halogen (e.g., F and Cl), —$CO(CH_2)nCH(NH_2)CONH_2$(n=1 to 3), optionally substituted amino wherein the substituent is lower alkyl (e.g., methyl, ethyl, and propyl), lower alkenyl (e.g., aryl), cycloalkyl (e.g., cyclopropyl), lower alkoxycarbonyl (e.g., t-butoxycarbonyl), hydroxy(lower)alkyl (e.g., hydroxymethyl, 1-hydroxyethyl, and 2-hydroxyethyl), sulfonic acid-oxy(lower)alkyl (e.g., 2-sulfonic acid-oxyethyl) or amino(lower)alkyl (e.g., 2-aminoethyl)), lower alkoxy (e.g., methoxy, ethoxy, and propoxy), lower alkoxycarbonyl (e.g., methoxycarbonyl and ethoxycarbonyl), and N-containing heterocyclic group which is mentioned below wherein preferable is azetidinyl, pyrrolidinyl, piperidinyl, pyridyl or the like.

The N-containing heterocyclic group means an aromatic or non-aromatic heterocyclic group which contains at least one or more N atom(s) and optional O or S atom(s), such as azetidinyl, pyrrolidinyl, piperidinyl, imidazolydinyl, pyrazolidinyl, piperazinyl, thiazolidinyl, oxazolidinyl, morpholinyl, thio morpholinyl, thiazolinyl, oxazolinyl, imidazolinyl, pyrrolyl, pyrazolyl, imidazolyl, oxazolyl, isooxazolyl, thiazolyl, pyridyl, pyridazinyl, pyrimidinyl, pyrazinyl, triazinyl, imidazolyl, triazolyl, and tetrazolyl. Preferred is a non-aromatic group, esp., a 4- to 6-membered N-containing saturated heterocyclic group such as azetidinyl (e.g., 3-azetidinyl), pyrrolidinyl (e.g., 3-pyrrolidinyl), and piperidinyl (e.g., 4-piperidinyl).

When the heterocyclic group is substituted, examples of the substituent include one or more of the same or different group(s) selected from halogen (e.g., F and Cl), hydroxy, hydroxy(lower)alkyl (e.g., hydroxymethyl, 1-hydroxyethyl, and 2-hydroxyethyl), optionally substituted amino (wherein the substituent is lower alkyl (e.g., methyl, ethyl, and propyl) or the like), optionally substituted carbamoyl (wherein the substituent is e.g., methyl and ethyl), lower alkyl (e.g., methyl and ethyl), lower alkoxy (e.g., methoxy, ethoxy, and propoxy), imino(lower) alkyl (e.g., iminomethyl and 1-imonoethyl), halogenated(lower)alkyl (e.g., trifluoromethyl), optionally esterfied carboxy, cyano, nitro, lower alkylthio (e.g., methylthio), lower alkoxyalkoxy (e.g., methoxymethoxy and ethoxyethoxy), lower alkoxycarbonyl (e.g., methoxycarbonyl and ethoxycarbonyl), acylamino (e.g., acetylamino) and the like. In addition to those, the possible substituents on the N atom of the heterocyclic group include the above-described amino-protecting group.

$R^4$ is preferably one, two or more of the same or different group(s) selected from hydrogen, optionally substituted (lower)alkyl (wherein the substituent is preferably optionally substituted amino (wherein the substituent is lower alkyl (e.g., methyl), hydroxy(lower)alkyl (e.g., 2-hydroxyethyl), sulfonic acid-oxy(lower)alkyl (e.g., 2-sulfonic acid-oxyethyl) or the like), lower alkoxycarbonyl (e.g., t-butoxycarbonyl), carbamoyl, lower alkylcarbamoyl(e.g., methylcarbamoyl), hydroxy, halogen, lower alkoxy (e.g., methoxy), the above-described amino-protecting group (e.g., Boc, PMB) or the like), N-containing heterocyclic group and the like, more preferably hydrogen, —$CH_3$, —$CH_2CH_3$, —$(CH_2)_2CH_3$, —$(CH_2)_3NH_2$, —$(CH_2)_3NHCH_3$, —$(CH_2)_3NH(CH_2)_2OH$, azethidinyl, pyrrolidinyl or piperidinyl, and most preferably hydrogen, —$(CH_2)_3NH_2$, —$(CH_2)_3NHCH_3$ or —$(CH_2)_3NH(CH_2)_2OH$.
(Definition of $R^5$)

The lower alkyl, by itself or as part of lower alkylthio, is the same as that defined for $R^2$. The lower alkoxy is the same as that defined for $R^3$.

Examples of the substituent on the lower alkyl, lower alkoxy or lower alkylthio include halogen (e.g., F, Cl, and Br), hydroxy, carboxy, cyano, amino, carbamoyloxy, sulfamoyl, lower alkoxycarbonyl (e.g., methoxycarbonyl and ethoxycarbonyl), lower alkylthio(e.g., methylthio and ethylthio) and the like.

$R^5$ is preferably hydrogen, methyl, methylthio or the like, and more preferably hydrogen.

$R^4$ and $R^5$ taken together may form lower alkylene in which an optional hetero atom(s) intervene. When the hetero atom is N, it may be substituted with lower alkyl or the like, resulting in that $R^4$ and $R^5$ taken together forms —$(CH_2)_3$—N(Me)— for example.

The esters of compound (I) include an ester which is formed at the 4-carboxy part, e.g., an ester useful as an intermediate or a metabolic ester. Examples of the ester-residue include e.g., optionally substituted C1–C6 alkyl, C2–C6 alkenyl, C3–C10 cycloalkyl, C3–C10 cycloalkyl (C1–C6)alkyl, optionally substituted C6–C10 aryl, optionally substituted C7–C12 aralkyl, di(C6–C10)arylmethyl, tri(C6–C10)arylmethyl, and substituted silyl.

Examples of the optionally substituted C1–6 alkyl include e.g., methyl, ethyl, n-propyl, n-butyl, t-butyl, n-pentyl, and n-hexyl, each may be substituted with benzyloxy, C1–4 alkylsulfonyl (e.g., methanesulfonyl), trimethylsilyl, halogen (e.g., F, Cl, and Br), acetyl, nitrobenzoyl, mesylbenzoyl, phthalimide, succinoylimide, benzenesulfonyl,phenylthio, di-C1–4alkylamino (e.g., dimethylamino), pyridyl, C1–4alkylsulfinyl (e.g., methanesulfinyl), cyano and the like. Such substituted C1–6 alkyl include e.g., benzyloxymethyl, 2-methanesulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidemethyl, succinoylimidemethyl, benzenesulfonylmethyl, phenylthiomethyl, and 1-dimethylaminoethyl. The above C2–6 alkenyl includes e.g., vinyl, aryl, 1-propenyl, isopropenyl, 1-butenyl, 2-butenyl, 1,1-dimethylaryl, 3-methyl and 3-butenyl. The above C3–10 cycloalkyl includes e.g., cyclopropyl, cyclobutyl, cyclopentyl, cyclohexyl, cycloheptyl, norbornyl, and adamantyl. The above C3–10 cycloalkyl(C1–6)alkyl includes e.g., cyclopropylmethyl, cyclopentylmethyl, and cyclohexylmethyl. The above C6–10 aryl includes e.g., phenyl, α-naphthyl, 8-naphthyl, and biphenyl, each may be substituted with nitro, halogen (e.g., F, Cl, and Br) or the like, and such substituted aryl includes e.g., p-nitrophenyl and p-chlorophenyl. The above optionally substituted C7–12 aralkyl includes e.g., benzyl, 1-phenylethyl, 2-phenylethyl, phenylpropyl and naphthylmethyl, each may be substituted with nitro, C1–4 alkoxy (e.g., methoxy), C1–4 alkyl (e.g., methyl, ethyl), hydroxy or the like. Such substituted group is exemplified by p-nitrobenzyl, p-methoxybenzyl (PMB), or 3,5-di-t-butyl-4-hydroxybenzyl. The above di(C6–10 aryl)methyl includes benzhydryl and the C6–10 arylmethyl includes trityl, and the substituted silyl includes trimethylsilyl and tert-butyldimethylsilyl, for example.

Examples of the pharmaceutically acceptable salt of compound (I) include salts formed with inorganic bases, ammonia, organic bases, inorganic acids, organic acids, basic amino acids, halogen ions or the like, and inner salts. Examples of the inorganic base include alkali metal (e.g., Na and K) and alkaline earth metal (e.g., Mg). Examples of the organic base include procaine, 2-phenylethylbenzylamine, dibenzylethylenediamine, etanolamine, di etanolamine, tris (hydroxymethyl)aminomethane, polyhydroxyalkylamine, and N-methyl glucosamine. Examples of the inorganic acid include hydrochloric acid, hydrobromic acid, sulfuric acid, nitric acid, and phosphoric acid. Examples of the organic acid include p-toluene sulfonic acid, methanesulfonic acid, formic acid, trifluoroacetc acid and maleic acid. Examples of the basic amino acid include lysine, arginine, ornithine and histidine. The quarternary ammonium cation on the 3-side chain of compound (I) may form an inner salt with the 4-COO group as a counter ion. When the group at the 4-position is COOH or COOR wherein R is a metal cation or ester-residue, the quarternary ammonium cation is combined with a counter ion. Compound (I) is preferably an inorganic salt, more preferably a salt of sulfuric acid, and most preferably mono sulfate in the light of the crystallinity, conservation stability, handling in pharmaceutical manufacturing or the like.

Prodrug means a derivative of compound(I), which has a chemically or metabolically decomposable group and is converted to a pharmaceutically active compound (I) by solvolysis or under physiological conditions in vivo. A method for selecting and preparing an appropriate prodrug-derivative is described in e.g., Design of Prodrugs, Elsevier, Amsterdam 1985.

When compound (I) has a carboxy group, examples of the prodrug include an ester derivative prepared by reacting an acidic original compound with a proper alcohol or an amide derivative prepared by reacting an acidic original compound with a proper amine. Preferred esters as the prodrug include methyl ester, ethyl ester, n-propyl ester, isopropyl ester, n-butyl ester, isobutyl ester, tert-butyl ester, and morpholinoethylester. When compound (I) has a hydroxyl group, examples of the prodrug include an acyloxy derivative which is prepared by reacting a hydroxyl group-containing compound with a proper acyl halide or acid anhydride. Preferred acyloxy includes —$OCOC_2H_5$, —OCO(t-Bu), —$OCOC_{15}H_{31}$, —OCO(m-COONa-Ph), —$OCOCH_2CH_2COONa$, —$OCOCH(NH_2)CH_3$ and —$OCOCH_2N(CH_3)_2$. When compound (I) has an amino group, examples of the prodrug include an amide derivative which is prepared by reacting an amino group-containing compound with a proper halogenated acid or mixed acid anhydride. Preferred amides include —$NHCO(CH_2)_{20}CH_3$, —$NHCOCH(NH_2)CH_3$ and the like.

The solvate of compound (I) is preferably hydrate e.g., 0.5- to 10-hydrate, and more preferably 4-, 5-, 6-, 7-, or 8-hydrate. Particularly preferred is a crystalline monosufate·4- to 8-hydrate. Compound (I) may be a solvate formed with i-propanol, ethanol, trifluoroacetic acid or the like.

Compound (I) is preferably a compound described in any of above (11) to (18), more preferably a compound (I) wherein X is N; $R^1$ is amino; $R^2$ is —$CH_2F$; $R^3$ is hydrogen; $R^4$ is —$(CH_2)_3NHCH_3$; $R^5$ is hydrogen; and the wavy line means syn-isomerism or a salt thereof, esp. mono sulfate, for example. Among the sulfate, crystals are preferred to non-crystals in the light of their stability for pharmaceutical preparation or the like, and more preferred are crystalline hydrates such as 4- to 7- or 8-hydrate of monosulfate, esp. the 4- or 5-hydrate. These crystals are characterized by specific main peaks of the powder X-ray diffractometry.

Methods for preparing compound (I) are shown below.
(Method 1)
Compound (I) can be synthesized by reacting a 7-amino compound of the formula (II):

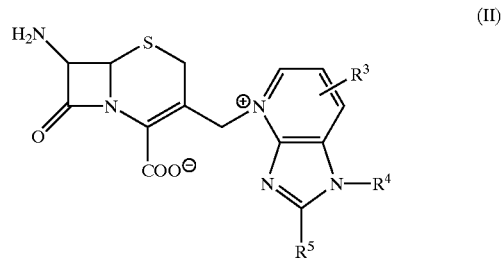

wherein each symbol is the same as defined above, a ester or salt thereof (each hereinafter referred to as compound (II)) with a carboxylic acid of the formula(III):

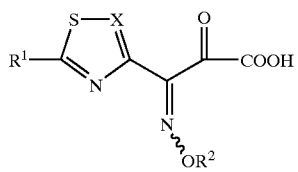
(III)

wherein each symbol is the same as defined above, or a reactive derivative thereof (each hereinafter referred to as compound (III)).

Examples of the ester or salt of compound (II) include the same as those mentioned for compound (I).

Examples of the reactive derivative of compound (III) include inorganic base salts, organic base salts, acid halides, acid azides, acid anhydrides, mixed acid anhydride, active amide, active ester, active thioester. The inorganic base includes alkaline metals (e.g., Na and K) and alkaline earth metals (e.g., Ca and Mg); The organic base includes trimethylamine, triethylamine, tert-butyldimethylamine, dibenzylmethylamine and benzyldimethylamine; the acid halide includes acid chloride and acid bromide; the mixed acid anhydride includes mixed monoalkylcarboxylic acid anhydride, mixed alphatic carboxylic acid anhydride, aromatic carboxylic acid anhydride, oraganic sulfonic acid anhydride, the active amide includes amide formed with heterocyclic compound containing N atom, for example. Examples of the active ester include organic phosphate esters (e.g., diethoxy phosphate ester and diphenoxy phosphate ester), p-nitrophenyl ester, 2,4-dinitrophenyl ester, cyanomethyl ester, and the active thioester includes esters formed with aromatic heterocyclicthio compound (e.g., 2-pyridilthio ester).

The above reaction may be carried out using an appropriate condensing agent, if necessary. Examples of the condensing agent include e.g., N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloropyridiniummethyl iodine, and 2-fluoropyridiniummethyl iodine.

Examples of solvents used in the reaction include ethers (e.g., dioxane, THF, diethylether, tert-butylmethylether, and diisopropylether), esters (e.g., ethyl formate, ethyl acetate, and n-butyl acetate), halogenated hydrocarbons (e.g., dichloromethane, chloroform, and carbon tetrachloride), hydrocarbons (e.g., n-hexane, benzene, and toluene), amides (e.g., formamide, N,N-dimethylformamide (DMF), N,N-dimethylacetoamide, and N-methylpyrrolidone), ketones (e.g., acetone and methylethylketone), nitryls (e.g., MeCN and propionitryl), dimethylsulfoxide, and water.

The amount of compound (III) is usually about 1–5 mol, preferably about 1–2 mol, per compound (II) 1 mol. The reaction may be carried out at about −80 to 80° C., preferably about −40 to 50° C.

Compound (II) is prepared, for example, by reacting a compound of the formula (I'):

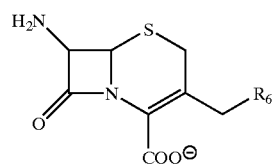
(II')

wherein $R^6$ is a leaving group (e.g., hydroxy, halogen (e.g., Cl, Br, I), carbamoyloxy, substituted carbamoyloxy, and acyloxy), an ester or salt thereof (hereinafter referred to as compound (II')) with an imidazo[4,5-b]pyridine compound of the formula (IV):

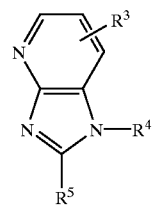
(IV)

wherein each symbol is the same as defined above, or a salt thereof (hereinafter referred to as compound(IV)).

Compound (II') may be prepared according to documents (e.g., JP(A) 60-231684 and JP(A) 62-149682). Examples of the acyloxy in $R^6$ include acetoxy, chloroacetoxy, propionyloxy, butylyloxy, pivaloyloxy, and 3-oxobutylyloxy. Examples of above substituted carbamoyloxy include methylcarbamoyloxy and N,N-dimethylcarbamoyloxy. Examples of the salt of compound (IV) include inorganic acid addition salts (e.g., hydrochloride, hydrobromate, sulfate, nitrate, and phosphate) and organic acid addition salts (e.g., formate, acetate, trifluoroacetate, methanesulfonate, and p-toluenesulfonate).

(Method 2)

Compound (I) is prepared by reacting a compound of the formula (V):

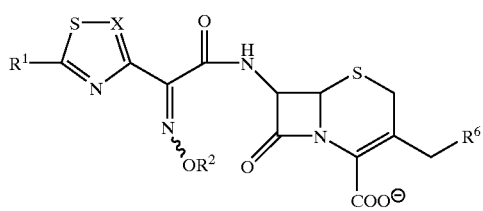
(V)

wherein each symbol is the same as defined above, an ester or salt thereof (hereinafter referred to as compound (V)) with the above-described compound (IV).

Examples of salts or esters of the compound (V) are the same as those of compound (I).

Examples of solvents used in the reaction are the same as those used in the above-described Method (1). In addition, compound (IV) may be used also as a solvent.

The amount of compound (IV) is usually about 1–5 eq. mol, preferably about 1–3 eq. mol, per compound (V). The reaction is usually conducted at about 0–100° C., preferably about 10–80° C., within several minutes to several hours.

In the process, a reaction mediator mat be added, such as iodides (e.g., NaI and KI) and thiocyanate (e.g., sodium thiocyanate and potassium thiocyanate). When $R^6$ is hydroxy, the reaction may be conducted in the presence of various phosphorus compounds according to JP(A) Kokai S58-43979.

(Method 3)

Compound (I), provided $R^2$ is not hydrogen, can be obtained by reacting a compound of the formula(VI):

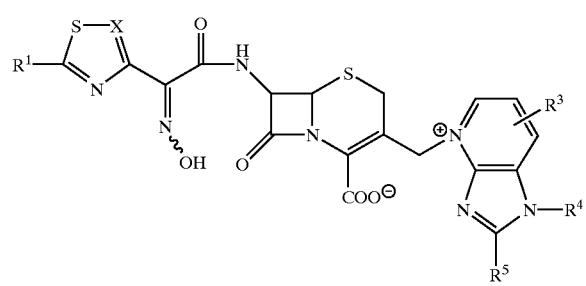

wherein each symbol is the same as above, an ester or, a salt thereof (hereinafter referred to as compound(VI)) with a compound of the formula: $R^2OH$ wherein $R^2$ is the same as above, or a reactive derivative thereof. The reactive derivative of $R^2OH$ includes a compound of the formula: $R^2Z$ wherein Z is a leaving group such as halogen, methanesulfonyloxy, and benzenesulfonyloxy.

(3-1) Reaction Using $R^2OH$

Compound (VI) and $R^2OH$ are reacted in the presence of an appropriate dehydrating agent. Examples of the dehydrating agent include phosphorus oxychloride, thionyl chloride, dialkyl azodicarboxylate/phosphine, and N,N'-dicyclohexylcarbodiimide. The reaction solvate includes e.g., the above-described ethers and hydrocarbons. The amount of compound $R^2OH$ is usually about 1 to 1.5 mol per compound (VI) 1 mol. The reaction temperature is usually about 0 to 50° C.

(3-2) Reaction Using $R^2Z$ $R^2Z$ and compound (VI) are reacted, if necessary, in the presence of a base. The reaction solvates include e.g., the above-described ethers, esters, halogenated hydrocarbons, hydrocarbons, amides, ketones, nitryls, alcohols, and water. The base includes for example, alkali metal salt (e.g., $Na_2CO_3$, $NaHCO_3$, $K_2CO_3$), alkali metal hydroxide (e.g., NaOH, KOH). The amount of $R^2Z$ is usually about 1 to 5 mol per compound(VI) 1 mol. The reaction temperature is about −30 to 100° C., preferably about 0 to 80° C. The above-described compound (IV) is known or new. Even when the compound (IV) is new, it can readily be synthesized through reactions well known to a person skilled in the art. A representative method is shown below.

Method A

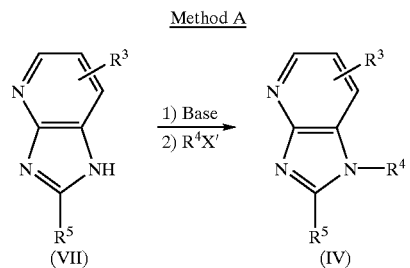

Compound (IV) can be prepared by reacting compound (VII) with $R^4X'$ ($R^4$ is the same as defined above, provided $R^4$ is not H. X' is a leaving group (e.g., Iodine and methanesulfonyloxy)) in the presence of a base (e.g., NaH and $CsCO_3$). The reaction can also be conducted under Mitsunobu's reaction condition: $R^4OH$/dialkyl axodicarboxylate/phosine. The reaction solvates include e.g., the above-described ethers and amides. The reaction temperature is about −20 to 150° C., preferably about 0 to 50° C.

The obtained compound (IV) may further be chemically modified to other compounds. Other methods B to F are shown below.

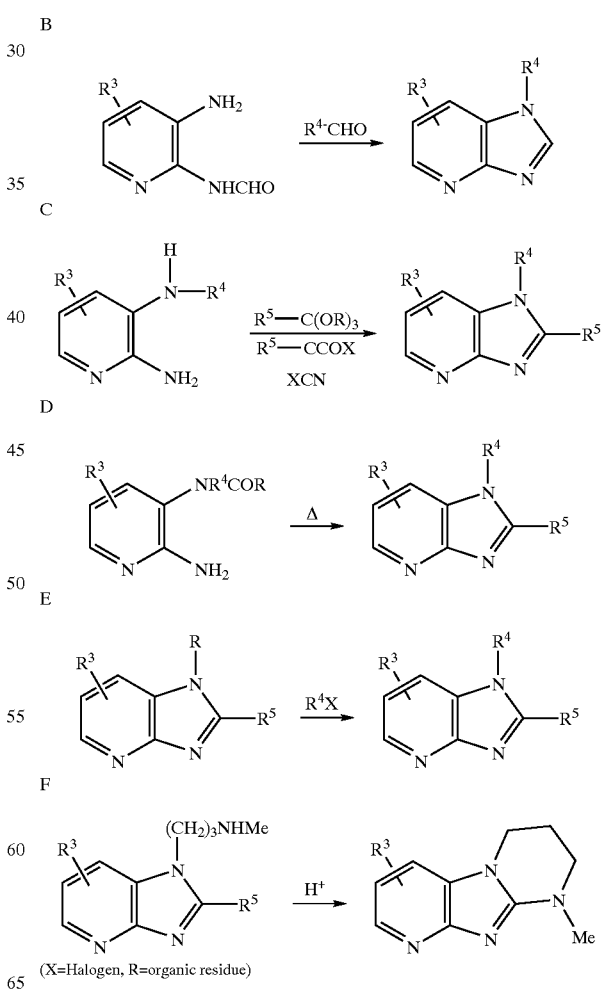

(X=Halogen, R=organic residue)

(Method 4)

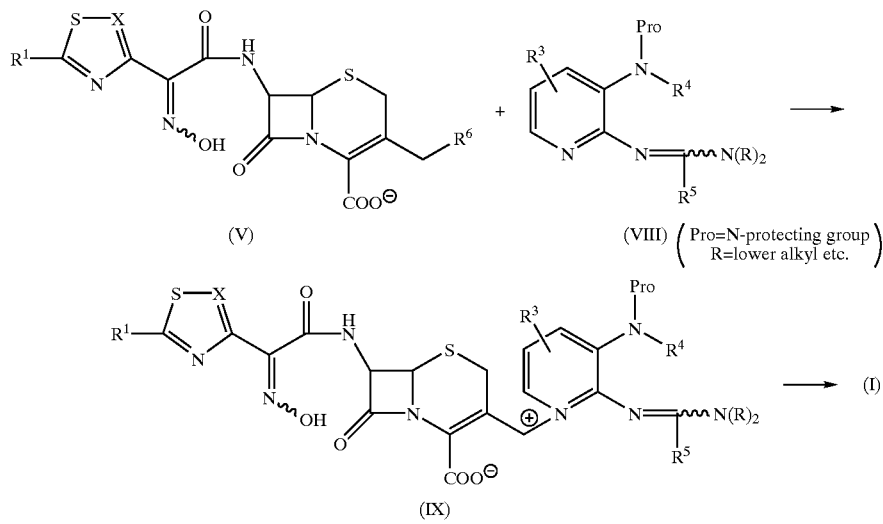

(Wherein Each Symbol is the Same as Defined Above)

Compound (V) and pridine derivative (VIII) are reacted to give compound (IX) (Step 1), then which is cyclized at the 3-side chain portion (Step 2), to give compound (I) (see, Reference Examples 31 to 33 and Examples 29 to 32.)

Step 1 reaction may be carried out according to the above Method 2. The 4-carboxy group of compound (IX) may be protected when $N^+$ of the 3-side chain is combined with a counter ion. The cyclization of Step 2 is preferably conducted in the presence of an acid. Examples of the acid include inorganic acids (e.g., HCl, $H_2SO_4$, $H_3PO_3$, $HNO_3$, toluene sulfonate, and methane sulfonate) and organic acids (e.g., $HCO_2H$ and $CH_3CO_2H$). Preferred is $H_2SO_4$ for the yield, handling or the like. The temperature of the acid-treating reaction is about −20 to about 100° C., preferably about 0 to about 30° C., and the reaction time is several minutes to several hours. The reaction solvates include acetic acid, ethyl acetate, acetonitrile, acetone, dimethylformamide (DMF), and tetrahydrofuran (THF). In a preferred embodiment of the Step 2 cyclization, the amino-protecting group (e.g., PMB and Boc) or 4-carboxy-protecting group (e.g., PMB) of compound (IX) can be deprotected.

Prior to the above each reaction, a functional group such as amino, imino, hydroxy, and carboxy may be protected by a method well known to skilled persons and if necessary deprotected after the reaction.

Compound (I) shows a broad antibacterial spectrum and so it can be used for preventing or treating mammals (e.g., humans) for various diseases caused by pathogenic microorganisms, such as respiratory tract infection and genito-urinary tract infection. The characters of compound (I) include the following points:

(1) excellent activity against Gram-negative bacteriums
(2) excellent activity against Gram-positive bacteriums
(3) excellent activity against methicillin-resistant S. aureus (MRSA)
(4) excellent activity against Pseudomonas
(5) excellent in vivo dynamics: high blood drug concentration, long time action, and good tissue transplantatio; compound (I) is not liable to be metabolized, thus the urinary recovery of the non-metabolite is high.
(6) excellent in water-solubility and safety.

Compound (I) can be orally or parenterally administered in a form of injection, capsule, granule, or the like, and a preferred form is injection. The daily dosage can usually be varied in the range of about 0.1 to 100 mg/kg, preferably about 0.5 to 50 mg/kg, which is administered in two to four divisions if necessary. The pharmaceutically acceptable carriers used to injections include e.g., distilled water, physiologic saline, and pH adjusting agents such as bases. For preparing capsules, granules, and tables, other pharmaceutically acceptable carriers can be used, such as excipients (e.g., starch, lactose, sucrose, calcium carbonate, calcium phosphate), binders (e.g., starch, Arabian gum, carboxymethyl cellulose, hydroxypropyl cellulose, crystalline cellulose), and lubricants (e.g., magnesium stearate, talc).

Examples are shown below.

(Abbreviation)

HP-20=HP-20SS (Daiya ion exchange resin, Mitsubishikagaku); Me=metyl; Et=ethyl; i-Pr=isopropyl; t-Bu=tert-butyl MeOH=methanol; EtOH=ethanol; i-PrOH=isopropanol; AcOH=acetic acid; AcOEt=ethyl acetate; $Et_2O$=diethylether; MeCN=acetonitrile; $MeNO_2$=nitromethane; DMF=dimethylformamide; THF=tetrahydrofuran; Boc=t-butoxycarbonyl; PMB=p-methoxybenzyl; BH=benzhydryl; Ms=methanesulfonyl

REFERENCE EXAMPLE 1

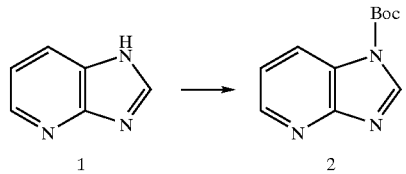

To a solution of compound 1 (Aldrich, 1775 mg, 6.5 mmol) in DMF 8 ml, was added di-tert-buthyl dicarbonate (hereinafter referred to as "$(Boc)_2O$") (1.65 ml, 1.1 eq) under ice-cooling and the mixture was allowed to stand at room temperature over night. The reaction mixture was evaporated under reduced pressure and the obtained oily residue was purified with silica gel chromatograph to give compound 2 (1.16 g, 81%).

$^1$H-NMR (CDCl$_3$) δ:1.71 (9H, s), 7.32 (1H, dd, J=4.8, 8.1 Hz), 8.28 (1H, dd, J=1.8, 8.1 Hz), 8.62 (1H, dd, J=1.8, 4.8 Hz), 8.66 (1H, s). IR (Nujole) cm$^{-1}$: 3136, 2979, 2853, 1761, 1744, 1606, 1577, 1531, 1506, 1403, 1370, 1156, 781. Elementary Analysis as C$_{11}$H$_{13}$N$_3$O$_2$.0.1H$_2$O; calc.: C, 59.77; H, 6.02; N, 19.01; found: C, 59.55; H, 6.03; N, 19.35 (%).

REFERENCE EXAMPLE 2

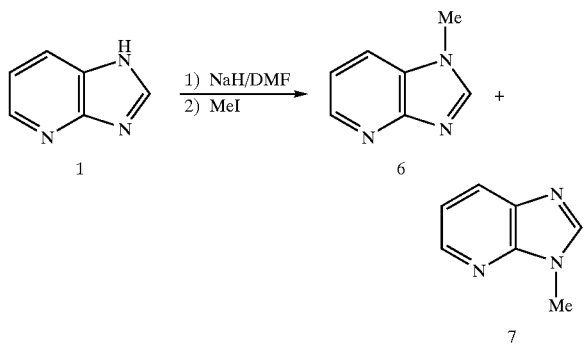

To a solution of compound 1 (Aldrich, 920 mg, 7.72 mmol) in THF 45 ml, was added 60% NaH (340 mg, 1.1 eq) under ice-cooling and the mixture was stirred at room temperature to 45° C. for 1 hr, then MeI (0.53 ml, 1.1 eq) was added thereto under ice-cooling at room temperature and the resultant mixture was allowed to stand over night. The reaction mixture was evaporated under reduced pressure and water and AcOE were added thereto, then the water layer was subjected to purification with HP-20 chromato, to give compound 6 (728 mg, 70.8%), then compound 7 (125 mg, 12%).
(Compound 6)
$^1$H-NMR (CDCl$_3$) δ: 3.87 (3H, s), 7.23 (1H, dd, J=5.1, 8.1 Hz), 7.68 (1H, dd, J=1.5, 8.1 Hz), 8.11 (1H, s), 8.50 (1H, dd, J=1.5, 5.1 Hz). Elementary Analysis as C$_7$H$_7$N$_3$.0.25H$_2$O; calc.: C, 61.08; H, 5.49; N, 30.53; found: C, 61.25; H, 5.38; N, 30.53 (%).
(Compound 7)
$^1$H-NMR (CDCl$_3$) δ: 3.94 (3H, s), 7.25 (1H, dd, J=4.8, 8.1 Hz), 8.04 (1H, s), 8.08 (1H, dd, J=1.5, 8.1 Hz), 8.43 (1H, dd, J=1.5, 4.8 Hz). Elementary Analysis as C$_7$H$_7$N$_3$.0.15H$_2$O; calc.: C, 61.89; H, 5.42; N, 30.93; found: C, 61.72; H, 5.54; N, 30.79 (%).

REFERENCE EXAMPLE 3

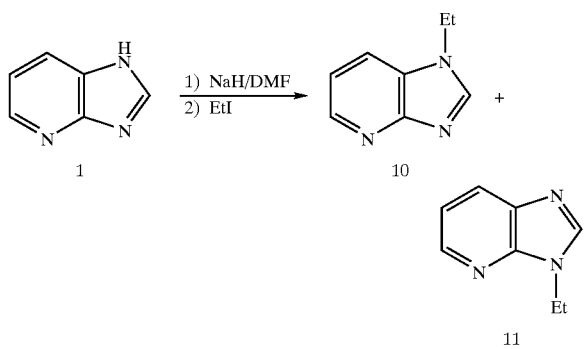

To a solution of compound 1 (Aldrich, 2.38 g, 20 mmol) in THF 100 ml, was added 60% NaH (880 mg, 1.1 eq) under ice-cooling and the mixture was stirred at room temperature for 1.5 hr, then EtI (1.8 ml, 1.05 eq) was added thereto under ice-cooling and the mixture was stirred at 4° C. for 3 days. The reaction mixture was filtered and concentrated under reduced pressure, then water and AcOEt were added threto. The separated water layer was subjected to purification with HP-20 chromato, to give compound 10 (2.14 g, 72.7%) and compound 11.
(Compound 10)
$^1$H-NMR (CDCl$_3$) δ: 1.57 (3H, t, J=7.5 Hz), 4.27 (2H, q, J=7.5 Hz), 7.25 (1H, dd, J=5.1, 8.1 Hz), 7.76 (1H, dd, J=1.5, 8.1 Hz), 8.16 (1H, s), 8.58 (1H, dd, J=1.5, 5.1 Hz). IR (film) cm$^{-1}$: 3399, 3084, 3052, 2981, 1650, 1610, 1494, 1415, 1379, 1293, 1222, 783. Elementary Analysis as C$_8$H$_9$N$_3$.1.9H$_2$O; calc.: C, 52.97; H, 7.11; N, 23.16; found: C, 53.12; H, 7.16; N, 23.18 (%).
(Compound 11)
$^1$H-NMR (CDCl$_3$) δ: 1.59 (3H, t, J=7.5 Hz), 4.38 (2H, q, J=7.5 Hz), 7.25 (1H, dd, J=5.1, 8.1 Hz), 8.06–8.09 (2H, m), 8.16 (1H, s), 8.42 (1H, dd, J=1.5, 5.1 Hz).

REFERENCE EXAMPLE 4

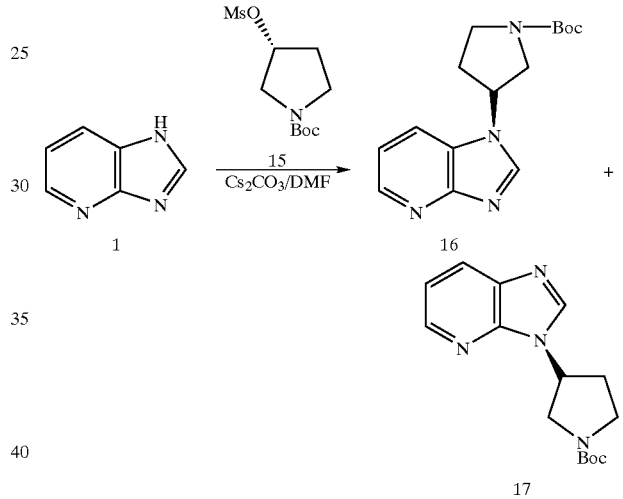

To a solution of compound 1 (Aldrich, 3.3 g, 27.7 mmol) in DMF 28 ml, were added compound 15 (9 g, 1 eq) and caesium carbonate (13.5 g, 1.5 eq) and the mixture was stirred at 80° C. for 2 hr. The reaction mixture was filtered and extracted with brine/AcOEt, then the organic layer was washed, dried over magnesium sulfate, and evaporated under reduced pressure. The residue was purified with silica gel chromatograph (CHCl$_3$/MeOH=9:1–4:1) to give compound 17 (2.47 g, 30%) in the nonpolor distillate and compound 16 (1.1 g, 13.7%) in the polor distillate.
(Compound 16)
$^1$H-NMR (d6-DMSO) δ: 1.39–1.43 (9H, m), 2.43–2.47 (2H, m), 3.52–3.60 (2H, m), 3.83–3.89 (1H, m), 5.20 (1H, brs), 7.30 (1H, dd, J=4.8, 8.1 Hz), 8.14 (1H dd, J=1.5, 8.1 Hz), 8.44 (1H, dd, J=1.5, 4.8 Hz), 8.55 (1H, brs). IR (Nujole) cm$^{-1}$: 3101, 1696, 1672, 1604, 1294, 1249, 1167, 1132, 788, 775. Elementary Analysis as C$_{15}$H$_{20}$N$_4$O$_2$; calc.: C, 62.48; H, 6.99; N, 19.43; found: C, 62.18; H, 6.90; N, 19.32 (%).
(Compound 17)
$^1$H-NMR (d6-DMSO) δ: 1.41–1.44 (9H, m), 2.5 (2H, brs), 3.31–3.88 (4H, m), 5.26(1H, brs), 7.33 (1H, dd, J=4.8, 8.1 Hz), 8.12 (1H, dd, J=1.5, 8.1 Hz), 8.40 (1H, dd, J=1.5, 3.6 Hz), 8.52 (1H, brs). IR (Nujole) cm$^{-1}$: 3110, 1670, 1596, 1577, 1243, 1168, 1114, 773.

REFERENCE EXAMPLE 5

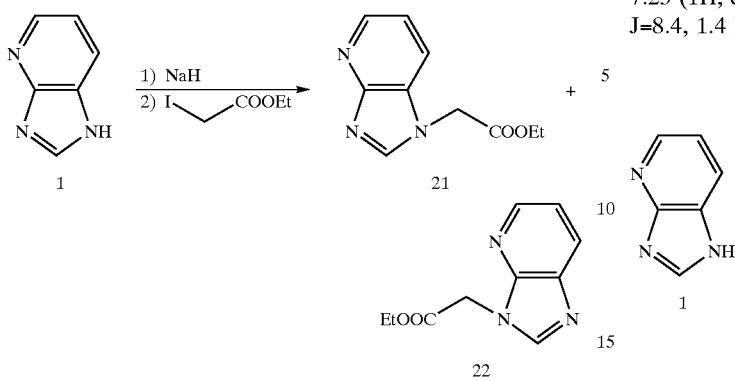

To a solution of compound 1 (5.11 g, 42.89 mmol) in THF 220 ml, was added 60%NaH (1.89 g, 1.1 eq) under ice-cooling in $N_2$ atomosphere and the mixture was stirred at room temperature for 15 min. The reaction mixture was cooled to −20° C. and ethyl iodoacetic acetate (5.33 ml, 1.05 eq) was added thereto, then the mixture was stirred under ice-cooling for 1 hr. THF in the reaction mixture was evaporated under reduced pressure, to which AcOEt was added and the mixture was washed with saturated brine. The organic layer was isolated, dried over magnesium sulfate, concentrated under reduced pressure, and purified with silica gel chromatograph. AcOEt eluted compound 22 (2.31 g, yield: 26%), then 7% MeOH/AcOEt eluted compound 21 (4.67 g, 53%).

(Compound 21)
$^1$H-NMR (CDCl$_3$) δ: 1.29 (3H, t, J=7.2 Hz), 4.27 (2H, q, J=7.0 Hz), 5.10 (2H, s), 7.28 (1H, dd, J=8.0, 4.8 Hz), 7.76 (1H, dd, J=8.0, 1.4 Hz), 8.49 (1H, dd, J=4.8, 1.4 Hz), 8.51 (1H s). IR (CHCl$_3$) cm$^{-1}$: 1755, 1499, 1420, 1365, 1295.

(Compound 22)
$^1$H-NMR (CDCl$_3$) δ: 1.29 (3H, t, J=7.0 Hz), 4.27 (2H, q, J=7.0 Hz), 5.08 (2H, s), 7.27 (1H, dd, J=8.0, 4.8 Hz), 8.1 (1H, dd, J=8.0, 1.4 Hz), 8.14 (1H, s), 8.40 (1H, dd, J=4.8, 1.4 Hz). IR (CHCl$_3$) cm$^{-1}$: 1749, 1500, 1415.

REFERENCE EXAMPLE 6

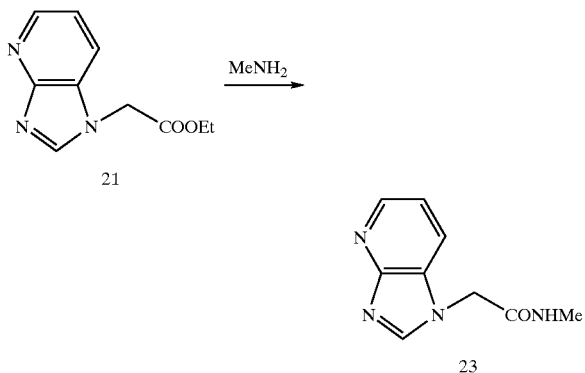

To a solution of compound 21 (1.03 g, 5 mmol) in MeOH 5 ml, was added at room temperature a solution of 30% methylamine in MeOH 5 ml and the mixture was stirred at the same temperature for 10 min. The reaction mixture was concentrated under reduced pressure to give compound 23 (0.95 g, 100%, yellow crystal).

$^1$H-NMR (CDCl$_3$) δ: 2.79 (3H, d, J=4.5 Hz), 4.88 (2H, s), 7.25 (1H, dd, J=8.4, 4.9 Hz), 7.75 (1H, brs), 7.82 (1H, dd, J=8.4, 1.4 Hz). IR (Nujol) cm$^{-1}$: 1670, 1585.

REFERENCE EXAMPLE 7

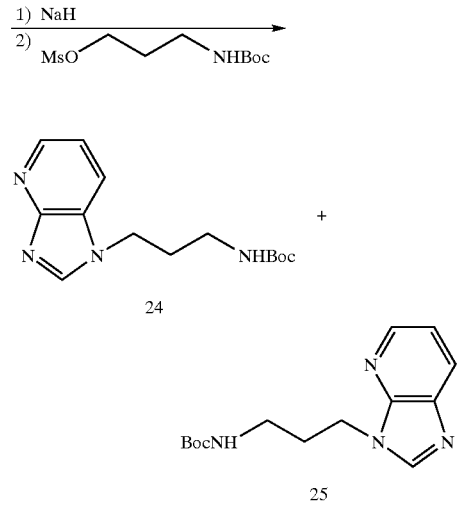

To a solution of compound 1 (1.85 g, 15.5 mmol) in DMF (15 ml), was added 60% NaH (0.68 g, 1.1 eq.) in $N_2$ atmosphere under ice-cooling and the mixture was stirred at room temperature for 10 min. To the reaction mixture was added a solution of mesylate (4.34 g, 1.1 eq.) in DMF (9 ml) and the mixture was stirred at 35° C. for 20 hr. The reaction mixture was concentrated under reduced pressure, then the residue was purified with silica gel chromatograph to give compound 25 (2.54 g, 59%) from AcOEt elution and compound 24 (1.14 g, 27%) from 7% MeOH/AcOEt elution, respectively.

(Compound 24)
$^1$H-NMR (CDCl$_3$) δ: 1.45 (9H, s), 2.11 (2H, m), 3.20 (2H, m), 4.27 (2H, t, J=10.5 Hz), 4.79 (1H, brs), 7.25 (1H, dd, J=11.7, 7.2 Hz), 7.75 (1H, dd, J=11.7, 1.5 Hz), 8.21 (1H, s), 8.59 (1H, dd, J=7.2, 1.5 Hz). IR (CHCl$_3$) cm$^{-1}$: 1700, 1490, 1160.

(Compound 25)
$^1$H-NMR (CDCl$_3$) δ: 1.46 (9H, s), 2.10 (2H, m), 3.12 (2H, m), 4.40 (2H, t, J=10.2 Hz), 5.30 (1H, brs), 7.27 (1H, dd, J=9.9, 7.2 Hz), 8.10 (1H, dd, J=9.9 Hz, 1.8 Hz), 8.12 (1H, s), 8.42 (1H, dd, J=7.2, 1.8 Hz). IR (CHCl$_3$) cm$^{-1}$: 1700, 1495, 1160.

REFERENCE EXAMPLE 8

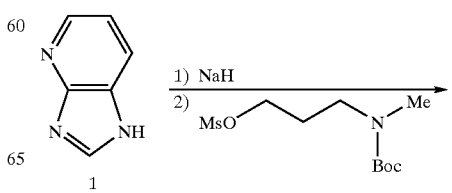

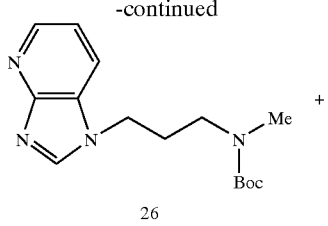

26

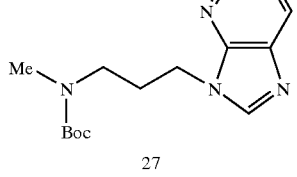

27

To a solution of compound 1 (4.15 g, 34.84 mmol) in DMF (35 ml), was added 60% NaH (1.53 g, 1.1 eq.) under ice-cooling in N$_2$ atmosphere with stirring and the mixture was further stirred at room temperature for 15 min. To the reaction mixture was added a solution of mesylate (10.26 g, 1.1 eq.) in DMF 20 ml and the mixture was stirred at 50° C. for 1.5 hr. The reaction mixture was concentrated under reduced pressure, then the residue was purified with silica gel chromatograph to give compound 27 (5.94 g, 59%) from AcOEt elution and compound 26 (2.90 g, 29%) from 6% MeOH/AcOEt elution.

(Compound 26) $^1$H-NMR (CDCl$_3$) δ: 1.45 (9H, s), 2.12 (2H, m), 2.85 (3H, s), 3.32 (2H, t, J=6.8 Hz), 4.22 (2H, t, J=7.0 Hz), 7.25 (1H, dd, J=8.2, 4.8 Hz), 7.74 (1H, dd, J=8.2, 1.4 Hz), 8.20 (1H, s), 8.60 (1H, dd, J=4.8, 1.4 Hz). IR (CHCl$_3$) cm$^{-1}$: 1670, 1480, 1465, 1400, 1380, 1350.

(Compound 27)
$^1$H-NMR (CDCl$_3$) δ: 1.44 (9H, s), 2.18 (2H, m), 2.85 (3H, s), 3.30 (2H, t, J=6.8 Hz), 4.32 (2H, t, J=7.2 Hz), 7.25 (1H, dd, J=8.1, 4.8 Hz), 8.08 (1H, dd, J=8.1, 1.4 Hz), 8.15 (1H, s), 8.40 (1H, dd, J=4.8, 1.4 Hz). IR (CHCl$_3$) cm$^{-1}$: 1681, 1500, 1410, 1395, 1369.

REFERENCE EXAMPLE 9

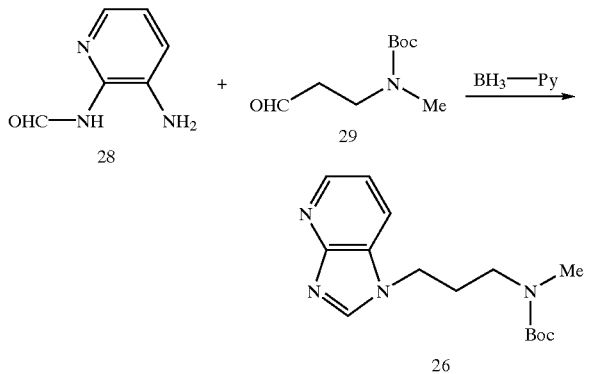

To a suspension of compound 28 (5.76 g, 42 mmol) and compound 29 (8.22 g, 1 eq.) in methylene chloride 40 ml, was added an ice-cooled mixture of methylene chloride 20 ml and AcOH 60 ml at −10° C. under stirring, to which was added a borane-pyridine complex (4.44 ml, 1 eq.) and the mixture was stirred at room temperature for 1 hr. The organic layer was separated, washed with a saturated brine, dried over MgSO$_4$, and concentrated under reduced pressure. The residue was purified with silica gel chromatograph with 10% MeOH/AcOEt to give compound 26 (11.25 g, 92%). The physical data was identical to that of Reference Example 8.

REFERENCE EXAMPLE 10

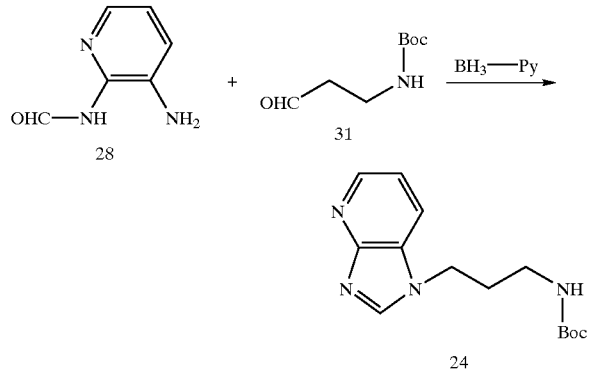

To a suspension of compound 28 (8.8 g, 64.16 mmol) and compound 31 (12.5 g, 1.1 eq.) in CH$_2$Cl$_2$ 120 ml, was added AcOH 91 ml and a borane-pyridine complex successively under ice-cooling and the mixture was stirred at room temperature for 1 hr. The reaction mixture was added to an ice-cooled solution (91 ml) of 28% ammonia water and AcOEt under stirring. The organic layer was separated, washed with a saturated brine, dried over MgSO$_4$, and concentrated under reduced pressure. The obtained residue was purified with silica gel chromatograph with 10% MeOH/AcOEt to give compound 24 (14.28 g, 80.5%). The physical data was identical to that of Reference Example 7.

REFERENCE EXAMPLE 11

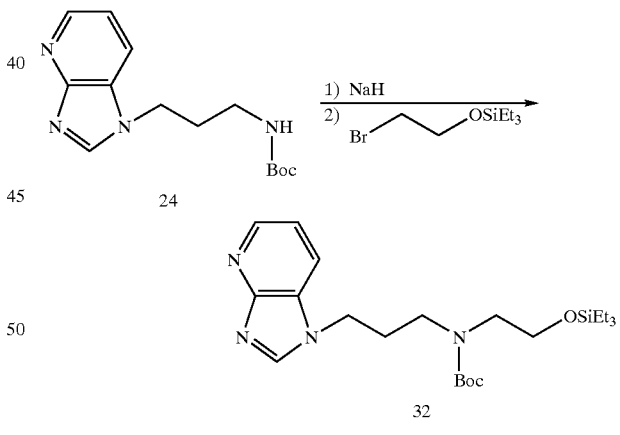

To a solution of compound 24 (1.14 g, 4.13 mmol) in DMF (6 ml), was added in N$_2$ atmosphere 60% NaH (0.25 g, 1.5 eq.) and the mixture was stirred at room temperature for 10 min. To the reaction mixture was added a solution of bromine compound (1.48 g, 1.5 eq.) in DMF (2 ml), and the mixture was stirred at room temperature for 1 hr, then 60% NaH (0.17 g, 1 eq.) and the same bromine compound (0.99 g, 1 eq.) were added thereto at room temperature under stirring for 2 hr. The reaction mixture was poured into a mixture of ice water and AcOEt under stirring. The organic layer was separated, washed with water and a saturated brine successively, dried over MgSO$_4$, and concentrated under reduced pressure. The residue was purified with silica gel chromatograph (5% MeOH/AcOEt) to give compound 32 (1.26 g, 70%).

¹H-NMR (CDCl₃) δ: 0.57 (9H, q, J=7.8 Hz), 0.93 (6H, t, J=7.8 Hz), 1.46 (9H, s), 2.15 (2H, m), 3.25 (2H, brs), 3.38 (2H, brs), 3.68 (2H, m), 4.21 (2H, t, J=7.2 Hz), 7.25 (1H, dd, J=7.8, 4.5 Hz), 7.75 (1H, dd, J=7.8, 1.2 Hz), 8.30 (1H, s), 8.59 (1H, dd, J=4.5, 1.2 Hz).

REFERENCE EXAMPLE 12

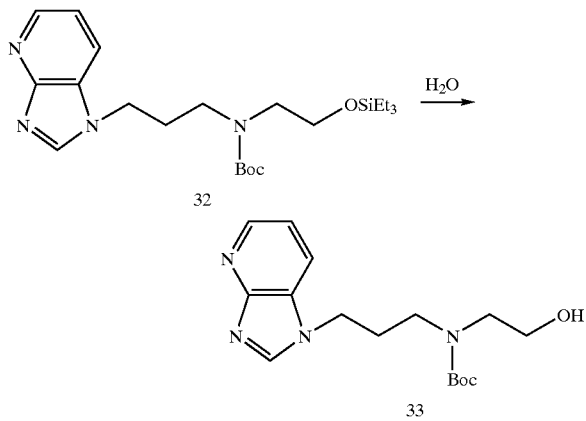

Compound 32 (1.26 g, 2.9 mmol) was mixed with THF 6 ml, AcOH 3 ml, and water 6 ml, and the mixture was stirred at room temperature for 30 min. The reaction mixture was poured into ice water/AcOEt with stirring. The water layer was separated, then which was adjusted to pH 8 with Na₂CO₃ for salting-out, and extracted with AcOEt. The organic layer was separated, dried over MgSO₄, and concentrated under reduced pressure to give compound 33 (0.93 g, 100%).

¹H-NMR (CDCl₃) δ: 1.42 (9H, s), 2.18 (2H, m), 3.38 (4H, m), 3.78 (2H, t, J=5.1 Hz), 4.23 (2H, t, J=7.5 Hz), 7.21 (1H, dd, J=8.1, 3.9 Hz), 7.74 (1H, dd, J=8.1, 1.2 Hz), 8.17 (1H, s), 8.55 (1H, dd, J=3.9 Hz, 1.2 Hz). IR (Nujol) cm⁻¹: 3160, 1690, 1420, 1050.

REFERENCE EXAMPLE 13

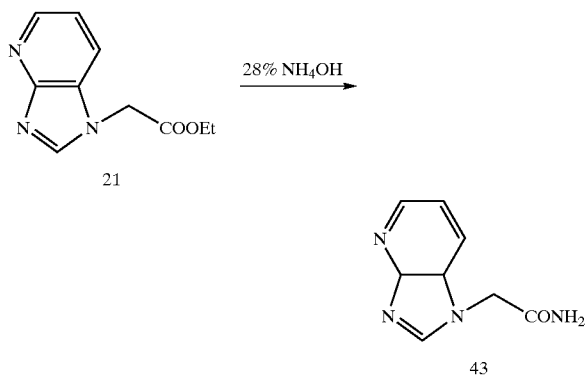

To a solution of compound 21 (3.47 g, 16.7 mmol) of Reference Example 5 in EtOH 20 ml, was added 28% ammonia water 20 ml at room temperature under stirring and the mixture was further stirred for 30 min. The reaction mixture was concentrated under reduced pressure and the residue was purified with HP-20SS to give compound 43 (1.41 g, yield 48%).

¹H-NMR (DMSO-d6) δ: 4.96 (2H, S), 7.27 (1H, dd, J=8.2 Hz, 4.8 Hz), 7.37 (1H, S), 7.76 (1H, S), 7.92 (1H, dd, J=8.2 Hz, 1.6 Hz), 8.40 (1H, dd, J=4.8 Hz, 1.6 Hz), 8.41 (1H, S). IR (Nujol) cm⁻¹: 3340, 1665, 1420, 1395, 1299.

REFERENCE EXAMPLE 14

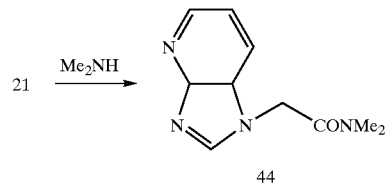

To a solution of compound 21 (1.03 g, 5 mmol) of Reference Example 13 in MeOH 5 ml, was added 50% dimethylamine aqueous solution 5 ml at room temperature with stirring for 30 min. The reaction mixture was concentrated under reduced pressure and the crystalline residue was washed with i-PrOH to give compound 44 (0.75 g, 73%).

¹H-NMR (DMSO-d6) δ: 2.87 (3H, S), 3.12 (3H, S), 5.32 (2H, S), 7.25 (1H, dd, J=8.0 Hz, 4.8 Hz), 7.95 (1H, dd, J=8.0 Hz, 1.0 Hz), 8.34 (1H, S), 8.40 (1H, dd, J=4.8 Hz, 1.0 Hz). IR (Nujol) cm⁻¹: 1639, 1480, 1403, 1280.

REFERENCE EXAMPLE 15

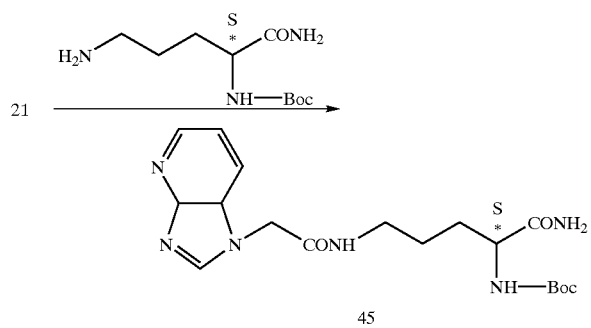

To a solution of compound 21 (1.01 g) of Reference Example 13 in MeOH 5 ml, was added a solution of amino compound (1.14 g, 1 eq.) in MeOH 5 ml under stirring at room temperature and the mixture was stirred for 4 hr. The reaction mixture was concentrated under reduced pressure and the residue was purified with HP-20 to give compound 45 (1.40 g, yield 73%).

¹H-NMR (CD₃OD) δ: 1.44 (9H, S), 1.6~2.0 (4H, m), 3.3 (2H, m), 4.0 (1H, m), 5.06 (2H, S), 7.38 (1H, dd, J=8.2 Hz, 5.0 Hz), 8.0 (1H, dd, J=8.2 Hz, 1.4 Hz), 8.42 (1H, S), 8.46 (1H, dd, J=5.0 Hz, 1.4 Hz). IR (Nujol) cm⁻¹: 3300, 1670, 1460, 1365.

REFERENCE EXAMPLE 16

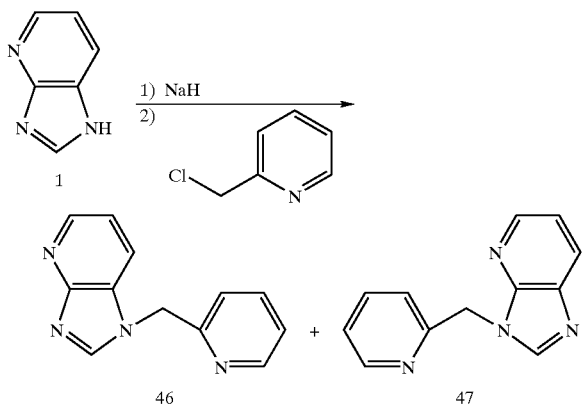

To a solution of compound 1 (2.38 g, 20 mmol) in DMF 15 ml, was added NaH (60% suspension in mineral oil, 0.88 g, 1.1 eq.) under ice-cooling in $N_2$ atmosphere and the mixture was stirred at room temperature for 10 min. To another solution containing 2-picolyl chloride hydrochloride (3.61 g, 1.1 eq.) in DMF 15 ml, was added NaH (60% suspension in mineral oil, 0.88 g, 1.1 eq.) under ice-cooling in $N_2$ atmosphere and the mixture was stirred at the same temperature for 15 min. Thus obtained both reaction mixtures were put together under ice-cooling to stir at room temperature for 1 hr. The final reaction mixture was concentrated under reduced pressure and the residue was purified with silica gel chromatograph to give compound 47 (2.05 g, yield 49%) from AcOEt elution and compound 46 (1.24 g, yield 30%) from 7% MeOH/AcOEt elution.

(Compound 46)
$^1$H-NMR (CDCl$_3$) δ: 5.50 (2H, S), 7.0 (1H, d, J=8.1 Hz), 7.24 (2H, m), 7.66 (2H, m), 8.29 (1H, S), 8.59 (2H, m). IR (CHCl$_3$) cm$^{-1}$: 1610, 1590, 1490, 1415, 1290.

(Compound 47)
$^1$H-NMR (CDCl$_3$) δ: 5.61 (2H, S), 7.24 (2H, m), 7.63 (1H, m), 8.09 (1H, m), 8.25 (1H, S), 8.42 (1H, m), 8.59 (1H, m). IR (CHCl$_3$) cm$^{-1}$: 1599, 1500, 1410, 1281.

REFERENCE EXAMPLE 17

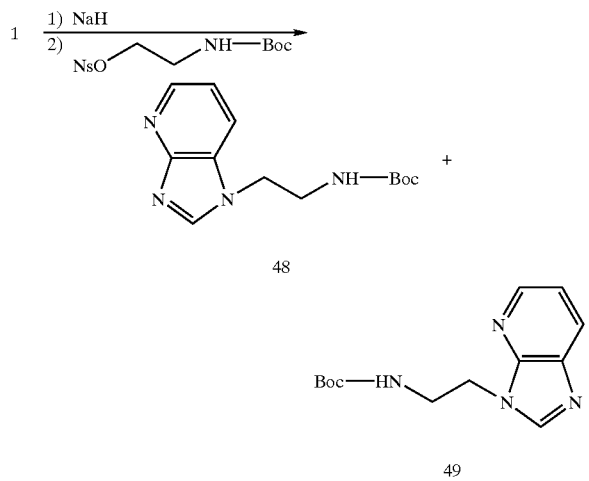

To a solution of compound 1 (1.19 g, 10 mmol) of Reference Example 16 in THF 50 ml, was added NaH (60% suspension in mineral oil, 0.44 g, 1.1 eq.) under stirring in $N_2$ atmosphere under ice-cooling and the mixture was stirred at room temperature for 15 min. To the reaction mixture was added a solution of mesylate (2.52 g, 1.1 eq.) in THF (10 ml) and the mixture was stirred at room temperature for 3 days. The reaction mixture was concentrated under reduced pressure and the residue was purified with silica gel chromatograph to give compound 48 (0.95 g, yield 36%) from 5% MeOH/AcOEt elution and compound 49 (0.48 g, yield 18%) from 8% MeOH/AcOEt elution.

(Compound 48)
$^1$H-NMR (CDCl$_3$) δ: 1.45 (9H, S), 3.57 (2H, q, J=6.0 Hz), 4.36 (2H, t, J=6.0 Hz), 5.51 (1H, S), 7.17 (1H, dd, J=8.2 Hz, 4.8 Hz), 7.75 (1H, dd, J=8.2 Hz, 1.6 Hz), 8.01 (1H, S), 8.47 (1H, dd, J=4.8 Hz, 1.6 Hz). IR (CHCl$_3$) cm$^{-1}$: 3450, 1703, 1499, 1409, 1370.

(Compound 49)
$^1$H-NMR (CDCl$_3$) δ: 1.40 (9H, S), 3.60 (2H, q, J=5.8 Hz), 4.46 (2H, t, J=5.8 Hz), 5.00 (1H, S), 7.25 (1H, dd, J=8.0 Hz, 4.8 Hz), 8.03 (1H, S), 8.07 (1H, dd, J=8.0 Hz, 1.6 Hz), 8.39 (1H, dd, J=4.8 Hz, 1.6 Hz). IR (CHCl$_3$) cm$^{-1}$: 3450, 1705, 1500, 1410, 1365.

REFERENCE EXAMPLE 18

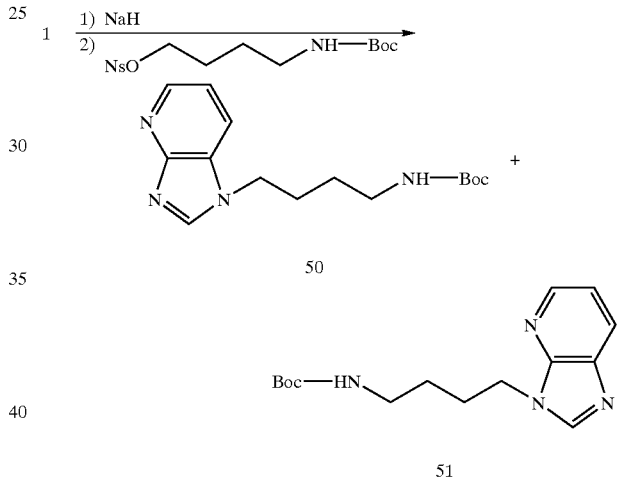

To a solution of compound 1 (1.87 g, 15.7 mmol) of Reference Example 16 in DMF 15 ml, was added NaH (60% suspension in mineral oil, 0.69 g, 1.1 eq.) under stirring in $N_2$ atmosphere under ice-cooling and the mixture was stirred at room temperature for 10 min. To the reaction mixture was added a solution of mesylate (4.62 g, 1.1 eq.) in DMF (8 ml) and the mixture was stirred at room temperature for 16 hr. The reaction mixture was concentrated under reduced pressure and the residue was purified with silica gel chromatograph to give compound 51 (2.77 g, yield 61%) from AcOEt elution and compound 50 (0.98 g, yield 22%) from 7% MeOH/AcOEt elution.

(Compound 50)
$^1$H-NMR (CDCl$_3$) δ: 1.44 (9H, S), 1.52 (2H, m), 1.93 (2H, m), 3.18 (2H, m), 4.25 (2H, t, J=6.9 Hz), 4.65 (1H, S), 7.23 (1H, dd, J=8.1 Hz, 4.8 Hz), 7.77 (1H, dd, J=8.1 Hz, 1.2 Hz), 8.12 (1H, S), 8.58 (1H, dd, J=4.8 Hz, 1.2 Hz). IR (CHCl$_3$) cm$^{-1}$: 3460, 1705, 1505, 1495.

(Compound 51)
$^1$H-NMR (CDCl$_3$) δ: 1.44 (9H, S), 1.55 (2H, m), 1.98 (2H, m), 3.18 (2H, m), 4.34 (2H, t, J=7.2 Hz), 4.70 (1H, S), 7.25 (1H, m), 8.07 (1H, S), 8.07 (1H, m), 8.40 (1H, d, J=4.8 Hz). IR (CHCl$_3$) cm$^{-1}$: 3460, 1705, 1500.

REFERENCE EXAMPLE 19

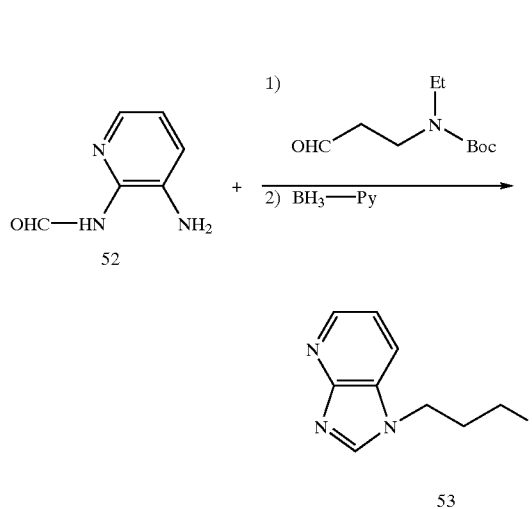

To a suspension of compound 52 (0.97 g, 7.1 mmol) and aldehyde (1.43 g, 1 eq.) in $CH_2Cl_2$ 6 ml, was added an ice-cooled solution of $CH_2Cl_2$ 4 ml-AcOH 10 ml under stirring and a borane-pyridine complex (0.72 ml, 1 eq.) successively, then the mixture was stirred room temperature for 1 hr. The reaction mixture was added to an ice-cooled solution of 28% ammonia water (10 ml) and AcOEt with stirring. The organic layer was separated, washed with a saturated brine, dried over $MgSO_4$, and concentrated under reduced pressure. The residue was purified with silica gel chromatograph to give compound 53 (1.75 g, yield 81%) from 10% MeOH/AcOEt elution.

$^1$H-NMR (CDCl$_3$) δ: 1.08 (3H, t, J=6.9 Hz), 1.44 (9H, S), 2.12 (2H, m), 3.25 (4H, m), 4.22 (2H, t, J=7.5 Hz), 7.20 (1H, dd, J=8.4 Hz, 4.5 Hz), 7.74 (1H, dd, J=8.4 Hz, 1.5 Hz), 8.20 (1H, S), 8.59 (1H, dd, J=4.5 Hz, 1.5 Hz). IR (CHCl$_3$) cm$^{-1}$: 1680, 1479, 1415, 1285.

REFERENCE EXAMPLE 20

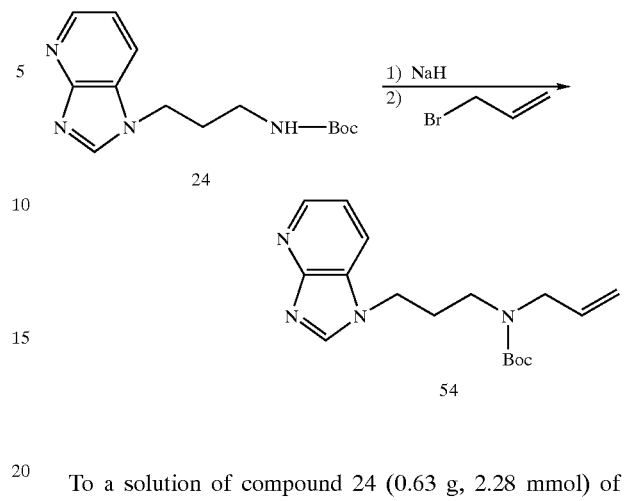

To a solution of compound 24 (0.63 g, 2.28 mmol) of Reference Example 10 in DMF 3 ml, was added NaOH (0.11 g, 1.2 eq.) under stirring at room temperature in $N_2$ atmosphere and the mixture was stirred at room temperature for 10 min. To the reaction mixture was added allyl bromide (237 μl, 1.2 eq.) under ice-cooling and the mixture was stirred at room temperature for 1 hr. The reaction mixture was poured into ice water/AcOEt, then the organic layer was separated, washed with a saturated brine, dried over $MgSO_4$, concentrated under reduced pressure. The residue was purified with silica gel chromatograph to give compound 54 (0.41 g, yield 57%) from 10% MeOH/AcOEt elution.

$^1$H-NMR (CDCl$_3$) δ: 1.44 (9H, S), 2.11 (2H, m), 3.28 (2H, m), 3.78 (2H, m), 4.21 (2H, t, J=7.2 Hz), 5.09 (2H, m), 5.74 (1H, m), 7.20 (1H, dd, J=8.1 Hz, 4.5 Hz), 7.73 (1H, dd, J=8.1 Hz, 1.5 Hz), 8.18 (1H, S), 8.59 (1H, dd, J=4.5 Hz, 1.5 Hz). IR (CHCl$_3$) cm$^{-1}$: 1675, 1480, 1410, 1350.

REFERENCE EXAMPLE 21

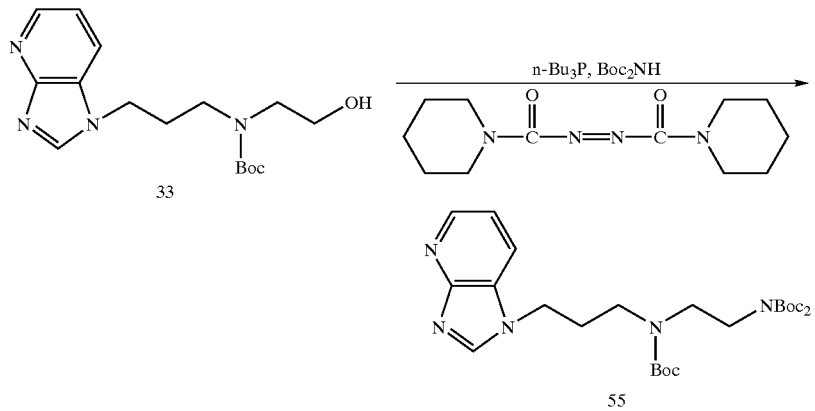

To a solution of compound 33 (0.97 g, 3.02 mmol) of Reference Example 12 in THF 15 ml, were added tri-n-butylphosine (1.13 ml, 1.5 eq.), di-tert-butyliminodicarboxylate (0.995 g, 1.5 eq.), and 1,1'-azodicarbonyldipiperidine (1.15 g, 1.5 eq.) under ice-cooling with stirring 15 min, then the mixture was further stirred room temperature for 3 hr. To the reaction mixture were added the above 3 kinds of reagents each 0.5 eq. and the mixture was stirred at room temperature for 2 hr. The reaction mixture was filtered to remove insoluble products, then the filtlate was dissolved in AcOEt, which was washed, dried over $MgSO_4$, and concentrated under reduced pressure. The residue was purified with silica gel chromatograph to give compound 55 (1.14 g, yield 72%) from 2% MeOH/$CHCl_3$ elution.

$^1$H-NMR ($CDCl_3$) δ: 1.48 (27H, S), 2.13 (2H, m), 3.37 (4H, m), 3.73 (2H, d, J=6.2 Hz), 4.21 (2H, d, J=7.4 Hz), 7.21 (1H, dd, J=7.8 Hz, 4.8 Hz), 7.75 (1H, dd, J=7.8 Hz, 1.2 Hz), 8.24 (1H, S), 8.58 (1H, dd, J=4.8 Hz, 1.2 Hz). IR ($CHCl_3$) $cm^{-1}$: 1680, 1478, 1420, 1290.

REFERENCE EXAMPLE 22

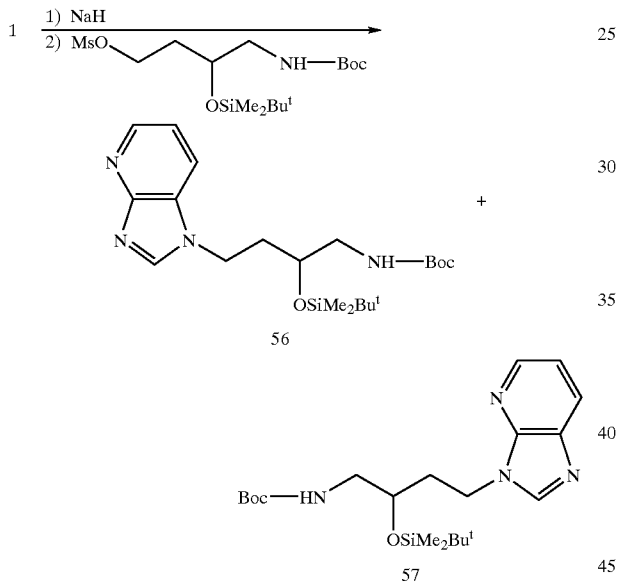

Compound 1 (1.03 g, 8.61 mmol) of Reference Example 16 was dissolved in DMF 8 ml, which was treated with 1.1 eq. of NaH and the mesylate according to Reference Example 18, to give compound 56 (0.89 g, yield 25%) and compound 57 (1.43 g, yield 39%).

(Compound 56)

$^1$H-NMR ($CDCl_3$) δ: 0.07 (3H, S), 0.08 (3H, S), 0.92 (9H, S), 1.45 (9H, S), 2.04 (2H, m), 3.21 (2H, m), 3.86 (1H, m), 4.31 (2H, m), 4.78 (1H, m), 7.23 (1H, dd, J=8.4 Hz, 4.8 Hz), 7.78 (1H, dd, J=8.4 Hz, 1.5 Hz), 8.14 (1H, S), 8.58 (1H, dd, J=4.8 Hz, 1.5 Hz). IR ($CHCl_3$) $cm^{-1}$: 3460, 1704, 1500, 1365.

(Compound 57)

$^1$H-NMR ($CDCl_3$) δ: 0.05 (3H, S), 0.06 (3H, S), 0.91 (9H, S), 1.44 (9H, S), 2.12 (2H, m), 3.24 (2H, m), 3.89 (1H, m), 4.38 (2H, t, J=7.2 Hz), 4.94 (1H, m), 7.20 (1H, dd, J=8.1 Hz, 4.8 Hz), 8.07 (1H, dd, J=8.1 Hz, 1.2 Hz), 8.08 (1H, S), 8.40 (1H, dd, J=4.8 Hz, 1.2 Hz). IR ($CHCl_3$) $cm^{-1}$: 3460, 1702, 1510, 1360.

REFERENCE EXAMPLE 23

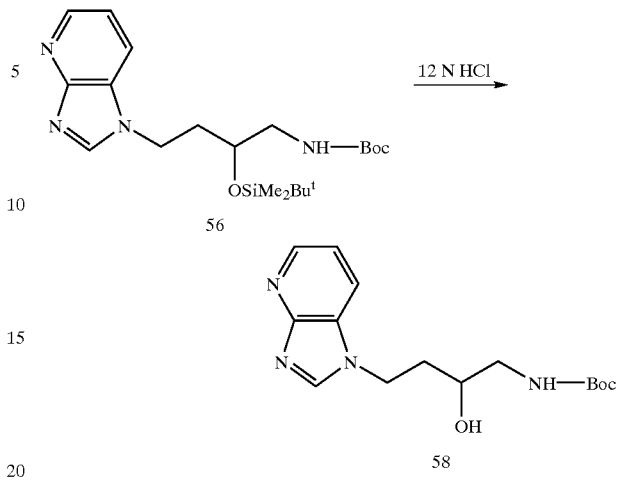

To a solution of compound 56 (0.89 g, 2.12 mmol) in MeCN 6 ml, was added 12N HCl (0.35 ml, 2 eq.) and the mixture was stirred at room temperature for 30 min. To the reaction mixture was added water and AcOEt with stirring, then the water layer was separated and basified with $Na_2CO_3$. The obtained solution was concentrated under reduced pressure up to 3 ml, then a solution of $(Boc)_2O$ 490 μml in dioxane 4 ml was added thereto at 50° C. and the mixture was stirred for 1 hr. The reaction mixture was concentrated under reduced pressure and the residue was purified with silica gel chromatograph to give compound 58 (0.36 g, yield 56%).

$^1$H-NMR ($CDCl_3$) δ: 1.40 (9H, S), 2.00 (2H, m), 3.21 (2H, m), 3.50 (1H, m), 4.48 (2H, m), 6.0 (1H, m), 7.22 (1H, dd, J=8.0 Hz, 5.0 Hz), 7.82 (1H, dd, J=8.0 Hz, 1.6 HZ), 8.23 (1H, S), 8.53 (1H, dd, J=5.0 Hz, 1.6 Hz). IR ($CHCl_3$) $cm^{-1}$: 3450, 1695, 1500, 1495.

REFERENCE EXAMPLE 24

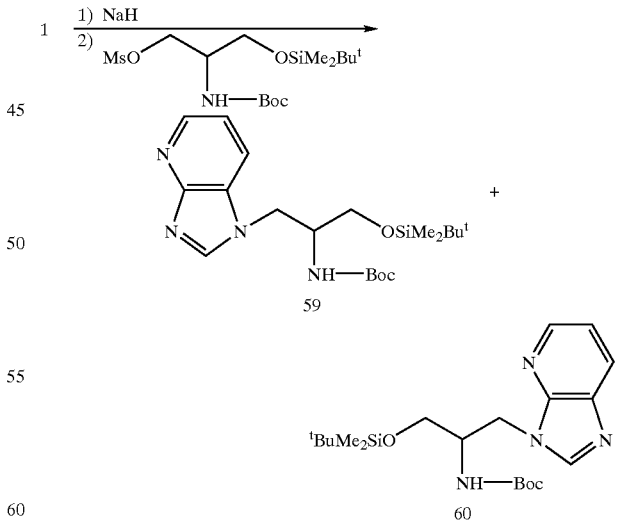

Compound 1 (1.93 g, 16.2 mmol) of Reference Example 16 was dissolved in DMF 15 ml, which was treated with 1.1 eq. of NaH and the mesylate according to Reference Example 18, to give compound 59 (0.57 g, yield 9%) and compound 60 (3.85 g, yield 58%).

(Compound 59)

¹H-NMR (CDCl₃) δ: 0.10 (6H, S), 0.96 (9H, S), 1.45 (9H, S), 3.53 (2H, m), 4.05 (1H, m), 4.37 (2H, d, J=6.6 Hz), 4.88 (1H, d, J=8.2 Hz), 7.24 (1H, dd, J=8.2 Hz, 4.6 Hz), 7.96 (1H, dd, J=8.2 Hz, 1.6 Hz), 8.08 (1H, S), 8.57 (1H, dd, J=4.6 Hz, 1.6 Hz). IR (CHCl₃) cm⁻¹: 3440, 1705, 1498, 1410, 1365.

(Compound 60)

¹H-NMR (CDCl₃) δ: 0.07 (6H, S), 0.93 (9H, S), 1.37 (9H, S), 3.51 (1H, m), 3.69 (1H, m), 4.14 (1H, m), 4.48 (2H, d, J=5.4 Hz), 5.51 (1H, m), 7.24 (1H, dd, J=8.4 Hz, 4.8Hz), 8.06 (1H, S), 8.08 (1H, dd, J=8.4 Hz, 1.5 Hz), 8.40 (1H, dd, J=4.8Hz, 1.5 Hz). IR (CHCl₃) cm⁻¹: 3450, 1708, 1495, 1410, 1363.

REFERENCE EXAMPLE 25

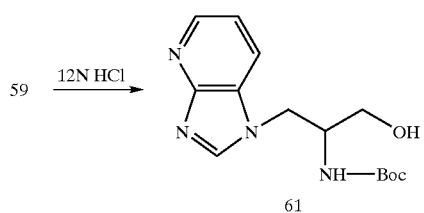

Compound 59 (0.57 g, 1.4 mmol) of Reference Example 24 was dissolved in MeCN 4 ml, then which was treated with 12N HCl 0.23 ml according to Reference Example 23, to give compound 61 (0.40 g, 97%).

¹H-NMR (CDCl₃) δ: 1.43 (9H, S), 3.70 (2H, m), 4.06 (1H, m), 4.50 (2H, m), 6.07 (1H, d, J=7.2 Hz), 7.25 (1H, dd, J=8.4 Hz, 5.1 Hz), 8.07 (1H, dd, J=8.4 Hz, 2.1 Hz), 8.20 (1H, S), 8.50 (1H, dd, J=5.1 Hz, 2.1 Hz). IR (CHCl₃) cm⁻¹: 3430, 1695, 1490, 1413, 1361, 1285.

REFERENCE EXAMPLE 26

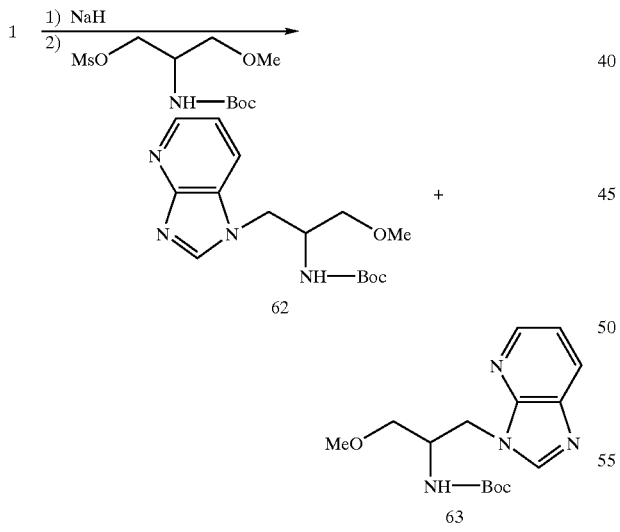

Compound 1 (1.06 g, 8.9 mmol) of Reference Example 16 was dissolved in DMF 8 ml, then which was treated with 1.1 eq. of NaH and the mesylate according to Reference Example 18, to give compound 62 (0.36 g, yield 19%) and compound 63 (1.43 g, 52%).

(Compound 62)

¹H-NMR (CDCl₃) δ: 1.45 (9H, S), 3.28 (2H, m), 3.37 (3H, S), 4.11 (1H, m), 4.37 (2H, d, J=6.6 Hz), 5.10 (1H, m), 7.29 (1H, dd, J=7.8 Hz, 4.2 Hz), 7.95 (1H, dd, J=7.8 Hz, 1.6 Hz), 8.13 (1H, S), 8.60 (1H, dd, J=4.2 Hz, 1.6 Hz). IR (CHCl₃) cm⁻¹: 3440, 1705, 1500, 1410, 1365.

(Compound 63)

¹H-NMR (CDCl₃) δ: 1.36 (9H, S), 3.34 (3H, S), 3.38 (2H, m), 4.22 (1H, m), 4.49 (2H, d, J=5.6 Hz), 5.55 (1H, m), 7.25 (1H, dd, J=8.0 Hz, 5.0 Hz), 8.05 (1H, S), 8.08 (1H, dd, J=8.0 Hz, 1.4 Hz), 8.40 (1H, dd, J=5.0 Hz, 1.4 Hz). IR (CHCl₃) cm⁻¹: 3440, 1708, 1500, 1408, 1370.

REFERENCE EXAMPLE 27

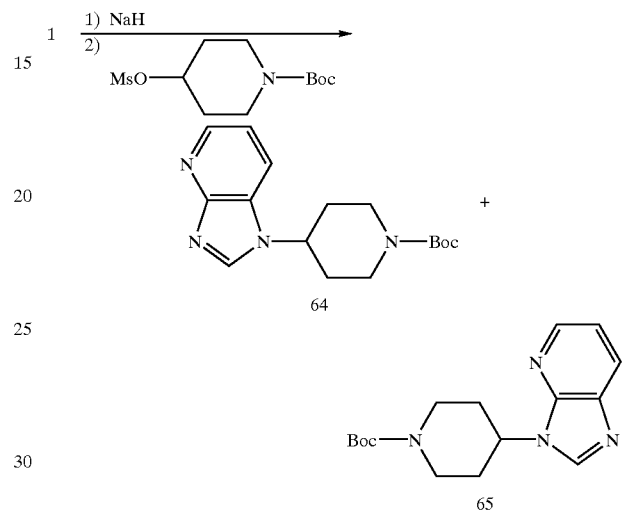

Compound 1 (2.14 g, 17.96 mmol) of Reference Example 16 was dissolved in DMF 15 ml, then which was treated with 1.1 eq. of NaH and the mesylate according to Reference Example 18, to give compound 64 (1.11 g, yield 20%) and compound 65 (1.86 g, yield 34%).

(Compound 64)

¹H-NMR (CDCl₃) δ: 1.51 (9H, S), 2.14 (4H, m), 2.94 (1H, m), 4.37 (4H, m), 7.25 (1H, dd, J=8.2 Hz, 4.6 Hz), 7.79 (1H, dd, J=8.2 Hz, 1.4 Hz), 8.21 (1H, S), 8.60 (1H, dd, J=4.6 Hz, 1.4 Hz). IR (CHCl₃) cm⁻¹: 1681, 1480, 1450, 1415, 1362.

(Compound 65)

¹H-NMR (CDCl₃) δ: 1.50 (9H, S), 2.10 (4H, m), 2.94 (1H, m), 4.35 (4H, m), 7.26 (1H, dd, J=8.0 Hz, 4.6 Hz), 8.09 (1H, dd, J=8.0 Hz, 1.2 Hz), 8.12 (1H, S), 8.40 (1H, dd, J=4.6 Hz, 1.2 Hz). IR (CHCl₃) cm⁻¹: 1681, 1488, 1421, 1405, 1363.

REFERENCE EXAMPLE 28

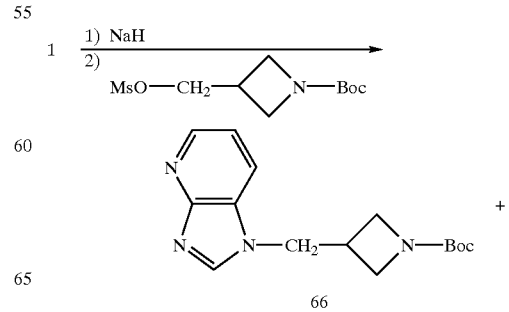

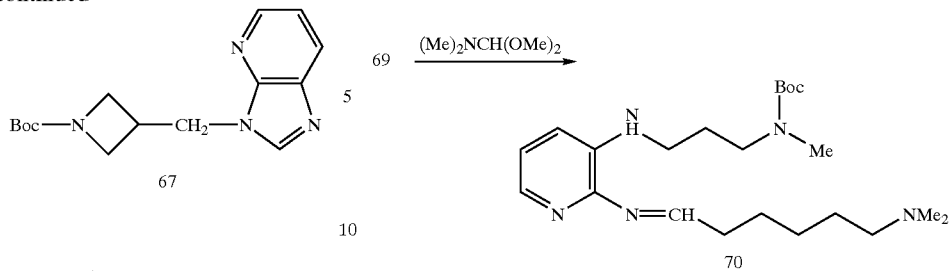

67

Compound 1 (0.78 g, 6.57 mmol) of Reference Example 16 in DMF 6 ml, then which was treated with 1.1 eq. of NaH and the mesylate according to Reference Example 18, to give compound 66 (0.42 g, yield 22%) and compound 67 (1.09 g, yield 57%).

(Compound 66)

$^1$H-NMR (CDCl$_3$) δ: 1.44 (9H, S), 3.08 (1H, m), 3.70 (2H, m), 4.06 (2H, m), 4.43 (2H, d, J=7.8 Hz), 7.27 (1H, dd, J=7.8 Hz, 4.6 Hz), 7.76 (1H, dd, J=7.8 Hz, 1.6 Hz), 8.14 (1H, S), 8.61 (1H, dd, J=4.6 Hz, 1.6 Hz). IR (CHCl$_3$) cm$^{-1}$: 685, 1503, 1415, 1370.

(Compound 67)

$^1$H-NMR (CDCl$_3$) δ: 1.44 (9H, S), 3.20 (1H, m), 3.77 (2H, m), 4.04 (2H, m), 4.52 (2H, d, J=7.8 Hz), 7.27 (1H, dd, J=8.2 Hz, 4.8 Hz), 8.07 (1H, S), 8.09 (1H, dd, J=8.2 Hz, 1.6 Hz), 8.41 (1H, dd, J=4.8 Hz, 1.6 Hz). IR (CHCl$_3$) cm$^{-1}$: 1688, 1500, 1416, 1370.

REFERENCE EXAMPLE 29

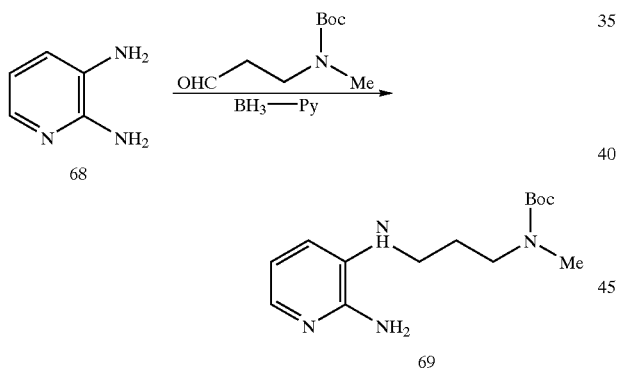

Compound 68 (161.5 g, 1.48 mol) was added to a mixture of CH$_2$Cl$_2$ 1.6 ml and AcOH 1.6 ml and the resulting mixture was stirred at room temperature, then cooled to −15° C. A borane/pyridine complex (150 ml, 1 eq.) and a solution of aldehyde (360.2 g, 1.3 eq.) in CH$_2$Cl$_2$ 300 ml were added thereto successively, and the mixture was stirred at −15° C. for 1 hr. The reaction mixture was washed with NaOH aq. and a saturated brine successively, then the organic layer was dried over Na$_2$SO$_4$ and evaporated under reduced pressure to give compound 69 (289 g, yield 69.6%). mp.101~4° C. (AcOH/Et$_2$O)

$^1$H-NMR (CDCl$_3$) δ: 1.44 (9H, S), 1.82 (2H, m), 2.84 (3H, S), 3.09 (2H, t, J=6.6 Hz), 3.56 (2H, t, J=6.6 Hz), 6.66 (1H, m), 6.75 (1H, m), 7.55 (1H, d, J=4.3 Hz). IR (CHCl$_3$) cm$^{-1}$: 1680, 1485, 1460, 1405.

REFERENCE EXAMPLE 30

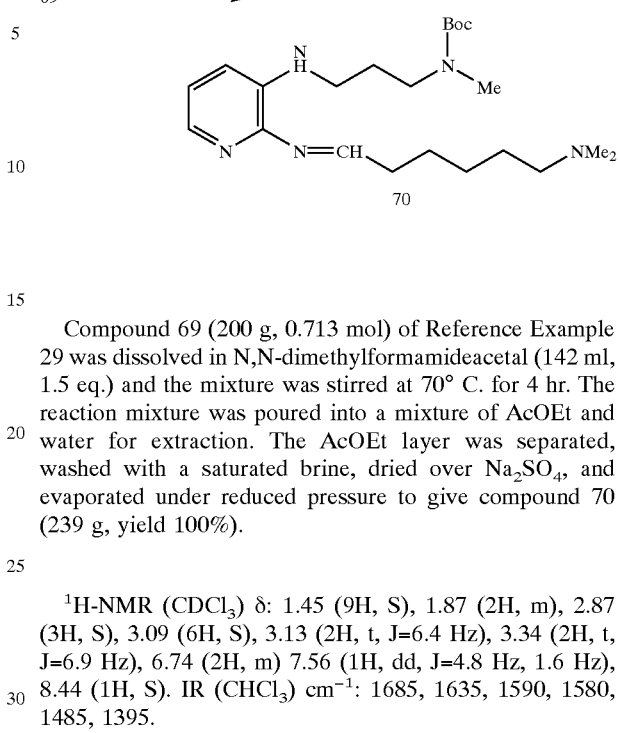

Compound 69 (200 g, 0.713 mol) of Reference Example 29 was dissolved in N,N-dimethylformamideacetal (142 ml, 1.5 eq.) and the mixture was stirred at 70° C. for 4 hr. The reaction mixture was poured into a mixture of AcOEt and water for extraction. The AcOEt layer was separated, washed with a saturated brine, dried over Na$_2$SO$_4$, and evaporated under reduced pressure to give compound 70 (239 g, yield 100%).

$^1$H-NMR (CDCl$_3$) δ: 1.45 (9H, S), 1.87 (2H, m), 2.87 (3H, S), 3.09 (6H, S), 3.13 (2H, t, J=6.4 Hz), 3.34 (2H, t, J=6.9 Hz), 6.74 (2H, m) 7.56 (1H, dd, J=4.8 Hz, 1.6 Hz), 8.44 (1H, S). IR (CHCl$_3$) cm$^{-1}$: 1685, 1635, 1590, 1580, 1485, 1395.

REFERENCE EXAMPLE 31

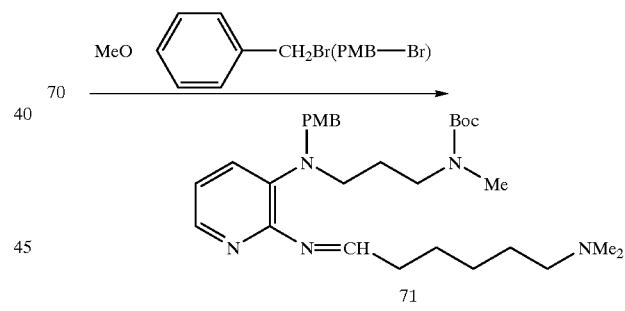

To a solution of compound 70 (50.8 g, 0.151 mol) of Reference Example 30 in DMF 250 ml, were added NaHCO$_3$ 38.17 g and p-methoxybenzyl bromide (PMB-Br, 33.5 g, 1.1 eq.) under stirring and the mixture was stirred at 25° C. for 3.5 hr. The reaction mixture was dissolved in AcOEt, which was washed with a saturated saline, dried over Na$_2$SO$_4$, and evaporated under reduced pressure to give compound 71 (59.46 g, yield 86%).

$^1$H-NMR (CDCl$_3$) δ: 1.39 (9H, S), 1.65 (2H, m), 2.70 (3H, S), 3.03 (3H, S), 3.07 (3H, S), 3.10 (4H, m), 3.78 (3H, S), 4.37 (2H, S), 6.80 (3H, m), 7.03 (1H, dd, J=7.9 Hz, 1.7 Hz), 7.23 (2H, d, J=8.7 Hz), 7.87 (1H, dd, J=4.7 Hz, 1.6 Hz), 8.33 (1H, S). IR (CHCl$_3$) cm$^{-1}$: 1685, 1635, 1580, 1520, 1405.

REFERENCE EXAMPLE 32

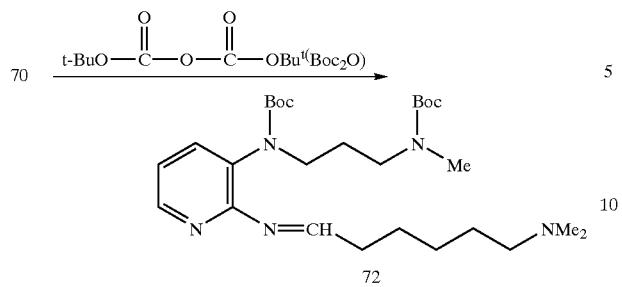

Compound 70 (312 g, 0.9291 mol) of Reference Example 30 and di-t-butyldicarbonate (243 g, 1.2 eq.) were dissolved in THF 624 ml and the mixture was refluxed under stirring for 3.5 hr. The reaction mixture was evaporated under reduced pressure to remove THF, then AcOEt was added to the residue, followed by etraction with a 10% aqueous solution of oxalic acid. The water layer was separated and basified with 4N NaOH aq., then which was extracted with AcOEt, washed, dried over $Na_2SO_4$, and evaporated to give compound 72 (356.9 g, yield 85%).

$^1$H-NMR (DMSO-d6) δ: 1.21 (9H, S), 1.35 (9H, S), 1.59 (2H, m), 2.70 (3H, S), 2.96 (3H, S), 3.08 (3H, S), 3.15 (2H, t, J=7.1 Hz), 6.89 (1H, dd, J=7.6 Hz, 4.8 Hz), 7.42 (1H, dd, J=7.6 Hz, 1.6 Hz), 8.08 (1H, dd, J=4.8 Hz, 1.6 Hz), 8.44 (1H, S). IR (CHCl$_3$) cm$^{-1}$: 1690, 1638, 1585, 1465, 1405.

REFERENCE EXAMPLE 33

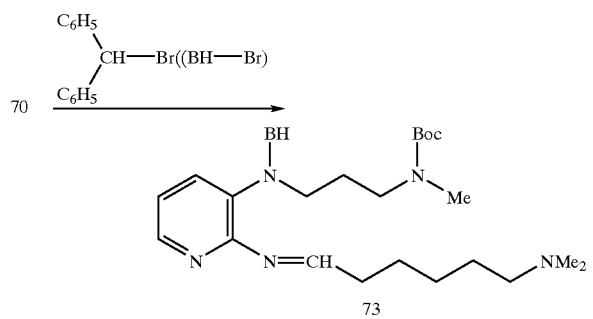

To a solution of compound 70 (3.50 g, 10 mmol) of Reference Example 30 in DMF 20 ml, were added NaHCO$_3$ (2.52 g) and diphenylmethyl bromide (BH-Br, 2.72 g, 1.1 eq.) under stirring succesively, and the mixture was stirred at 5° C. for 16 hr and at room temperature for 8 hr. The reaction mixture was dissolved in AcOEt, washed with water and a saturated brine, dried over Na$_2$SO$_4$, and evaporated under reduced pressure. Silica gel chromatograph gave compound 73 (2.55 g, yield 51%).

$^1$H-NMR (CDCl$_3$) δ: 1.35 (9H, S), 1.60 (2H, m), 2.67 (3H, S), 2.80 (3H, S), 2.88 (2H, t, J=7.5 Hz), 3.04 (3H, S), 3.13 (2H, m), 6.15 (1H, S), 6.70 (1H, dd, J=7.8 Hz, 4.8 Hz), 6.91 (1H, dd, J=7.8 Hz, 1.8 Hz), 7.21 (10, m), 7.88 (1H, dd, J=4.8 Hz, 1.8 Hz), 8.33 (1H, S). IR (CHCl$_3$) cm$^{-1}$: 1685, 1625, 1572, 1400.

EXAMPLE 1

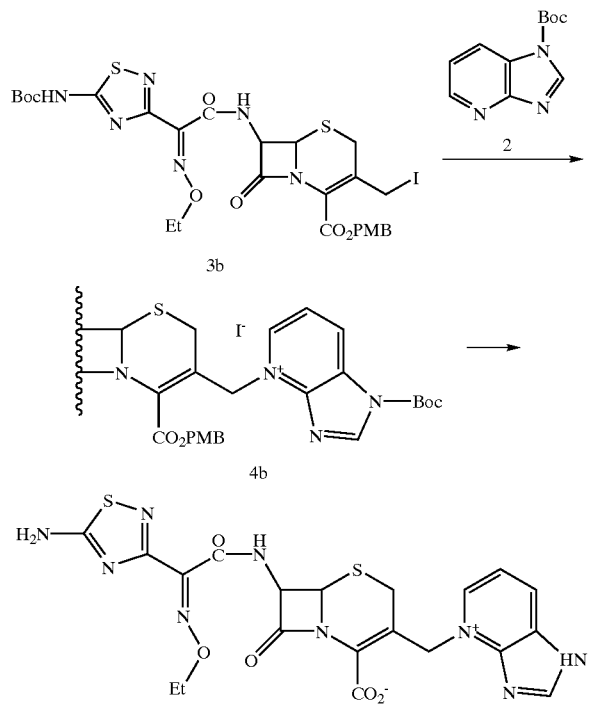

(1) To a solution of compound 2 (776 mg, 3.53 mmol) in dried MeCN 5 ml, was added compound 3 (3.21 g, 1.2 eq.) under ice-cooling and the mixture was allowed to stand over night. The resulting mixture was stirred at room temperature for 3 hr and evaporated under reduced pressure to give foamy compound 4b.

(2) To a solution of compound 4b in a mixture of CH$_2$Cl$_2$ 35 ml, MeNO$_2$ 15 ml, and anisole 10 ml, was added a AlCl$_3$—MeNO$_2$ solution (1.5M, 20 ml) in N$_2$ atmosphere under ice-cooling for 1.5 hr. Ice, 1N HCl, and Et$_2$O were added thereto, then the water layer was separated, and concentrated under reduced pressure. After HP-20 chromato, the collected portions were lyophilized to give compound 5b (colorless powder, 583 mg).

$^1$H-NMR (D$_6$-DMSO) δ: 1.18 (3H, t, J=7.2 Hz), 3.10 and 3.50 (2H, ABq, J=18 Hz), 4.10 (2H, q, J=7.2 Hz), 5.12 (1H, d, J=5.1 Hz), 5.62 (2H, Abq, J=14.4 Hz), 5.79 (1H, dd, J 5.0, 8.5 Hz), 7.54 (1H, dd, J=6.4, 8.0 Hz), 8.10 (2H, brs), 8.55 (1H, d, J=5.1 Hz), 8.56 (1H, s), 8.72 (1H, d, J=6 Hz), 9.53 (1H, d, J=9 Hz). IR (KBr) cm$^{-1}$: 3340, 2983, 1773, 1665, 1609, 1527, 1388, 1037. Elementary Analysis as C$_{20}$H$_{19}$N$_9$O$_5$S$_2$.2.5H$_2$O; calc.: C, 41.81; H, 4.21; N, 21.94 (%); found: C, 41.54; H, 4.32; N, 22.10 (%).

Reaction schemes of Example 2-1 to Example 2-4 are shown below.

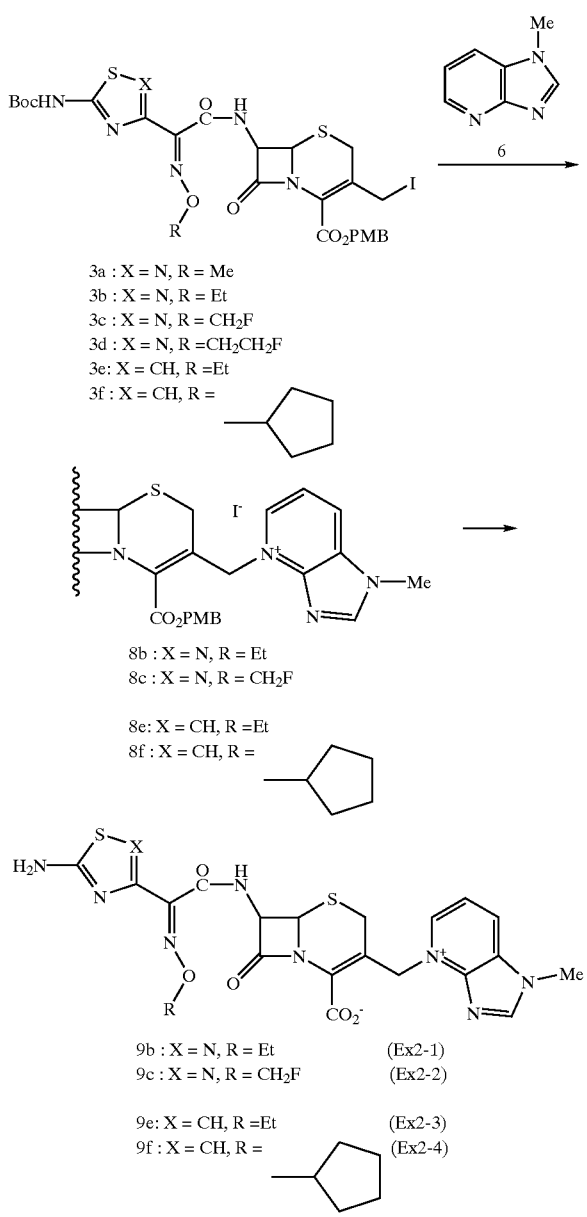

EXAMPLE 2-1

(1) To a solution of compound 6 (510 mg, 3.83 mmol) in dried MeCN 5 ml, was added compound 3b (3.34 g, 1.15 eq) under ice-cooling and the mixture was allowed to stand over night, then stirred at room temperature for 1 hr. The mixture was evaporated under reduced pressure to give crystalline compound 8b.

IR (Nujol) cm$^{-1}$: 3431, 3211, 1773, 1715, 1681, 1636, 1613, 1548, 1246, 1155, 1035.

(2) To a solution of compound 8b in a mixture of $CH_2Cl_2$ 40 ml, $MeNO_2$ 30 ml, and anisole 10 ml, was added an $AlCl_3$—$MeNO_2$ solution (1.5 mol, 15 ml) in $N_2$ atmosphere under ice-cooling and the mixture was stirred for 1.5 hr. Ice, 1N HCl and $Et_2O$ were added thereto, then the water layer was separated, concentrated under reduced pressure, and subjected to HP-20 chromato. The collected eluent was lyophilized to give compound 9b (colorless powder, 1.35 g).

$^1$H-NMR ($D_6$-DMSO) δ: 1.18 (3H, t, J=7.2 Hz), 2.95 and 3.52 (2H, ABq, J=17.4 Hz), 4.06 (3H, s), 4.04–4.19 (2H, m), 5.02 (1H, d, J=5.1 Hz), 5.64–5.69 (3H, m), 7.95 (1H, dd, J=6.3, 8.1 Hz), 8.13 (2H, brs), 8.88 (1H, dd, J=0.9, 8.1 Hz), 9.04 (1H, s), 9.44 (1H, d, J=8.7 Hz), 9.71 (1H, d, J=5.7 Hz). IR (KBr) cm$^{-1}$: 3386, 2984, 1773, 1665, 1636, 1614, 1528, 1389, 1357, 1038. Elementary Analysis as $C_{21}H_{21}N_9O_5S_2 \cdot 3.6H_2O$; calc.: C, 41.46; H, 4.67; N, 20.72; S, 10.54; found: C, 41.59; H, 4.79; N, 20.95; S, 10.70 (%).

EXAMPLE 2-2

(1) To a solution of compound 6 (153 mg, 1.1 mmol) in dried MeCN 2 ml, was added compound 3c (947 mg, 1.3 eq) under ice-cooling and the mixture was allowed to stand over night, then stirred at room temperature for 1 hr. The mixture was evaporated under reduced pressure to give crystalline compound 8c.

IR (Nujol) cm$^{-1}$: 3429, 3211, 1772, 1734, 1714, 1688, 1636, 1549, 1248, 1156, 1121.

(2) To a solution of compound 8c in a mixture of $CH_2Cl_2$ 30 ml, $MeNO_2$ 30 ml, and anisole 2 ml, was added $TiCl_4$ 0.73 ml in $N_2$ atomosphere atomosphere under ice-cooling and the mixture was stirred for 1.5 hr. Further procedures similar to Example 1 (2) gave compound 9c (colorless powder, 254 mg).

$^1$H-NMR ($D_6$-DMSO) δ: 2.95 and 3.54 (2H, ABq, J=17.4 Hz), 4.06 (3H, s), 5.03 (1H, d, J=5.1 Hz), 5.62–5.69 (3H, m), 5.71 (1H, d, J=55.2 Hz), 7.95 (1H, dd, J=6.3, 8.1 Hz), 8.18 (2H, brs), 8.87 (1H, d, J=8.4 Hz), 9.03 (1H, s), 9.66 (1H, d, J=8.4 Hz), 9.72 (1H, d, J=6.3 Hz). IR (KBr) cm$^{-1}$: 3398, 2984, 1774, 1671, 1614, 1528, 1394, 1359, 1064, 991. Elementary Analysis as $C_{20}H_{18}N_9O_5S_2F \cdot 3.8H_2O$; calc.: C, 39.00; H, 4.19; N, 20.46; S, 10.43; F, 3.09; found: C, 39.28; H, 4.19; N, 20.48; S, 10.43; F, 2.80 (%).

EXAMPLE 2-3

(1) To a solution of compound 6 (90 mg, 0.67 mmol) in dried MeCN 3 ml, was added compound 3e (716 mg, 1.4 eq) under ice-cooling and the mixture was allowed to stand over night, then stirred at room temperature for 1 hr. The reaction mixture was evaporated under reduced pressure to give compound 8e.

IR (Nujol) cm$^{-1}$: 3203, 1784, 1716, 1680, 1549, 1244, 1154, 1030.

(2) Compound 8e was deprotected and purified according to 8b, to give compound 9e (colorless powder, 220 mg).

$^1$H-NMR ($D_6$-DMSO) δ: 1.16 (3H, t, J=6.9 Hz), 2.98 and 3.54 (2H, ABq, J=18 Hz), 4.05 (2H, q, J=7 Hz), 4.07 (3H, s), 5.03 (1H, d, J=4.8 Hz), 5.64–5.68 (3H, m), 6.67 (1H, s), 7.19 (2H, brs), 7.96 (1H, dd, J=6, 8.4 Hz), 8.88 (1H, dd, J=0.3, 8.1 Hz), 9.04 (1H, s), 9.46 (1H, d, J=8.1 Hz), 9.73 (1H, dd, J=0.9, 6.6 Hz). IR (KBr) cm$^{-1}$: 3398, 2979, 1774, 1662, 1636, 1616, 1535, 1384, 1357, 1038. Elementary Analysis as $C_{22}H_{22}N_8O_5S_2 \cdot 3.8H_2O$; calc.: C, 43.24; H, 4.88; N, 18.34; S, 10.50; found: C, 43.23; H, 4.94; N, 18.50; S, 10.43 (%).

EXAMPLE 2-4

(1) To a solution of compound 6 (146 mg, 1.1 mmol) in dried MeCN 7 ml and DMF 2.5 ml, was added compound 3f (1.06 g, 1.25 eq) under ice-cooling and the mixture was allowed to stand over night, then stirred at room temperature for 1 hr. The reaction mixture was evaporated under reduced pressure to give compound 8f.

(2) Compound 8f was deprotected and purified according to 8b, to give compound 9f (colorless powder, 350 mg).

$^1$H-NMR ($D_6$-DMSO) δ: 1.46–1.74 (8H, m), 3.49 (1H, d, J=19.5 Hz), 4.08 (3H, s), 4.64 (1H, m), 4.86 (1H, d, J=4.8

Hz), 5.70 (2H, m), 5.80 (1H, dd, J=4.5, 8.1 Hz), 6.77 (1H, s), 7.18 (2H, brs), 7.92 (1H, dd, J=6.3, 8.1 Hz), 8.45 (1H, d, J=8.4 Hz), 8.89 (1H, d, J=8.1 Hz), 9.02 (1H, s), 9.45 (1H, d, J=6.3 Hz). IR (KBr) cm$^{-1}$: 3399, 2957, 2870, 1786, 1617, 1534, 1498, 1348, 1061, 1033, 989. Elementary Analysis as $C_{25}H_{26}N_{8}O_{5}S_{2}.4.7H_{2}O$; calc.: C, 45.0; H, 5.35; N, 16.79; S, 9.61; found: C, 45.01; H, 5.10; N, 16.95; S, 9.76 (%).

Reaction schemes of Example 3-1 to Example 3-4 are shown below.

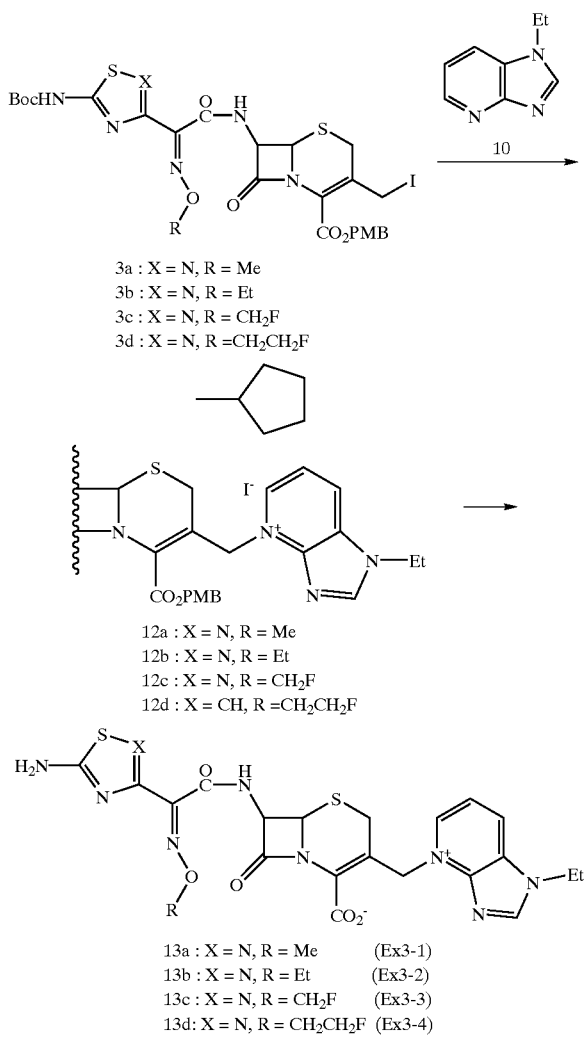

3a : X = N, R = Me
3b : X = N, R = Et
3c : X = N, R = CH$_2$F
3d : X = N, R = CH$_2$CH$_2$F

12a : X = N, R = Me
12b : X = N, R = Et
12c : X = N, R = CH$_2$F
12d : X = CH, R = CH$_2$CH$_2$F

13a : X = N, R = Me       (Ex3-1)
13b : X = N, R = Et       (Ex3-2)
13c : X = N, R = CH$_2$F  (Ex3-3)
13d: X = N, R = CH$_2$CH$_2$F (Ex3-4)

EXAMPLE 3-1

(1) To a solution of compound 10 (368 mg, 2.5 mmol) in dried MeCN 5 ml, was added compound 3a (2.33 g, 1.25 eq) under ice-cooling at room temperature and the mixture was stirred for 3 hr. The reaction mixture was evaporated under reduced pressure to give crystalline compound 12a.

IR (Nujol) cm$^{-1}$: 3448, 3211, 1733, 1714, 1683, 1635, 1613, 1551, 1248, 1156, 1038.

(2) To a solution of compound 12a in a miture of CH$_2$Cl$_2$ 35 ml, MeNO$_2$ 35 ml, and anisole 3 ml, was adde an AlCl$_3$—MeNO$_2$ solution (1.5M, 10 ml) in N$_2$ atmosphere under ice-cooling and the mixture was stirred for 2.5 hr. Ice, 1N HCl and Et$_2$O were added thereto, then the water layer was separated, concentrated under reduced pressure, and subjected to HP-20 chromato. The collected eluent was lyophilized to give compound 13a (colorless powder, 641 mg).

$^1$H-NMR (D$_6$-DMSO) δ: 1.52 (3H, t, J=7.2 Hz), 3.00 and 3.53 (2H, ABq, J=17.4 Hz), 3.83 (3H, s), 4.51 (2H, q, J=7.5 Hz), 5.01 (1H, d, J=4.5 Hz), 5.63–5.68 (3H, m), 7.95 (1H, dd, J=6.0, 8.4 Hz), 8.11 (2H, brs), 8.94 (1H, dd, J=0.9, 8.1 Hz), 9.13 (1H, s), 9.46 (1H, d, J=8.4 Hz), 9.71 (1H, d, J=6.0 Hz). IR (KBr) cm$^{-1}$: 3372, 3286, 2984, 2939, 1775, 1668, 1610, 1528, 1387, 1293, 1227, 1040. Elementary Analysis as $C_{21}H_{21}N_{9}O_{5}S_{2}.2.4H_{2}O$; calc.: C, 42.98; H, 4.43; N, 21.48; S, 10.93; found: C, 42.99; H, 4.63; N, 21.58; S, 10.65 (%).

EXAMPLE 3-2

(1) To a solution of compound 10 (240 mg, 1.63 mmol) in dried MeCN 1 ml, was added compound 3b (1.50 g, 1.2 eq) under ice-cooling and the mixture was stirred at room temperature for 2 hr, then evaporated under reduced pressure to give crystalline compound 12b.

IR (Nujol) cm$^{-1}$: 3429, 3203, 1773, 1714, 1681, 1634, 1612, 1548, 1245, 1154, 1034.

(2) Compound 12b was reacted according to 12a, to give lyophilized powder of compound 13b (630 mg).

$^1$H-NMR (D$_6$-DMSO) δ: 1.18 (3H, t, J=7.0 Hz), 1.51 (3H, t, J=7.2 Hz), 2.99 and 3.53 (2H, ABq, J=17.4 Hz), 4.10 (2H, q, J=6.9 Hz), 4.51 (2H, q, J=7.2 Hz), 5.01 (1H, d, J=4.5 Hz), 5.66–5.69 (3H, m), 7.94 (1H, t, J=6.6 Hz), 8.12 (2H, brs), 8.94 (1H, d, J=8.1 Hz), 9.12 (1H, s), 9.44 (1H, d, J=8.7 Hz), 9.67 (1H, d, J=6.3 Hz). IR (KBr) cm$^{-1}$: 3399, 2938, 1775, 1669, 1634, 1613, 1526, 1385, 1293, 1227, 1038. Elementary Analysis as $C_{22}H_{23}N_{9}O_{5}S_{2}.3.4H_{2}O$; calc.: C, 42.70; H, 4.85; N, 20.37; S, 10.24; found: C, 42.91; H, 5.03; N, 20.57; S, 9.88 (%).

EXAMPLE 3-3

(1) To a solution of compound 10 (368 mg, 2.5 mmol) in dried MeCN 7 ml, was added compound 3c (1.9 g, 1.15 eq) under ice-cooling and the mixture was stirred at room temperature for 3 hr, then allowed to stand at 4° C. over night. The reaction mixture was evaporated under reduced pressure to give compound 12c.

IR (Nujol) cm$^{-1}$: 3430, 3209, 1771, 1734, 1713, 1689, 1635, 1613, 1550, 1248, 1156, 1121.

(2) Compound 12c was reacted according to Example 2-2 (2) by TiCl$_4$-anisole method, to give lyophilized powder of compound 13c (350 mg).

$^1$H-NMR (D$_6$-DMSO) δ: 1.52 (3H, t, J=7.0 Hz), 2.99 and 3.54 (2H, ABq, J=17.4 Hz), 4.51 (2H, q, J=7.2 Hz), 5.04 (1H, d, J=4.8 Hz), 5.65–5.7 (3H, m), 5.71 (1H, d, J=55.5 Hz), 7.95 (1H, dd, J=6.0, 8.1 Hz), 8.19 (2H, brs), 8.94 (1H, dd, J=0.9, 8.1 Hz), 9.12 (1H, s), 9.65–9.71 (2H, m). IR (KBr) cm$^{-1}$: 3399, 2983, 1775, 1671, 1613, 1528, 1388, 1080, 991. Elementary Analysis as $C_{21}H_{20}N_{9}O_{5}S_{2}F.3.6H_{2}O$; calc.: C, 40.27; H, 4.38; N, 20.12; S, 10.24; F, 3.03; found: C, 40.43; H, 4.45; N, 20.23; S, 9.96; F, 2.66 (%).

EXAMPLE 3-4

(1) To a solution of compound 10 (368 mg, 2.5 mmol) in dried MeCN 6 ml, was added compound 3d (2.5 g, 1.3 eq) under ice-cooling and the mixture was stirred at the same temperature for 1 hr, then allowed to stand over night. The reaction mixture was evaporated under reduced pressure to give compound 12d.

IR (Nujol) cm$^{-1}$: 3190, 1783, 1714, 1634, 1612, 1546, 1245, 1153.

(2) Compound 12d was reacted according to 12c to give lyophilized powder of compound 13d (550 mg).

¹H-NMR (D₆-DMSO) δ: 1.51 (3H, t, J=7.0 Hz), 2.98 and 3.53 (2H, ABq, J=17.4 Hz), 4.25 (1H, m), 4.35 (1H, m), 4.46–4.54 (3H, m), 4.66 (1H, m), 5.02 (1H, d, J=5.1 Hz), 5.66–5.70 (3H, m), 7.94 (1H, dd, J=6.0, 8.1 Hz), 8.13 (2H, brs), 8.94 (1H, d, 8.4 Hz), 9.12 (1H, s), 9.52 (1H, d, 8.4 Hz), 9.67 (1H, d, 6.3 Hz). IR (KBr) cm⁻¹: 3399, 2984, 1775, 1670, 1612, 1528, 1386, 1292, 1228, 1066. Elementary Analysis as $C_{22}H_{22}N_9O_5S_2F·3H_2O$; calc.: C, 41.97; H, 4.48; N, 20.02; S, 10.18; F, 3.02; found: C, 42.22; H, 4.58; N, 20.15; S, 9.99; F, 2.73 (%).

Reaction schemes of Example 4-1 to Example 4-2 are shown below.

MeCN aq. containing 0.003N HCl, was lyophilized to give hydrochloride of compound 19b (powder, 360 mg).

¹H-NMR (D₆-DMSO) δ: 1.19 (3H, t, J=7.2 Hz), 2.52–2.74 (2H, m), 3.12 (1H, d, 18 Hz), 3.67–3.8 (2H, m), 4.11 (2H, q, J=7.2 Hz), 5.06 (1H, d, J=4.8 Hz), 5.61–5.07 (2H, m), 5.75 (1H, dd, J=4.8, 8.7 Hz), 5.84 (1H, d, J=14 Hz), 8.00 (1H, brt, J=7.0 Hz), 8.14 (2H, brs), 9.09 (1H, brd, J=8.1 Hz), 9.37 (1H, s), 9.42 (1H, d, J=5.7 Hz), 9.49 (1H, d, J=8.7 Hz).

¹H-NMR (D₂O) δ: 1.30 (3H, t, J=7.2 Hz), 2.68–2.80 (1H, m), 2.85–2.97 (1H, m), 3.31 and 3.63 (2H, ABq, J=18 Hz), 3.63–3.88 (3H, m), 4.08–4.19 (1H, m), 4.33 (2H, q, J=6.9 Hz), 5.22 (1H, d, J=4.5 Hz), 5.62 and 5.94 (2H, ABq, J=14.4 Hz), 5.62–5.72 (1H, m), 5.85 (1H, d, J=4.5 Hz), 7.92 (1H, dd, J=6.3, 8.4 Hz), 8.85 (1H, d, J=8.4 Hz), 8.89 (1H, d, J=5.7 Hz), 9.03 (1H, s). IR (KBr) cm⁻¹: 3398, 2982, 1771, 1668, 1611, 1461, 1391, 1037. Elementary Analysis as $C_{24}H_{26}N_{10}O_5S_2·1.25HCl·4.8H_2O$; calc.: C, 39.45; H, 5.08; N, 19.16; S, 8.78; Cl, 6.07; found: C, 39.45; H, 4.95; N, 19.16; S, 8.52; Cl, 6.08 (%).

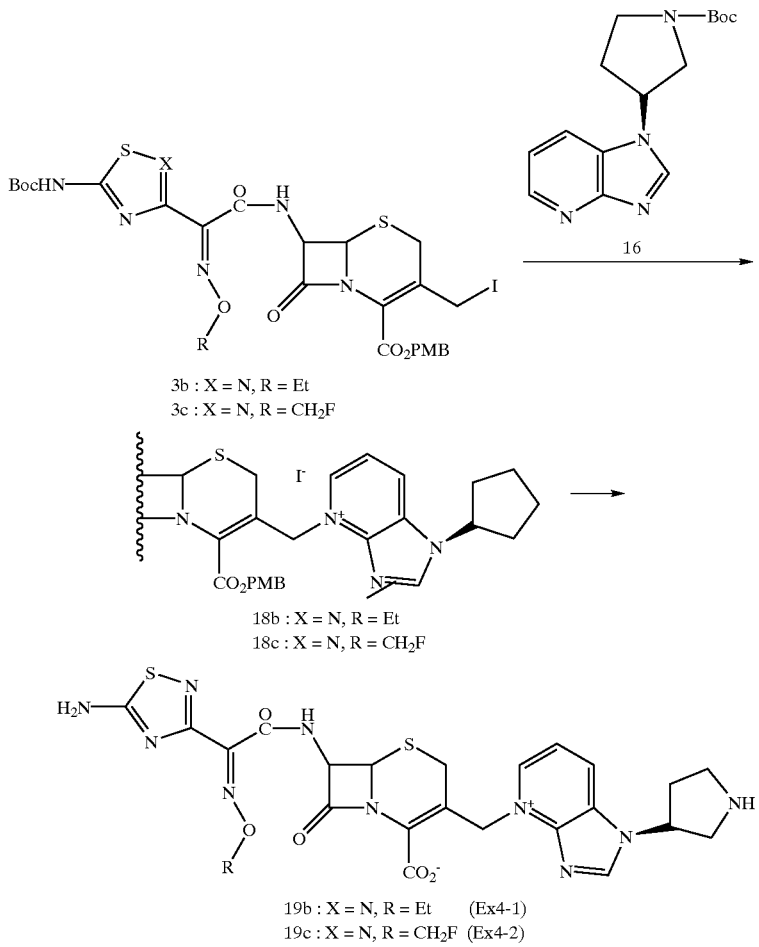

EXAMPLE 4-1

(1) To a solution of compound 16 (590 mg, 2 mmol) in dried MeCN 6 ml, was added compound 3b (1.86 g, 1.2 eq) under ice-cooling and the mixture was stirred at room temperature for 1.5 hr. The reaction mixture was diluted with Et₂O/EtOH to give crystalline compound 18b (2 g).

IR (Nujol) cm⁻¹: 3424, 3204, 1785, 1714, 1681, 1634, 1612, 1545, 1246, 1155, 1063.

(2) To a solution of compound 18b in CH₂Cl₂ 30 ml, MeNO₂ 35 ml, and anisole 3 ml, was added an AlCl₃—MeNO₂ solution (2 mol, 12 ml) in N₂ atmosphere under ice-cooling and the mixture was stirred for 2 hr. Ice, 1N HCl and Et₂O were added thereto, then the water layer was separated, concentrated under reduced pressure, and subjected to HP-20 chromato. The portion, eluted with 2%

EXAMPLE 4-2

(1) Compound 16 (355 mg, 1.2 mmol) was reacted according to Example 4-1 to give compound 18c.

IR (CHCl₃) cm⁻¹: 3221, 1773, 1717, 1692, 1612, 1153.

(2) Compound 18c was reacted according to Example 2-2 to give compound 19c (colorless powder, 31 mg).

$^1$H-NMR (D$_2$O) δ: 2.67–2.77 (1H, m), 2.82–2.94 (1H, m), 3.30 and 3.63 (2H, ABq, J=18 Hz), 3.58–3.84 (3H, m), 4.03–4.10 (1H, m), 5.23 (1H, d, J=4.8 Hz), 5.61 and 5.96 (2H, ABq, J=14.4 Hz), 5.61–5.72 (1H, m), 5.82 (1H, d, J=54 Hz), 5.87 (1H, d, J=4.5 Hz), 7.90 (1H, dd, J=6.3, 8.4 Hz), 8.84 (1H, d, J=8.4 Hz), 8.88 (1H, d, J=6.3 Hz), 9.00 (1H, s). IR (KBr) cm$^{-1}$: 3427, 1771, 1671, 1613, 1525, 1462, 1396, 1079, 1064. Elementary Analysis as C$_{23}$H$_{23}$N$_{10}$O$_5$S$_2$F.1.15 HCl.4.4H$_2$O; calc.: C, 38.16; H, 4.59; N, 19.35; S, 8.86; Cl, 5.63; F, 2.63; found: C, 38.13; H, 4.62; N, 19.66; S, 8.83; Cl, 5.84; F, 2.56 (%).

Reaction schemes of Example 5-1 to Example 5-4 are shown below.

further stirred for 2 hr. The reaction mixture was concentrated under reduced pressure, then Et$_2$O 50 ml was added to the residue, followed by filtration to give compound 34a (0.69 g, 78%) as powder.

$^1$H-NMR (DMSO-d6) δ: 1.38 (9H, s), 1.50 (9H, s), 2.00 (2H, m), 2.99 (2H, m), 3.40 (2H, m), 3.93 (3H, s), 4.50 (2H, m), 5.09 (1H, d, J=4.8 Hz), 5.28 (2H, s), 6.09, 5.58 (2H, ABq, J=14.8 Hz), 5.93 (1H, dd, J=8.6 Hz, 4.8 Hz), 6.93 (2H, d, J=8.6 Hz), 7.38 (2H, d, J=8.6 Hz), 7.96 (1H, dd, J=7.8 Hz, 6.2 Hz), 8.85 (1H, d, J=6.2 Hz), 9.01 (1H, d, J=7.8 Hz), 9.07 (1H, s), 12.6 (1H, s). IR (Nujol) cm$^{-1}$: 1770, 1679, 1550, 1460.

(2) Compound 34a (0.68 g, 0.666 mmol) was dissolved in CH$_2$Cl$_2$ 12 ml and MeNO$_2$ 3 ml and the mixture was cooled

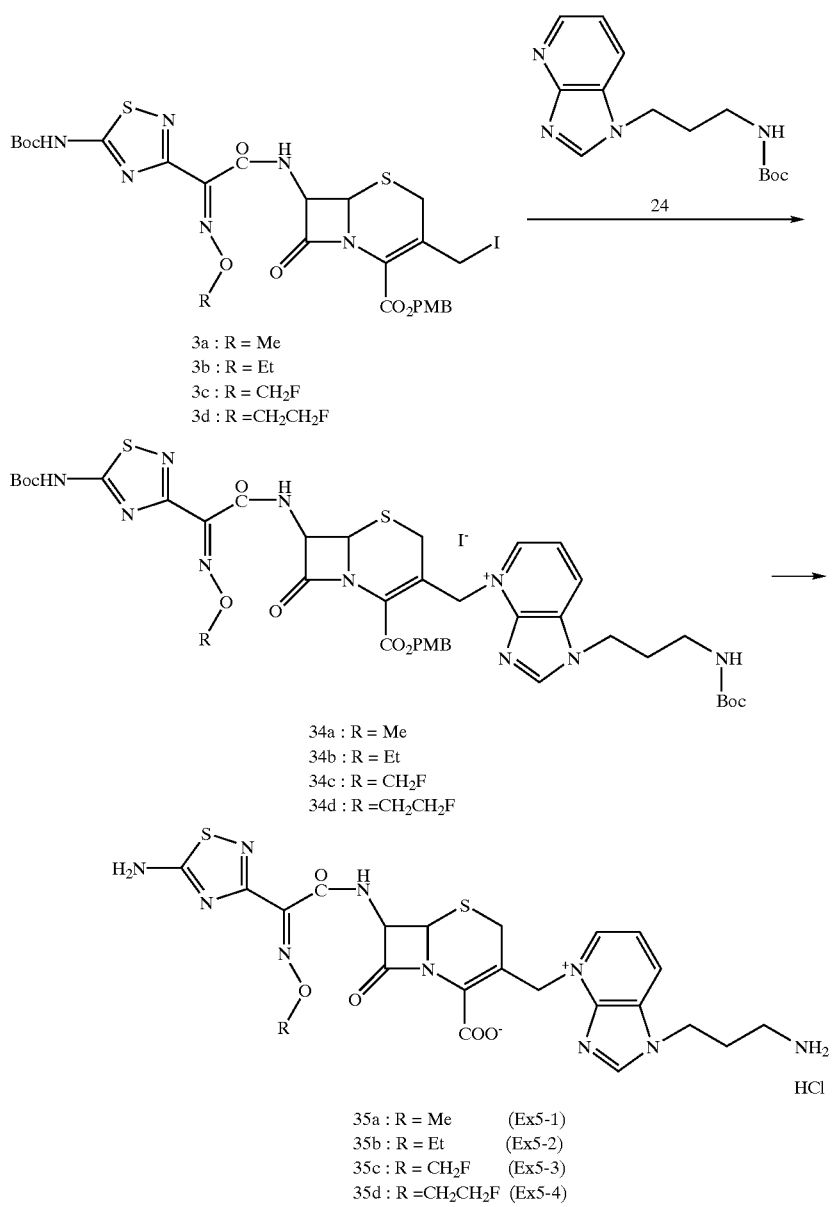

3a : R = Me
3b : R = Et
3c : R = CH$_2$F
3d : R = CH$_2$CH$_2$F

34a : R = Me
34b : R = Et
34c : R = CH$_2$F
34d : R = CH$_2$CH$_2$F

35a : R = Me       (Ex5-1)
35b : R = Et       (Ex5-2)
35c : R = CH$_2$F  (Ex5-3)
35d : R = CH$_2$CH$_2$F (Ex5-4)

EXAMPLE 5-1

(1) To a solution of compound 24 (0.24 g, 0.87 mmol) in MeCN 10 ml, was added compound 3a (0.71 g, 1.1 eq.) under stirring at room temperature and the mixture was to −20° C. Anisole (0.87 ml, 10 eq.) and an AlCl$_3$—MeNO$_2$ solution (1M, 6.7 ml, 10 eq.) were added thereto and the mixture was stirred at −56° C. for 1 hr. The reaction mixture was added to a mixture of 0.25N HCl 15 ml and Et$_2$O 30 ml under stirring. The water layer was separated, washed with Et₂O 120 ml, purified with HP-20. The eluted portion was lyophilized to give compound 35a (0.16 g, 37%).

$^1$H-NMR (D$_2$O) δ: 2.39 (2H, m), 3.13 (2H, t, J=8.7 Hz), 3.30, 3.64 (2H, ABq, J=12.1 Hz), 4.05 (3H, s), 4.64 (2H, t, J=7.2 Hz), 5.22 (1H, d, J=4.8 Hz), 5.62, 5.89 (2H, ABq, J=9.9 Hz), 5.85 (1H, d, J=4.8 Hz), 7.88 (1H, dd, J=8.1 Hz, 6.3 Hz), 8.80 (1H, d, J=8.1 Hz), 8.84 (1H, d, J=6.3 Hz), 8.88 (1H, s). IR (KBr) cm$^{-1}$: 1771, 1609, 1525, 1392.

EXAMPLE 5-2

(1) To a solution of compound 24 (0.41 g, 1.48 mmol) in DMF 7 ml, was added compound 3b (1.35 g, 1.2 eq.) under stirring and ice-cooling and the mixture was stirred at room temperature for 2 hr. The reaction mixture was slowly added to Et$_2$O 300 ml under stirring, then the precipitate was filtered to give compound 34b (1.46 g, 95%).

$^1$H-NMR (d$_6$-DMSO) δ: 1.24 (3H, t, J=7.2 Hz), 1.38 (9H, s), 1.50 (9H, s), 2.01 (2H, m), 3.30 (2H, m), 3.50 (2H, m), 3.77 (3H, s), 4.20 (2H, q, J=7.2 Hz), 4.50 (2H, t, J=7.8 Hz), 5.10 (1H, d, J=4.8 Hz), 5.29 (2H, s), 6.10, 5.58 (2H, ABq, J=14.7 Hz), 5.94 (1H, dd, J=8.6 Hz, 5.0 Hz), 6.94 (2H, d, J=9.0 Hz), 7,38 (2H, d, J=8.6 Hz), 7.96 (1H, dd, J=8.2 Hz, 5.8 Hz), 8.86 (1H, d, J=5.8 Hz), 9.01 (1H, d, J=8.2 Hz), 9,07 (1H, s), 9.67 (1H, d, J=8.6 Hz), 12.59 (1H, s). IR (Nujol) cm$^{-1}$: 1785, 1550, 1515, 1510, 1375.

(2) Compound 34b (1.45 g, 1.4 mmol) was dissolved in CH$_2$Cl$_2$ 28 ml and MeNO$_2$ 9 ml and the mixture was cooled to −20° C. Anisole (1.83 ml, 12 eq.) and an AlCl$_3$—MeNO$_2$ solution (1M, 14 ml, 10 eq.) were added thereto at −5° C. and the mixture was stirred for 1 hr. The reaction mixture was poured into a mixture of 0.25N HCl 60 ml and Et$_2$O 120 ml under stirring. The water layer was separated, washed with Et$_2$O 120 ml, and purified with HP-20. The eluted portion was lyophilized to give compound 35b (0.32 g, 31%).

$^1$H-NMR (D$_2$O) δ: 1.28 (3H, t, J=7.0 Hz), 2.36 (2H, m), 3.11 (2H, t, J=8.6 Hz), 3.28, 3.61 (2H, ABq, J=18.0 Hz), 4.615 (2H, t, J=7.0 Hz), 4.30 (2H, q, J=7.0 Hz), 5.21 (1H, d, J=4.6 Hz), 5.60, 5.87 (2H, ABq, J=14.7 Hz), 7.86 (1H, dd, J=8.2 Hz, 6.2 Hz), 8.78 (1H, d, J=8.2 Hz), 8.81 (1H, d, J=6.2 Hz), 8.85 (1H, s). IR (KBr) cm$^{-1}$: 1772, 1615, 1524, 1387. Elementary Analysis as C$_{23}$H$_{26}$N$_{10}$O$_5$S$_2$.1.3HCl.4.1H$_2$O; calc.: C, 39.02; H, 5.05; N, 19.79; S, 9.06; Cl, 6.51; found: C, 39.04; H, 5.10; N, 19.46; S, 9.08; Cl, 6.53.

EXAMPLE 5-3

(1) To a solution of compound 24 (0.71 g, 2.57 mmol) in DMF 10 ml, was added compound 3c (2.35 g, 1.2 eq.) under stirring and ice-cooling and the mixture was stirred at room temperature for 1 hr. The reaction mixture was slowly added to Et$_2$O 500 ml under stirring, then the precipitate was filtered to give compound 34c (2.79 g).

$^1$H-NMR (d$_6$-DMSO) δ: 1.38 (9H, s), 1.51 (9H, s), 2.0 (2H, m), 2.98 (2H, m), 3.48 (2H, m), 3.77 (3H, s), 4.50 (2H, t, J=7.8 Hz), 5.12 (1H, d, J=5 Hz), 5.28 (2H, s, 6.09, 5.59 (2H, ABq, J=14.6 Hz), 5.82 (2H, d, J=55.6 Hz), 5.95 (1H, m), 6.93 (2H, d, J=9 Hz), 7.38 (2H, d, J=9 Hz), 7.95 (1H, dd, J=7.8 Hz, 5.8 Hz), 8.85 (1H, d, J=5.8 Hz), 9.01 (1H, d, J=7.8 Hz), 9.08 (1H, s), 12.7 (1H, s). IR (Nujol) cm$^{-1}$: 1785, 1545, 1515, 1459, 1375.

(2) Compound 34c (2.78 g, 2.68 mmol) was dissolved in CH$_2$Cl$_2$ 50 ml and MeNO$_2$ 25 ml and the mixture was ice-cooled. Anisole (3.49 ml, 12 eq.) and TiCl$_4$ (2.94 ml, 10 eq.) were added thereto under stirring at 5° C. for 1 hr. The reaction mixture was poured into 0.25N HCl 150 ml and Et$_2$O 300 ml. The water layer was separated, washed with Et$_2$O 300 ml, and purified with HP-20. The eluted portion was lyophilized to give compound 35c (0.62 g, 33%).

$^1$H-NMR (D$_2$O) δ: 2.38 (2H, m), 3.13 (2H, t, J=8.4 Hz), 3.28, 3.64 (2H, ABq, J=17.9 Hz), 4.63 (2H, t, J=7.0 Hz), 5.23 (1H, d, J=4.8 Hz), 5.60, 5.87 (2H, ABq, J=14.7 Hz), 5.82 (2H, d, J=54.6 Hz), 7.86 (1H, dd, J=8.2 Hz, 6.2 Hz), 8.78 (1H, d, J=8.2 Hz), 8.82 (1H, d, J=6.2 Hz), 8.87 (1H, s). IR (KBr) cm$^{-1}$: 1773, 1614, 1525, 1390. Elementary Analysis as C$_{22}$H$_{23}$N$_{10}$O$_5$S$_2$F.1.2 HCl.3.6H$_2$O; calc.: C, 37.79; H, 4.53; N, 20.03; S, 9.17; F, 2.72; Cl, 6.08; found: C, 37.76; H, 4.61; N, 20.22; S, 8.89; F, 2.56; Cl, 6.00.

EXAMPLE 5-4

(1) To a solution of compound 24 (0.28 g, 1.01 mmol) in MeCN 10 ml, was added compound 3d (1.02 g, 1.3 eq.) under stirring at room temperature for 2 hr. The reaction mixture was concentrated under reduced pressure, then Et$_2$O 50 ml was added to the residue, followed by filtration to give compound 34d (1.19 g) as powder.

$^1$H-NMR (d$_6$-DMSO) δ: 1.38 (9H, s), 1.51 (9H, s), 2.00 (2H, m), 2.97 (2H, m), 3.50 (2H, m), 3.77 (3H, s), 4.30 (2H, m), 4.50 (4H, m), 4.85 (2H, m), 5.12 (1H, d, J=4.6 Hz), 6.11, 5.58 (2H, ABq, J=14.2 Hz), 5.94 (1H, m), 6.94 (2H, d, J=8.6 Hz), 7.38 (2H, d, J=8.6 Hz), 7.95 (1H, dd, J=7.8 Hz, 6.2 Hz), 8.86 (1H, d, J=6.2 Hz), 9.01 (1H, d, J=7.8 Hz), 9.07 (1H, s), 9.74 (1H, d, J=8.6 Hz), 12.6 (1H, s). IR (Nujol) cm$^{-1}$: 1785, 1610, 1540, 1510, 1375.

(2) Compound 34d (1.1 g, 1.04 mmol) was dissolved in CH$_2$Cl$_2$ 18 ml and MeNO$_2$ 10 ml and the mixture was ice-cooled. Anisole (1.36 ml, 12 eq.) and TiCl$_4$ (1.15 ml, 10 eq.) were added thereto at 5° C. and the mixture was stirred for 1 hr. The reaction mixture was poured into 0.25N HCl 25 ml and Et$_2$O 50 ml with stirring. The water layer was separated, washed with Et$_2$O 300 ml, and purified with HP-20. The eluted portion was lyophilized to give compound 35d (0.17 g, 23%).

$^1$H-NMR (D$_2$O) δ: 2.38 (2H, m), 3.13 (2H, t, J=8.2 Hz), 3.30, 3.63 (2H, ABq, J=18.0 Hz), 4.70 (6H, m), 5.23 (1H, d, J=5.0 Hz), 5.62, 5.90 (2H, ABq, J=14.3 Hz), 5.85 (1H, d, J=5.0 Hz), 7.88 (1H, dd, J=8.2 Hz, 6.6 Hz), 8.80 (1H, d, J=8.2 Hz), 8.84 (1H, d, J=6.6 Hz), 8.88 (1H, s) Elementary Analysis as C$_{23}$H$_{25}$N$_{10}$O$_5$S$_2$F.1.1 HCl.4.5H$_2$O; calc.: C, 38.06; H, 4.87; N, 19.30; S, 8.84; F, 2.62; Cl, 5.37; found: C, 38.02; H, 4.86; N, 19.16; S, 8.65; F, 2.41; Cl, 5.46.

Reaction schemes of Example 6-1 to Example 6-4 are shown below.

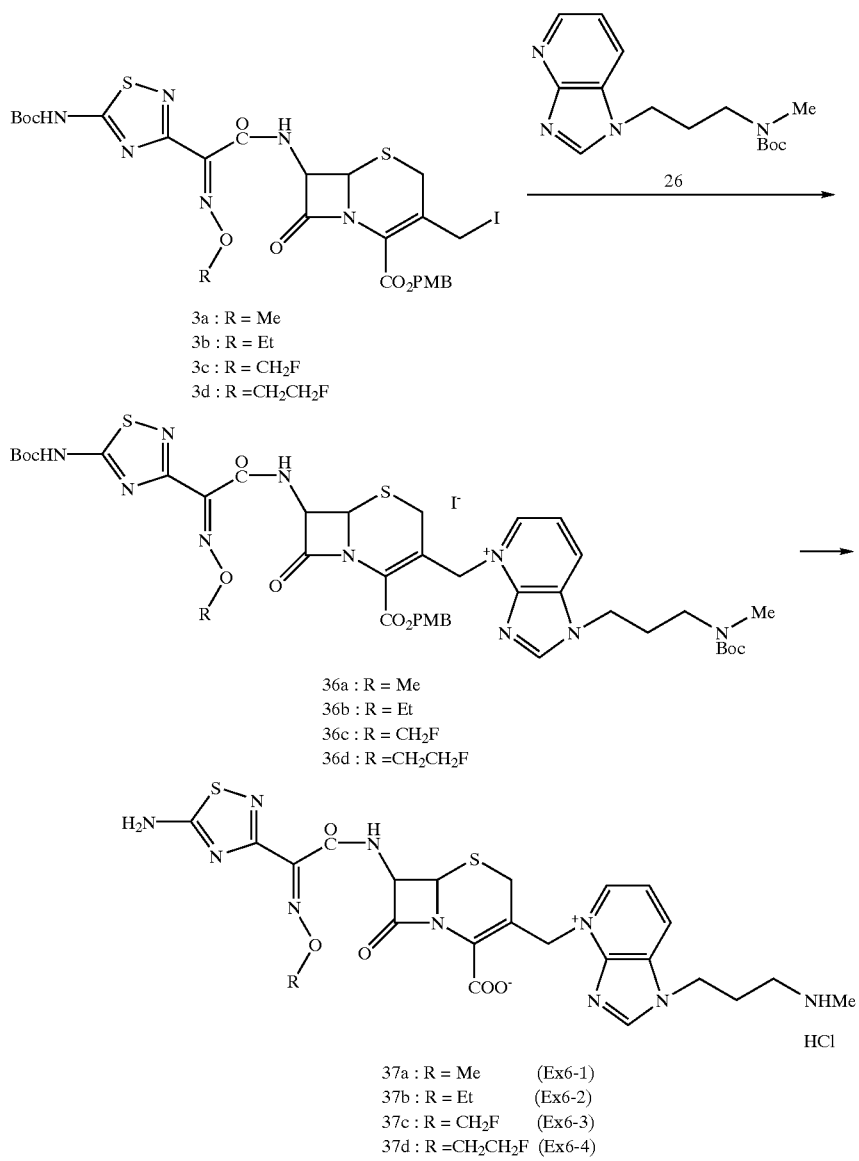

3a : R = Me
3b : R = Et
3c : R = CH₂F
3d : R = CH₂CH₂F

36a : R = Me
36b : R = Et
36c : R = CH₂F
36d : R = CH₂CH₂F

37a : R = Me (Ex6-1)
37b : R = Et (Ex6-2)
37c : R = CH₂F (Ex6-3)
37d : R = CH₂CH₂F (Ex6-4)

EXAMPLE 6-1

(1) To a solution of compound 26 (0.59 g, 2.03 mmol) in MeCN 15 ml, was added compound 3a (1.66 g, 1.1 eq.) under stirring at room temperature and the mixture was further stirred for 1.5 hr. Et₂O 80 ml was added to the reaction mixture, then the precipitate was filtered to give compound 36a (1.67 g, yield:79%).

$^1$H-NMR (d$_6$-DMSO) δ: 1.36 (9H, s), 1.50 (9H, s), 2.10 (2H, m), 2.80 (2H, s), 3.23 (2H, m), 3.45 (2H, m), 3.77 (3H, s), 3.93 (3H, s), 4.45 (2H, m), 5.09 (1H, d, J=5.2 Hz), 5.29 (2H, s), 5.59, 6.09 (2H, ABq, J=14.6 Hz), 5.93 (1H, dd, J=8.6 Hz, 5.2 Hz), 6.93 (2H, d, J=8.6 Hz), 7.38 (2H, d, J=8.6 Hz), 7.95 (1H, dd, J=7.8 Hz, 6.2 Hz), 8.86 (1H, d, J=6.2 Hz), 9.04 (1H, d, J=7.8 Hz), 9.10 (1H, s), 9.74 (1H, d, J=8.6 Hz), 12.6 (1H, s). IR (Nujol) cm$^{-1}$: 1770, 1710, 1680, 1550, 1460, 1375.

(2) Compound 36a (1.65 g, 1.59 mmol) was dissolved in CH₂Cl₂ 30 ml and MeNO₂ 8 ml and the mixture was cooled to −20° C. Anisole (2.08 ml, 12 eq.) and an AlCl₃—MeNO₂ solution (1M, 15.9 ml, 10 eq.) were added thereto and the mixture was stirred at −5° C. for 1 hr. The reaction mixture was poured into a mixture of 0.25N HCl 35 ml and Et₂O 70 ml with stirring. The water layer was separated, washed with Et₂O 120 ml, and purified with HP-20. The eluted portion was lyophilized to give compound 37a (0.43 g, 39%).

$^1$H-NMR (D₂O) δ: 2.40 (2H, m), 2.73 (3H, s), 317 (2H, t, J=8.2 Hz), 3.30, 3.64(2H, ABq, J=17.9 Hz), 4.05 (3H, s), 4.64 (2H, t, J=7.0 Hz), 5.22 (1H, d, J=4.8 Hz), 5.62, 5.89 (2H, ABq, J=14.6 Hz), 5.85 (1H, d, J=4.8 Hz), 7.88 (1H, dd, J=8.6 Hz, 6.6 Hz), 8.80 (1H, d, J=8.6 Hz), 8.84 (1H, d, J=6.6 Hz), 8.88 (1H, s). IR (KBr) cm$^{-1}$: 1773, 1669, 1611, 1525, 1389. Elementary Analysis as C₂₃H₂₆N₁₀O₅S₂.1.1HCl.3.9H₂O; calc.: C, 39.63; H, 5.05; N, 20.10; S, 9.20; Cl, 5.59; found: C, 39.68; H, 5.07; N, 20.31; S, 9.27; Cl, 5.40.

EXAMPLE 6-2

(1) To a solution of compound 26 (0.54 g, 1.86 mmol) in DMF 8 ml, was added compound 3b (1.69 g, 1.2 eq.) under stirring and ice-cooling and the mixture was stirred at room temperature for 1 hr. The reaction mixture was slowly added to $Et_2O$ 300 ml under stirring, then the precipitate was filtered to give compound 36b (1.90 g, 96%).

$^1$H-NMR ($d_6$-DMSO) δ: 1.23 (3H, t, J=7.0 Hz), 1.36 (9H, s), 1.51 (9H, s), 2.18 (2H, m), 2.80 (3H, s), 3.45 (2H, m), 3.77 (3H, s), 4.20 (2H, q, J=7.0 Hz), 4.47 (2H, m), 5.10 (1H, d, J=5.2 Hz), 5.29 (2H, s), 6.10, 5.59 (2H, ABq, J=14.3 Hz), 5.95 (1H, dd, J=8.4 Hz, 5.2 Hz), 6.93 (2H, d, J=8.8 Hz), 7.39 (2H, d, J=8.8 Hz), 7.95 (1H, dd, J=7.6 Hz, 6.4 Hz), 8.86 (1H, d, J=6.4 Hz), 9.04 (1H, d, J=7.6 Hz), 9.10 (1H, s), 9.67 (1H, s), 12.59 (1H, s). IR (Nujol) $cm^{-1}$: 1790, 1715, 1545, 1460, 1380.

(2) Compound 36b (1.89 g, 1.8 mmol) was dissolved in $CH_2Cl_2$ 36 ml and $MeNO_2$ 12 ml and the mixture was cooled to −20° C. Anisole (2.35 ml, 12 eq.) and an $AlCl_3$—$MeNO_2$ solution (1M, 18 ml, 10 eq.) were added thereto and the mixture was stirred at −5° C. for 1 hr. The reaction mixture was poured into a mixture of 0.25N HCl 80 ml and $Et_2O$ 160 ml, then the water layer was separated, washed with $Et_2O$ 120 ml, and purified with HP-20. The eluted portion was lyophilized to give compound 37b (0.40 g, 31%).

$^1$H-NMR ($D_2O$) δ: 1.31 (3H, t, J=7.2 Hz), 2.41 (2H, m), 2.73 (3H, s), 3.17 (2H, t, J=8.4 Hz), 3.31, 3.64 (2H, ABq, J=18.2 Hz), 4.32 (2H, q, J=7.2 Hz), 4.64 (2H, t, J=7.5 Hz), 5.24 (1H, d, J=5.1 Hz), 5.64, 5.90 (2H, ABq, J=14.7 Hz), 5.85 (1H, d, J=5.1 Hz), 7.89 (1H, dd, J=8.4 Hz, 6.3 Hz), 8.80 (1H, d, J=8.4 Hz), 8.85 (1H, d, J=6.3 Hz), 8.88 (1H, s). IR (KBr) $cm^{-1}$: 1774, 1616, 1525, 1387. Elementary Analysis as $C_{24}H_{28}N_{10}O_5S_2 \cdot 1.3HCl \cdot 4.1H_2O$; calc.: C, 39.93; H, 5.24; N, 19.40; S, 8.88; Cl, 6.38; found: C, 39.90; H, 5.15; N, 19.37; S, 8.84; Cl, 6.59.

EXAMPLE 6-3

(1) To a solution of compound 26 (0.63 g, 2.17 mmol) in DMF 8 ml, was added compound 3c (1.99 g, 1.2 eq.) under stirring and ice-cooling and the mixture was stirred at room temperature for 1 hr. The reaction mixture was slowly added to $Et_2O$ 500 ml under stirring, then the precipitate was filtered to give compound 36c (2.42 g).

$^1$H-NMR (DMSO-d6) δ: 1.36 (9H, s), 1.51 (9H, s), 2.18 (2H, m), 2.80 (3H, s), 3.30 (2H, m), 3.50 (2H, m), 3.77 (3H, s), 4.48 (2H, t, J=7.8 Hz), 5.13 (1H, d, J=4.9 Hz), 5.29 (2H, s), 6.11, 5.60 (2H, ABq, J=14.3 Hz), 5.81 (2H, d, J=55.3 Hz), 5.95 (1H, m), 6.93 (2H, d, J=8.8 Hz), 7.38 (2H, d, J=8.8 Hz), 7.96 (1H, dd, J=8.0 Hz, 6.0 Hz), 8.87 (1H, d, J=6.0 Hz), 9.05 (1H, d, J=8.0 Hz), 9.11 (1H, s), 9.87(1H, s), 12.7 (1H, s). IR (Nujol) $cm^{-1}$: 1785, 1710, 1545, 1460, 1245.

(2) Compound 36c (2.37 g, 2.25 mmol) was dissolved into $CH_2Cl_2$ 40 ml and $MeNO_2$ 20 ml and the mixture was ice-cooled. Anisole (2.94 ml, 12 eq.) and $TiCl_4$ (2.47 ml, 10 eq.) were added thereto and the mixture was stirred at 5° C. for 1 hr. The reaction mixture was poured into 0.25N HCl 120 ml and $Et_2O$ 240 ml, then the water layer was separated, washed with $Et_2O$ 300 ml, and purified with HP-20. The eluted portion was lyophilized to give hydrochloride of compound 37c (0.50 g, yield: 31%).

$^1$H-NMR ($D_2O$) δ: 2.40 (2H, m), 2.73 (3H, s), 317 (2H, t, J=8.2 Hz), 3.29, 3.64 (2H, ABq, J=18.0 Hz), 4.63 (2H, t, J=7.2 Hz), 5.24 (1H, d, J=4.6 Hz), 5.63, 5.90 (2H, ABq, J=14.2 Hz), 5.82 (2H, d, J=54.2 Hz), 5.86 (1H, d, J=4.6 Hz), 7.87 (1H, dd, J=8.2 Hz, 6.2 Hz), 8.79 (1H, d, J=8.2 Hz), 8.85 (1H, d, J=6.2 Hz), 8.87 (1H, s). IR (KBr) $cm^{-1}$: 1774, 1671, 1617, 1525, 1393. Elementary Analysis as $C_{23}H_{25}N_{10}O_5S_2F \cdot 1.4HCl \cdot 4.1H_2O$; calc.: C, 37.87; H, 4.78; N, 19.20; S, 8.79; F, 2.60; Cl, 6.80; found: C, 37.82; H, 4.76; N, 19.35; S, 8.60; F, 2.80; Cl, 6.66.

EXAMPLE 6-4

(1) To a solution of compound 26 (0.66 g, 2.27 mmol) in MeCN 5 ml, was added a solution of compound 3d (2.29 g, 1.3 eq.) in MeCN 10 ml at room temperature under stirring and the mixture was stirred for 1.5 hr. The reaction mixture was concentrated under reduced pressure and $Et_2O$ 70 ml was added to the residue, followed by filtering to give compound 36d (2.65 g) as powder.

$^1$H-NMR (DMSO-d6) δ: 1.36 (9H, s), 1.50 (9H, s), 2.15 (2H, m), 2.80 (3H, s), 3.23 (2H, m), 3.45 (2H, m), 3.77 (3H, s), 4.35 (2H, m), 4.50 (4H, m), 5.09 (1H, d, J=5.2 Hz), 5.29 (2H, s), 6.11, 5.59 (2H, ABq, J=13.9 Hz), 5.95 (1H, dd, J=8.6 Hz, 5.2 Hz), 6.94 (2H, d, J=8.6 Hz), 7.38 (2H, d, J=8.6 Hz), 7.96 (1H, dd, J=8.2 Hz, 5.8 Hz), 8.86 (1H, d, J=5.8 Hz), 9.04 (1H, d, J=8.2 Hz), 9.10 (1H, s), 9.74 (1H, d, J=8.6 Hz), 12.62 (1H, s). IR (Nujol) $cm^{-1}$: 1782, 1710, 1680, 1545, 1515, 1460.

(2) Compound 36d (2.65 g, 2.48 mmol) was dissolved in $CH_2Cl_2$ 45 ml and $MeNO_2$ 20 ml and the mixture was ice-cooled. Anisole (3.24 ml, 12 eq.) and $TiCl_4$ (2.73 ml, 10 eq.) were added thereto and the mixture was stirred at 5° C. for 1 hr. The reaction mixture was poured into 0.25N HCl 60 ml and $Et_2O$ 120 ml under stirring. The water layer was separated, washed with $Et_2O$ 300 ml, and purified with HP-20. The eluted portion was lyophilized to give compound 37d (0.48 g, 26%).

$^1$H-NMR ($D_2O$) δ: 2.43 (2H, m), 2.75 (3H, s), 319 (2H, t, J=8.4 Hz), 3.32, 3.65 (2H, ABq, J=18.0 Hz), 4.66 (6H, m), 5.26 (1H, d, J=5.1 Hz), 5.65, 5.92 (2H, ABq, J=14.6 Hz), 5.87 (1H, d, J=5.1 Hz), 7.90 (1H, dd, J=8.4 Hz, 6.3 Hz), 8.81 (1H, d, J=8.4 Hz), 8.87 (1H, d, J=6.3 Hz), 8.89 (1H, s). IR (KBr) $cm^{-1}$: 1774, 1671, 1615, 1526, 1387. Elementary Analysis as $C_{24}H_{27}N_{10}O_5S_2F \cdot 1.1HCl \cdot 4.0H_2O$; calc.: C, 39.44; H, 4.99; N, 19.17; S, 8.77; F, 2.60; Cl, 5.34; found: C, 39.46; H, 5.02; N, 19.48; S, 8.71; F, 2.56; Cl, 5.36.

EXAMPLE 7

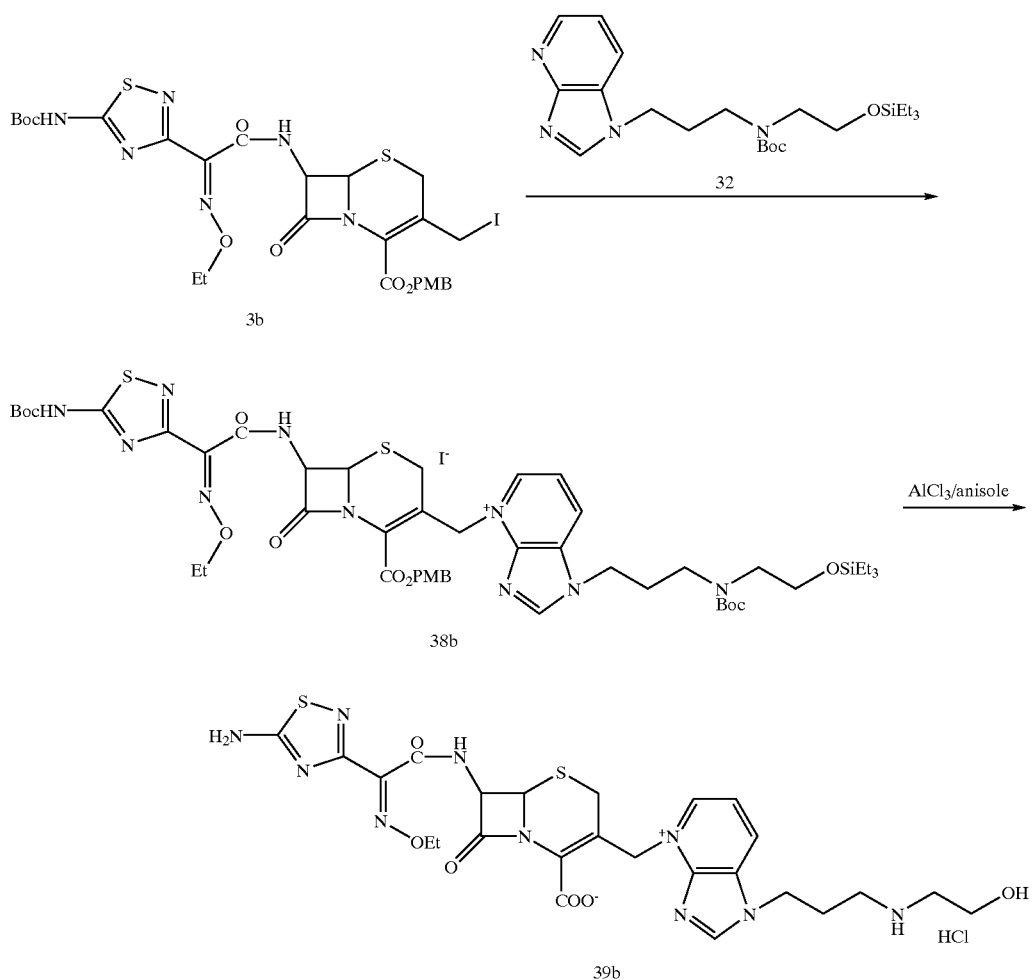

(1) To a solution of compound 32 (0.78 g, 1.79 mmol) in MeCN 17 ml, was added compound 3b (1.50 g, 1.1 eq.) under stirring at room temperature and the mixture was stirred for 1.5 hr. The reaction mixture was concentrated under reduced pressure and Et$_2$O 80 ml was added to the residue, followed by filtration to give compound 38b (1.77 g, 83%) as powder.

$^1$H-NMR (d$_6$-DMSO) δ: 0.54 (6H, q, J=8.1 Hz), 0.89 (9H, t, J=8.1 Hz), 1.24 (3H, t, J=6.9 Hz), 1.38 (9H, s), 1.51 (9H, s), 2.10 (2H, m), 3.25 (8H, m), 3.60 (2H, m), 3.76 (3H, s), 4.20 (2H, q, J=6.9 Hz), 4.45 (2H, m), 5.10 (1H, d, J=4.8 Hz), 5.29 (2H, s), 5.59, 6.10 (2H, ABq, J=14.4 Hz), 5.94 (1H, dd, J=8.4 Hz, 4.8 Hz), 6.94 (2H, d, J=8.7 Hz), 7.38 (2H, J=8.7 Hz), 7.96 (1H, dd, J=9.0 Hz, 5.4 Hz), 8.86 (1H, d, J=5.4 Hz), 9.04 (1H, d, J=9.0 Hz), 9.10 (1H, s), 9.67 (1H, d, J=8.4 Hz), 12.59 (1H, s). IR (Nujol) cm$^{-1}$: 1770, 1710, 1680, 1540, 1455, 1370.

(2) Compound 38b (1.75 g, 1.47 mmol) was dissolved in CH$_2$Cl$_2$ 28 ml and MeNO$_2$ 7 ml and the mixture was cooled to −20° C. Anisole (1.91 ml, 12 eq.) and an AlCl$_3$—MeNO$_2$ solution (1M, 14.7 ml, 10 eq.) were added thereto and the mixture was stirred at −5° C. for 1 hr. The reaction mixture was poured into a mixture of 0.25N HCl 35 ml and Et$_2$O 70 ml, then the water layer was separated, washed with Et$_2$O 120 ml, and purified with HP-20. The eluted portion was lyophilized to give compound 39b (0.13 g, 12%).

$^1$H-NMR (D$_2$O) δ: 1.30 (3H, t, J=6.9 Hz), 2.42 (2H, m), 3.22 (4H, m), 3.31, 3.64 (2H, ABq, J=18.2 Hz), 3.83 (2H, t, J=5.4 Hz), 4.33 (2H, q, J=6.9 Hz), 4.65 (2H, t, J=6.6 Hz), 5.23 (1H, d, J=4.8 Hz), 5.62, 5.90 (2H, ABq, J=14.6 Hz), 5.86 (1H, d, J=4.8 Hz), 7.89 (1H, dd, J=8.1 Hz, 6.6 Hz), 8.80 (1H, d, J=8.1 Hz), 8.84 (1H, d, J=6.6 Hz), 8,88 (1H, s). IR (KBr) cm$^{-1}$: 1773, 1669, 1611, 1527, 1388. Elementary Analysis as C$_{25}$H$_{30}$N$_{10}$O$_6$S$_2$.1.1HCl.5.2H$_2$O; calc.: C, 39.27; H, 5.48; N, 18.32; S, 8.39; Cl, 5.10; found: C, 39.24; H, 5.59; N, 18.13; S, 8.39; Cl, 5.32.

Reaction schemes of Example 8-1 to Example 8-2 are shown below.

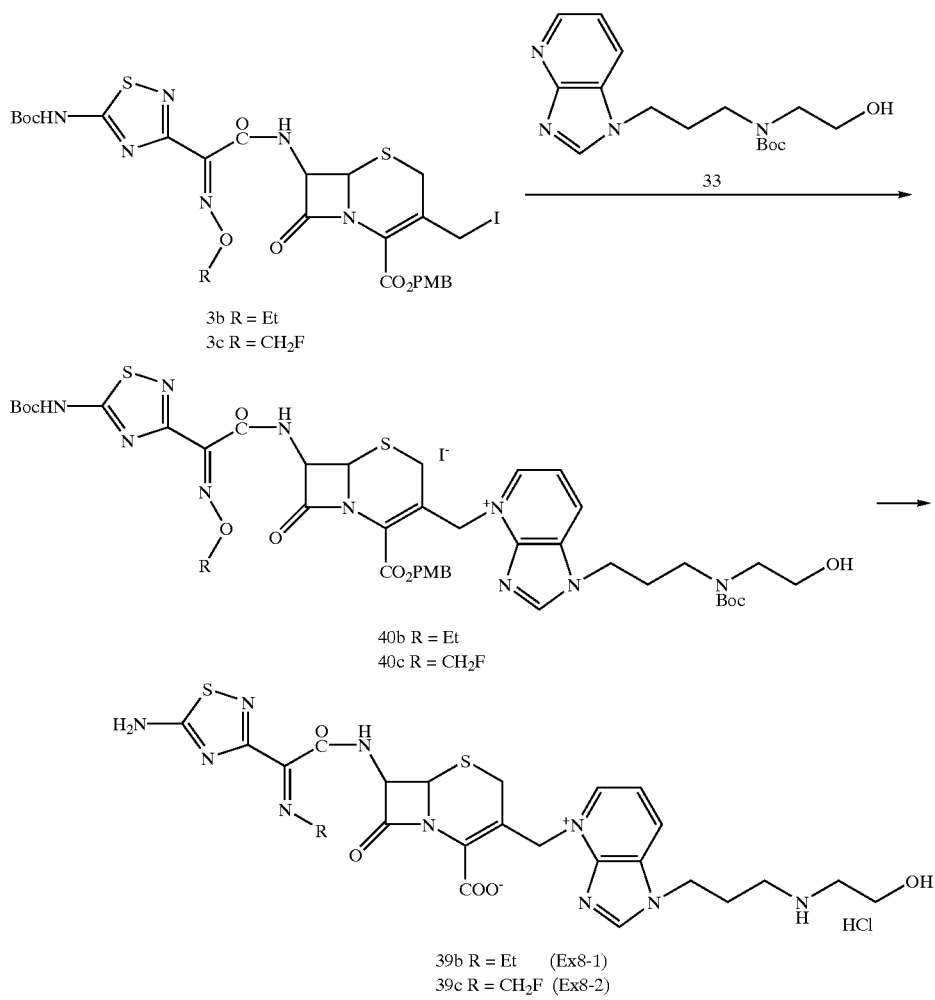

3b R = Et
3c R = CH₂F

40b R = Et
40c R = CH₂F

39b R = Et (Ex8-1)
39c R = CH₂F (Ex8-2)

EXAMPLE 8-1

(1) To a solution of compound 33 (1.9 g, 5.93 mmol) in MeCN 57 ml, was added a solution of compound 3b (4.95 g, 1.1 eq.) in MeCN 20 ml at room temperature and the mixture was stirred for 3 hr. The reaction mixture was concentrated under reduced pressure and the residue was added to (i-Pr)₂O 500 ml under stirring, then the precipitate was filtered to give compound 40b (6.07 g, 95%).

$^1$H-NMR (d$_6$-DMSO) δ: 1.24 (3H, t, J=6.8 Hz), 1.36 (9H, s), 1.51 (9H, s), 2.12 (2H, m), 3.35 (8H, m), 3.77 (3H, s), 4.20 (2H, q, J=6.8 Hz), 4.45 (2H, m), 5.10 (1H, d, J=4.9 Hz), 5.29 (2H, s), 5.59, 6.11 (2H, ABq, J=14.5 Hz), 5.94 (1H, dd, J=8.4 Hz, 4.9 Hz), 6.94 (2H, d, J=8.8 Hz), 7.38 (2H, d, J=8.8 Hz), 7.95(1H, dd, J=7.7 Hz, 6.2 Hz), 8.86 (1H, d, J=6.2 Hz), 9.03 (1H, d, J=7.7 Hz), 9.10 (1H, s), 9.66 (1H, d, J=8.4 Hz), 12.58 (1H, s). IR (Nujol) cm$^{-1}$: 1790, 1715, 1545, 1460, 1380.

(2) Compound 40b (6.05 g, 5.6 mmol) was dissolved in CH₂Cl₂ 120 ml and MeNO₂ 86 ml and the mixture was cooled to −20° C. Anisole (7.30 ml, 12 eq.) and an AlCl₃—MeNO₂ solution (1M, 56 ml, 10 eq.) were added thereto and the mixture was stirred at −5° C. for 1 hr. The reaction mixture was poured into 0.25N HCl 120 ml and Et₂O 240 ml under stirring. The water layer was separated, washed with Et₂O 120 ml, and purified with HP-20. The eluted portion was lyophilized to give compound 39b (1.81 g, 42%). The physical data was identical to that of Example 7.

EXAMPLE 8-2

(1) To a solution of compound 33 (0.70 g, 2.2 mmol) in MeCN 30 ml, was added a solution of compound 3c (1.85 g, 1.1 eq.) in MeCN 7 ml under stirring at room temperature, and the mixture was stirred for 3 hr. The reaction mixture was concentrated under reduced pressure and the residue was added to i-Pr₂O 200 ml under stirring, then the precipitate was filtered to give compound 40c (2.01 g, 84%).

$^1$H-NMR (d$_6$-DMSO) δ: 1.36 (9H, s), 1.51 (9H, s), 2.12 (2H, m), 3.35 (8H, m), 3.77 (3H, s), 4.47 (2H, m), 5.12 (1H, d, J=4.9 Hz), 5.29 (2H, s), 5.60, 6.11 (2H, ABq, J=14.3 Hz), 5.81 (2H, d, J=55.0 Hz), 5.96 (1H, m), 6.94 (2H, d, J=8.6 Hz), 7.38 (2H, d, J=8.6 Hz), 7.90 (1H, dd, J=8.2 Hz, 6.3 Hz), 8.86 (1H, d, J=6.3 Hz), 9.03 (1H, d, J=8.2 Hz), 9.10 (1H, s), 9.87 (1H, d, J=8.2 Hz), 12.65 (1H, s). IR (Nujol) cm$^{-1}$: 1785, 1710, 1545, 1460, 1245.

(2) Compound 40c (2.01 g, 1.86 mmol) was dissolved in CH₂Cl₂ 34 ml and MeNO₂ 17 ml and the mixture was ice-cooled. Anisole (2.4 ml, 12 eq.) and TiCl₄ (2.0 ml, 10 eq.) were added thereto and the mixture was stirred at 5° C. for 1 hr. The reaction mixture was poured into 0.25N HCl 40 ml and Et₂O 90 ml, then the water layer was separated, washed with Et₂O 300 ml, and purified with HP-20. The eluted portion was lyophilized to give compound 39c (0.49 g, 35%).

$^1$H-NMR (D₂O) δ: 2.44 (2H, m), 3.22 (4H, m), 3.30, 3.65 (2H, ABq, J=16.0 Hz), 3.84 (2H, t, J=7.1 Hz), 4.65 (2H, t,

J=5.7 Hz), 5.25 (1H, d, J=4.7 Hz), 5.63, 5.89 (2H, ABq, J=15.3 Hz), 5.84 (2H, d, J=54.2 Hz), 5.87 (1H, d, J=4.7 Hz), 7.89 (1H, dd, 8.2 Hz, 6.4 Hz), 8.80 (1H, d, J=8.2 Hz), 8.86 (1H, d, J=6.4 Hz), 8.88 (1H, s). IR (KBr) cm$^{-1}$: 1778, 1675, 1616, 1525, 1386. Elementary Analysis as $C_{24}H_{27}N_{10}O_6S_2F.1.1HCl.4.0H_2O$; calc.: C, 38.60; H, 4.87; N, 18.75; S, 8.59; F, 2.54; Cl, 5.22; found: C, 38.67; H, 4.84; N, 18.57; S, 8.24; F, 2.37; Cl, 5.13.

Reaction schemes of Example 9-1 to Example 9-2 are shown below.

(2) Compound 41b (1.31 g, 1.38 mmol) was dissolved in $CH_2Cl_2$ 28 ml and $MeNO_2$ 9 ml and the mixture was cooled to $-20°$ C. Aanisole (1.8 ml, 12 eq) and an $AlCl_3$—$MeNO_2$ solution (1M, 13.8 ml, 10 eq) were added thereto and the mixture was stirred at $-5°$ C. for 1 hr. The reaction mixture was poured into 0.25N HCl 70 ml and $Et_2O$ 140 ml with stirring. The water layer was separated, washed with $Et_2O$ 120 ml and purified with HP-20. The eluted portion was lyophilized to give compound 42b (0.45 g, 49%).

$^1$H-NMR ($D_2O$) δ: 1.29 (3H, t, J=7.0 Hz), 2.81 (3H, s), 3.28, 3.61 (2H, ABq, J=18.1 Hz), 4.31 (2H, q, J=7.0 Hz),

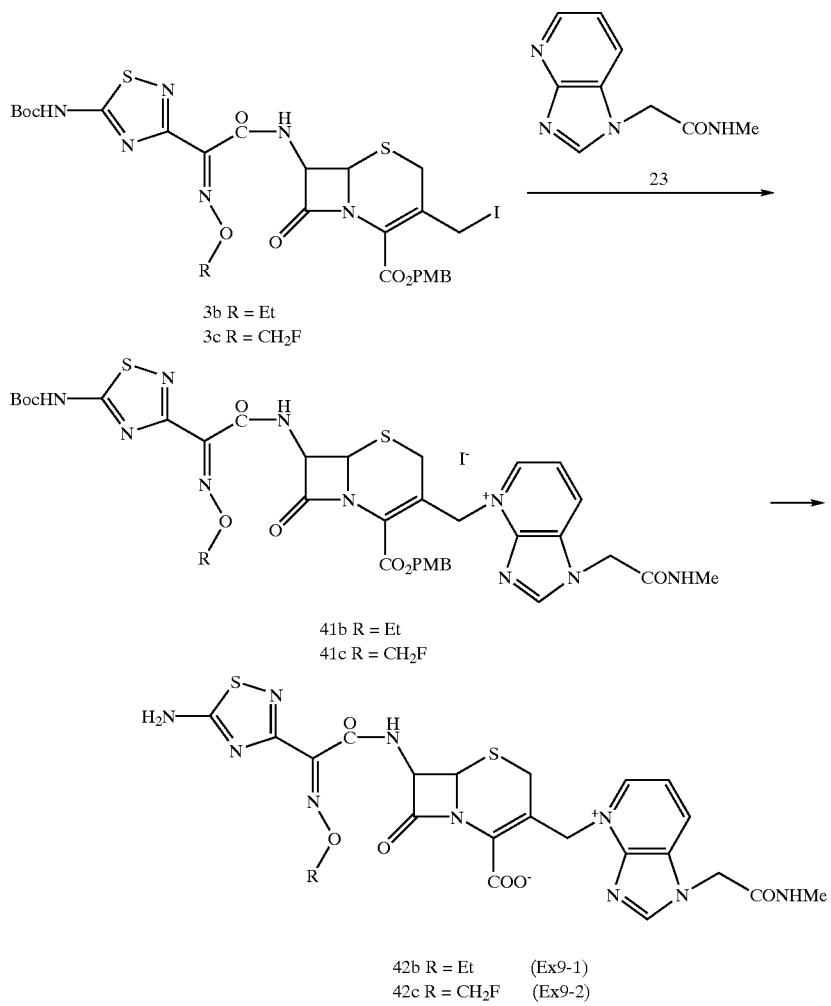

3b R = Et
3c R = CH$_2$F

41b R = Et
41c R = CH$_2$F

42b R = Et    (Ex9-1)
42c R = CH$_2$F  (Ex9-2)

EXAMPLE 9-1

(1) To a solution of compound 23 (247 mg, 1.3 mmol) in DMF 7 ml, was added compound 3b (1.28 g, 1.3 eq.) under stirring and ice-cooling and the mixture was stirred at room temperature for 1 hr. The reaction mixture was slowly added to $Et_2O$ 400 ml under stirring, then the precipitate was filtered to give compound 41b (1.32 g).

$^1$H-NMR (d$_6$-DMSO) δ: 1.24 (3H, t, J=7.0 Hz), 1.51 (9H, s), 2.68 (3H, d, J=4.6 Hz), 3.54 (2H, m), 3.77 (3H, s), 4.20 (2H, q, J=7.0 Hz), 5.15 (1H, d, J=5.0 Hz), 5.27 (2H, s), 5.59, 6.14 (2H, ABq, J=14.8 Hz), 5.93 (1H, dd, J=8.2 Hz, 5.0 Hz), 6.93 (2H, d, J=8.6 Hz), 7.37 (2H, d, J=8.6 Hz), 7.96 (1H, dd, J=9.0 Hz, 5.6 Hz), 8.38 (1H, d, J=9.0 Hz), 8.87 (1H, d, J=5.6 Hz), 9.00 (1H, s), 9.68 (1H, d, J=8.2 Hz), 12.59 (1H, s). IR (Nujol) cm$^{-1}$: 1785, 1715, 1680, 1550, 1460.

5.22 (1H, d, J=5.0 Hz), 5.34 (2H, s), 5.67, 5.91 (2H, ABq, J=14.8 Hz), 5.86 (1H, d, J=5.0 Hz), 7.88 (1H, dd, J=8.0 Hz, 6.2 Hz), 8.66 (1H, d, J=8.0 Hz), 8.83 (1H, s), 8.90 (1H, d, J=6.2 Hz). IR (KBr) cm$^{-1}$: 1773, 1673, 1613, 1385. Elementary Analysis as $C_{23}H_{24}N_{10}O_6S_2.3.7H_2O$; calc.: C, 41.40; H, 4.74; N, 20.99; S, 9.61; found: C, 41.37; H, 4.69; N, 21.34; S, 9.56.

EXAMPLE 9-2

(1) To a solution of compound 23 (476 mg, 2.5 mmol) in DMF 10 ml, was added compound 3c (2.29 g, 1.2 eq) under stirring and ice-cooling and the mixture was stirred at room temperature for 1 hr. The reaction mixture was slowly added to $Et_2O$ 500 ml, then the precipitate was filtered to give compound 41c (2.81 g).

$^1$H-NMR (d$_6$-DMSO) δ: 1.51 (9H, s), 2.68 (3H, d, J=4.2 Hz), 3.5 (2H, m), 3.77 (3H, s), 5.15 (1H, d, J=4.8 Hz), 5.27 (2H, s), 5.59, 6.14 (2H, ABq, J=15.0 Hz), 5.82 (2H, d, J=56.0 Hz), 5.96 (1H, m), 6.93 (2H, d, J=8.4 Hz), 7.37 (2H; d, J=8.4 Hz), 7.96 (1H, dd, J=9.0 Hz, 5.6 Hz), 8.37 (1H, d, J=5.6 Hz), 8.87 (1H, d, J=9.0 Hz), 8.90 (1H, d, J=8.2 Hz), 9.01 (1H, s), 12.67 (1H, s). IR (Nujol) cm$^{-1}$: 1780, 1705, 1660, 1455, 1370.

(2) Compound 41c (2.38 g, 2.5 mmol) was dissolved in CH$_2$Cl$_2$ 50 ml and MeNO$_2$ 25 ml and the mixture was ice-cooled. Anisole (3.26 ml, 12 eq) and TiCl$_4$ (2.75 ml, 10 eq) were added thereto and the mixture was stirred at 5° C. for 1 hr. The reaction mixture was poured into 0.25N HCl 200 ml and Et$_2$O 300 ml with stirring. The water layer was separated, washed with Et$_2$O 300 ml and purified with HP-20SS chromato. The eluted portion was lyophilized to give compound 42c (0.60 g, 36%).

$^1$H-NMR (D$_2$O) δ: 2.81 (3H, s), 3.26, 3.61 (2H, ABq, J=18.1 Hz), 5.23 (1H, d, J=4.8 Hz), 5.33 (2H, s), 5.67, 5.91 (2H, ABq, J=14.8 Hz), 5.82 (2H, d, J=53.4 Hz), 5.85 (1H, d, J=4.8 Hz), 7.87 (1H, dd, J=8.2 Hz, 5.8 Hz), 8.65 (1H, d, J=8.2 Hz), 8.82 (1H, s), 8.90 (1H, d, J=5.8 Hz). IR (KBr) cm$^{-1}$: 1774, 1675, 1613, 1527, 1387. Elementary Analysis as C$_{22}$H$_{21}$N$_{10}$O$_6$S$_2$F.3.2H$_2$O; calc.: C, 39.90; H, 4.17; N, 21.15; S, 9.68; F, 2.87; found: C, 39.91; H, 4.25; N, 21.32; S, 9.84; F, 2.68.

The compounds of Examples 10 to 33 shown below were synthesized by using materials obtained in Reference Examples 13 to 33.

EXAMPLE 10

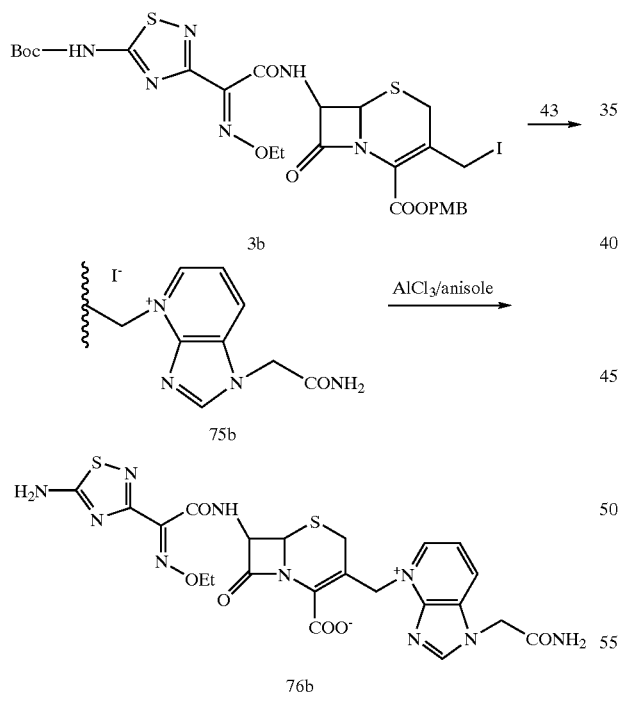

75b (1) To a solution of compound 43 (0.264 g, 1.5 mmol) of Reference Example 13 in DMF 7 ml, was dissolved a solution of compound 3b (1.48 g, 1.3 eq) in MeCN 4 ml under stirring and ice-cooling and the mixture was stirred at room temperature for 1.5 hr. From the reaction mixture, MeCN was evaporated under reduced pressure and the residue was slowly added to Et$_2$O 400 ml under stirring. The precipitate was filtered to give compound 75b (1.41 g, yield 100%).

$^1$H-NMR (DMSO-d6) δ: 1.24 (3H, t, J=7.2 Hz), 1.51 (9H, S), 3.77 (3H, S), 4.20 (2H, q, J=7.2 Hz), 5.13 (1H, d, J=5 Hz), 5.28 (2H, m), 5.58, 6.14 (2H, ABq, J=14.6 Hz), 5.93 (1H, dd, J=8.6 Hz, 5 Hz), 6.93 (2H, d, J=8.8 Hz), 7.34 (2H, d, J=8.8 Hz), 7.57 (1H, S), 7.88 (1H, S), 7.96 (2H, m), 8.88 (1H, m), 9.01 (1H, S), 9.68 (1H, d, J=8.6 Hz), 12.59 (1H, S). IR (CHCl$_3$) cm$^{-1}$: 3250, 1780, 1710, 1680, 1550, 1390.

(2) Compound 75b (1.40 g, 1.5 mmol) was dissolved in CH$_2$Cl$_2$ 30 ml and MeNO$_2$ 10 ml and the mixture was cooled to −20° C. with stirring. Anisole (1.95 ml, 12 eq) and an AlCl$_3$—MeNO$_2$ solution (1M, 15 ml, 10 eq.) were added thereto and the mixture was stirred at −5° C. for 30 min. The reaction mixture was poured into 0.25N HCl 70 ml and Et$_2$O 140 ml with stirring. The water layer was separated, washed with Et$_2$O 140 ml, and purified with HP-20. The eluted portion was lyophilized to give compound 76b (0.42 g, yield 43%).

$^1$H-NMR (D$_2$O) δ: 1.29 (3H, t, J=7 Hz), 3.28, 3.61 (2H, ABq, J=18 Hz), 4.31 (2H, q, J=7 Hz), 5.22 (1H, d, J=4.6 Hz), 5.40 (2H, S), 5.66, 5.91 (2H, ABq, J=14.6 Hz), 5.86 (1H, d, J=4.6 Hz), 7.89 (1H, dd, J=6.2 Hz, 8.4 Hz), 8.69 (1H, d, J=8.4 Hz), 8.83 (1H, S), 8.90 (1H, d, J=6.2 Hz). IR (KBr) cm$^{-1}$: 1770, 1684, 1613, 1525. Elementary Analysis as C$_{22}$H$_{22}$N$_{10}$O$_6$S$_2$.3.5H$_2$O; calc.: C, 40.67; H, 4.50; N, 21.56; S, 9.87; found: C, 40.66; H, 4.18; N, 21.39; S, 9.92.

EXAMPLE 11

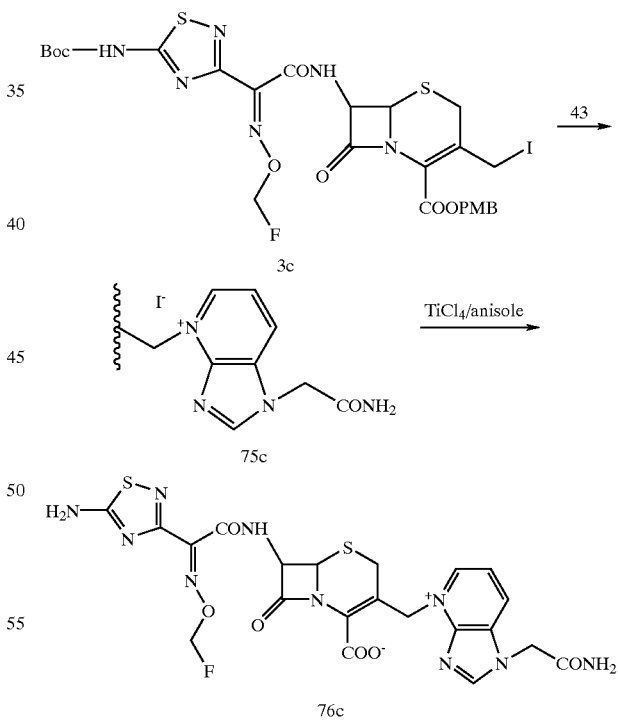

76c (1) To a solution of compound 43 (0.529 g, 3 mmol) of Reference Example 13 in DMF 14 ml, was added a solution of compound 3c (2.38 g, 1.2 eq) in MeCN 3 ml under stirring and ice-cooling and the mixture was stirred at room temperature for 2 hr. From the reaction mixture, MeCN was evaporated under reduced pressure and the residue was slowly added to Et$_2$O 600 ml. The precipitate was filtered to give compound 75c (2.64 g, yield 100%).

$^1$H-NMR (DMSO-d6) δ: 1.51 (9H, S), 3.77 (3H, S), 5.15 (1H, d, J=5 Hz), 5.26 (2H, m), 5.59, 6.12 (2H, ABq, J=14.5 Hz), 5.82 (2H, d, J=56.4 Hz), 6.93 (2H, d, J=8.6 Hz), 7.57 (1H, S), 7.93 (3H, m), 7.37 (2H, d, J=8.6 Hz), 8.88 (1H, m), 9.01 (1H, S), 9.89 (1H, d, J=8.6 Hz), 12.66 (1H, S). IR (CHCl$_3$) cm$^{-1}$: 1775, 1715, 1670, 1545, 1385.

(2) Compound 75c (2.63 g, 3.14 mmol) was dissolved in CH$_2$Cl$_2$ 60 ml and MeNO$_2$ 30 ml and the mixture was cooled under stirring. Anisole (4.09 ml, 12 eq) and TiCl$_4$ (3.45 ml, 10 eq) were added thereto and the mixture was stirred at 5° C. for 1.5 hr. The reaction mixture was poured into a mixture of 0.25N HCl 200 ml and Et$_2$O 280 ml with stirring. The water layer was separated, washed with Et$_2$O 280 ml, and purified with HP-20. The eluted portion was lyophilized to give compound 76c (0.50 g, yield 25%).

$^1$H-NMR (D$_2$O) δ: 3.26, 3.61 (2H, ABq, J=18.0 Hz), 5.23 (2H, d, J=5 Hz), 5.39 (2H, S), 5.65, 5.90 (2H, ABq, J=14.0 Hz), 5.81 (2H, d, J=53.6 Hz), 5.86 (1H, d, J=5 Hz), 7.87 (1H, dd, J=8.4 Hz, 6.2 Hz), 8.68 (1H, d, J=8.4 Hz), 8.82 (1H, S), 8.90 (1H, d, J=6.2 Hz). IR (KBr) cm$^{-1}$: 1770, 1684, 1614, 1525, 1487, 1463. Elementary Analysis as C$_{21}$H$_{19}$N$_{10}$O$_6$S$_2$F.3.6H$_2$O; calc.: C, 38.48; H, 4.03; N, 21.37; S, 9.78; F, 2.90; found: C, 38.46; H, 3.73; N, 21.16; S, 9.55; F, 2.74.

EXAMPLE 12

(1) Compound 44 (0.245 g, 1.2 mmol) of Reference Example 14 and compound 3b (1.18 g, 1.3 eq) were dissolved into DMF 8 ml and the mixture was stirred at room temperature for 1.5 hr. The reaction mixture was slowly added to Et$_2$O 300 ml, then the precipitate was filtered to give compound 77b (1.26 g, yield 100%).

$^1$H-NMR (DMSO-d6) δ: 1.24 (3H, t, J=7 Hz), 1.51 (9H, S), 2.91 (3H, S), 3.14 (3H, S), 3.77 (3H, S), 4.20 (2H, q, J=7 Hz), 5.14 (1H, d, J=5 Hz), 5.25, 5.31 (2H, ABq, J=12.2 Hz), 5.59 (4H, m), 5.93 (1H, dd, J=5 Hz), 5.93 (2H, d, J=8.4 Hz), 7.37 (2H, d, J=8.4 Hz), 7.95 (2H, m), 8.89 (1H, m), 8.93 (1H, S), 9.68 (1H, d, J=8.2 Hz), 12.59 (1H, S). IR (Nujol) cm$^{-1}$: 1785, 1715, 1660, 1545, 1460, 1379.

(2) Compound 77b (1.24 g, 1.29 mmol) was dissolved into CH$_2$Cl$_2$ 26 ml and CH$_3$NO$_2$ 8 ml and the mixture was cooled to −20° C. under stirring. Anisole (1.68 ml, 12 eq) and an AlCl$_3$/MeNO$_2$ solution(1M, 12.9 ml, 10 eq) were added thereto and the mixture was stirred at −5° C. for 30 min. The reaction mixture was poured into a mixture of 0.25N HCl 70 ml and Et$_2$O 140 ml with stirring. The water layer was separated, washed with Et$_2$O 140 ml, and purified with HP-20. Lyophilization gave compound 78b (0.37 g, yield 45%).

$^1$H-NMR (D$_2$O) δ: 1.29 (3H, t, J=7 Hz), 2.30 (3H, S), 3.21 (3H, S), 3.27, 3.61 (2H, ABq, J=19.6 Hz), 4.31 (2H, q, J=7 Hz), 5.22 (1H, d, J=5 Hz), 5.58 (2H, S), 5.66, 5.90 (2H, ABq, J=14.8 Hz), 5.86 (1H, d, J=5 Hz), 7.87 (1H, dd, J=8.2 Hz, 6 Hz), 8.61 (1H, d, J=8.2 Hz), 8.76 (1H, S), 8.89 (1H, d, J=6 Hz). IR (KBr) cm$^{-1}$: 1774, 1654, 1524, 1463, 1384. Elementary Analysis as C$_{24}$H$_{26}$N$_{10}$O$_6$S$_2$.4.2H$_2$O; calc.: C, 41.76; H, 5.02; N, 20.29; S, 9.29; found: C, 41.83; H, 4.94; N, 20.47; S, 9.47.

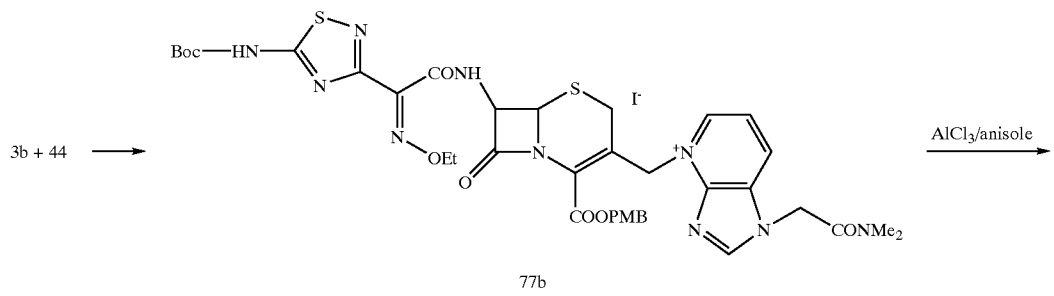

77b

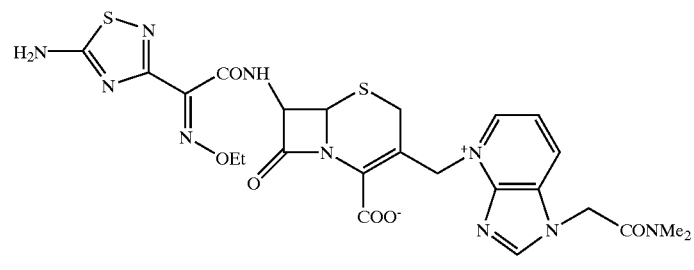

78b

EXAMPLE 13

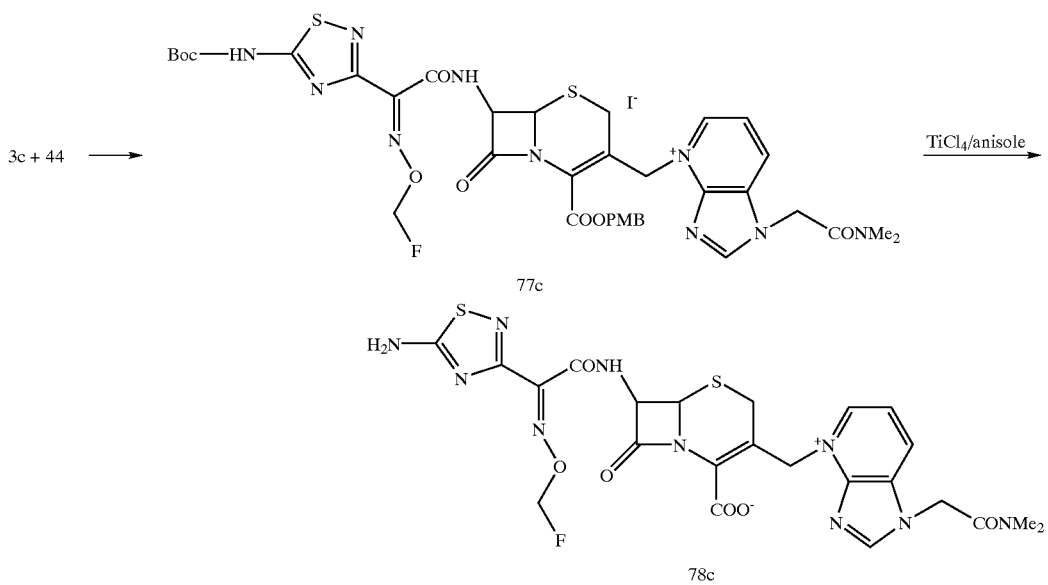

(1) Compound 44 (0.408 g, 2 mmol) of Reference Example 14 and compound 3c (1.83 g, 1.2 eq) were dissolved in DMF 13 ml and the mixture was stirred at room temperature for 1.5 hr. The reaction mixture was slowly added to Et$_2$O 500 ml, then the precipitate was filtered to give compound 77c (2.05 g, yield 100%).

$^1$H-NMR (DMSO-d6) δ: 1.52 (9H, S), 2.91 (3H, S), 3.15 (3H, S), 3.77 (3H, S), 5.16 (1H, d, J=4.8 Hz), 5.30 (2H, m), 6.00 (2H, m), 5.8 (2H, d, J=55 Hz), 6.93 (2H, d, J=8.6 Hz), 7.37 (2H, d, J=8.6 Hz), 7.96 (2H, m), 8.87 (1H, m), 8.93 (1H, S), 12.67 (1H, S). IR (Nujol) cm$^{-1}$: 1785, 1710, 1660, 1460, 1379.

(2) Compound 77c (2.03 g, 2 mmol) was dissolved in CH$_2$Cl$_2$ 40 ml and MeNO$_2$ 20 ml and the mixture was cooled under stirring. Anisole (2.61 ml, 12 eq) and TiCl$_4$ (2.20 ml, 10 eq) were added thereto and the mixture was stirred at 5° C. for 1.5 hr. The reaction mixture was poured into a mixture of 0.25N HCl 200 ml and Et$_2$O 300 ml with stirring. The water layer was separated, washed with Et$_2$O 300 ml, and purified with HP-20. Lyophilization gave compound 78c (0.27 g, yield 20%).

$^1$H-NMR (D$_2$O) δ: 3.0 (3H, S), 3.21 (3H, S), 3.26, 3.61 (2H, ABq, J=18.1 Hz), 5.23 (1H, d, J=4.8 Hz), 5.58 (2H, S), 5.81 (2H, d, J=54.2 Hz), 5.66, 5.90 (2H, ABq, J=14.8 Hz), 5.86 (1H, d, J=4.8 Hz), 7.86 (1H, dd, J=8.2 Hz, 6.2 Hz), 8.60 (1H, d, J=8.2 Hz), 8.76 (1H, S), 8.89 (1H, d, J=6.2 Hz). IR (KBr) cm$^{-1}$: 1773, 1651, 1527, 1491, 1463, 1394. Elementary Analysis as C$_{23}$H$_{23}$N$_{10}$O$_6$S$_2$F·4.1H$_2$O; calc.: C, 39.89; H, 4.54; N, 20.23; S, 9.26; F, 2.74; found: C, 39.93; H, 4.58; N, 20.40; S, 9.34; F, 2.68.

EXAMPLE 14

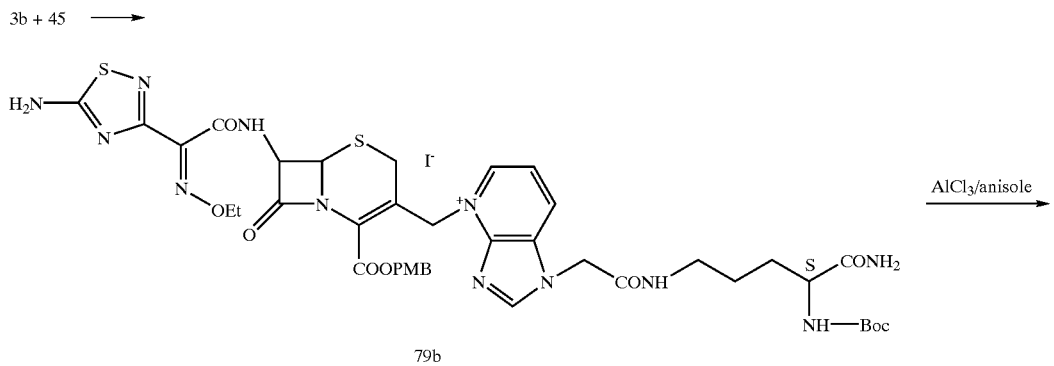

-continued

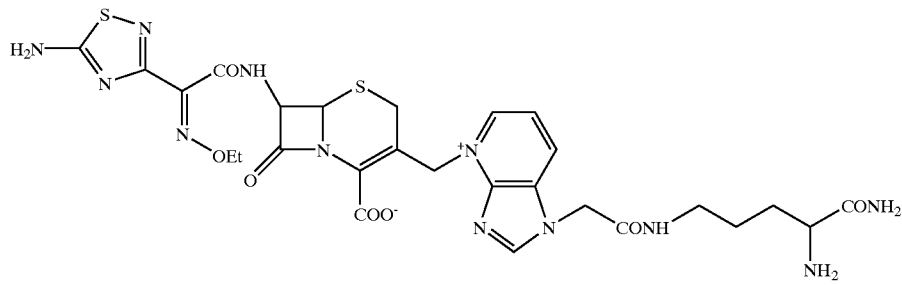

80b (1) Compound 45 (0.507 g, 1.3 mmol) of Reference Example 15 and compound 3b (1.28 g, 1.3 eq) were dissolved in DMF 8 ml and the mixture was stirred at 3° C. for 16 hr. The reaction mixture was added to 300 ml of Et$_2$O under stirring, then the precipitate was filtered to give compound 79b (1.16 g, yield 78%).

$^1$H-NMR (DMSOd6) δ: 1.25 (3H, t, J=7 Hz), 1.40 (9H, S), 1.51 (9H, S), 3.78 (3H, S), 4.22 (2H, q, t=7 Hz), 5.15 (1H, q, J=5 Hz), 5.60, 6.15 (2H, ABq, J=14.2 Hz), 5.95 (1H, dd, J=9 Hz, 5 Hz), 6.94 (2H, d, J=8.6 Hz), 7.38 (2H, d, J=8.6 Hz), 7.95 (1H, m), 8.88 (1H, m), 9.02 (1H, S), 9.68 (1H, d, J=9 Hz), 12.6 (1H, S). IR (CHCl$_3$) cm$^{-1}$: 1780, 1715, 1680, 1545, 1515.

(2) Compound 79b (1.16 g, 1.01 mmol) was dissolved in CH$_2$Cl$_2$ 20 ml and MeNO$_2$ 7 ml and the mixture was stirred under cooling. Anisole (1.32 ml, 12 eq) and an AlCl$_3$/MeNO$_2$ solution (1M, 10.1 ml,10 eq.) were added thereto and the mixture was stirred at 5° C. for 1.5 hr. The reaction mixture was poured into a mixture of 0.25N HCl 50 ml and Et$_2$O 100 ml with stirring. The water layer was separated, washed with Et$_2$O 100 ml, and purified with HP-20. Lyophilization gave compound 80b (0.12 g, yield 15%).

$^1$H-NMR (D$_2$O) δ: 1.27 (3H, t, J=7 Hz), 4.30 (2H, d, J=7 Hz), 5.20 (1H, d, J=4.6 Hz), 5.33 (2H, S), 5.63, 5.89 (2H, ABq, J=14.6 Hz), 5.84 (1H, d, J=4.6 Hz), 7.86 (1H, dd, J=8.2 Hz, 6.6 Hz), 8.64 (1H, d, J=8.2 Hz), 8.80 (1H, S), 8.88 (1H, d, J=6.6 Hz). IR (KBr) cm$^{-1}$: 1772, 1671, 1612, 1526, 1462, 1385. Elementary Analysis as C$_{27}$H$_{32}$N$_{12}$O$_7$S$_2$.4.6H$_2$O; calc.: C, 41.92; H, 4.07; N, 21.73; S, 8.29; found: C, 41.41; H, 5.09; N, 21.26; S, 8.47.

EXAMPLE 15

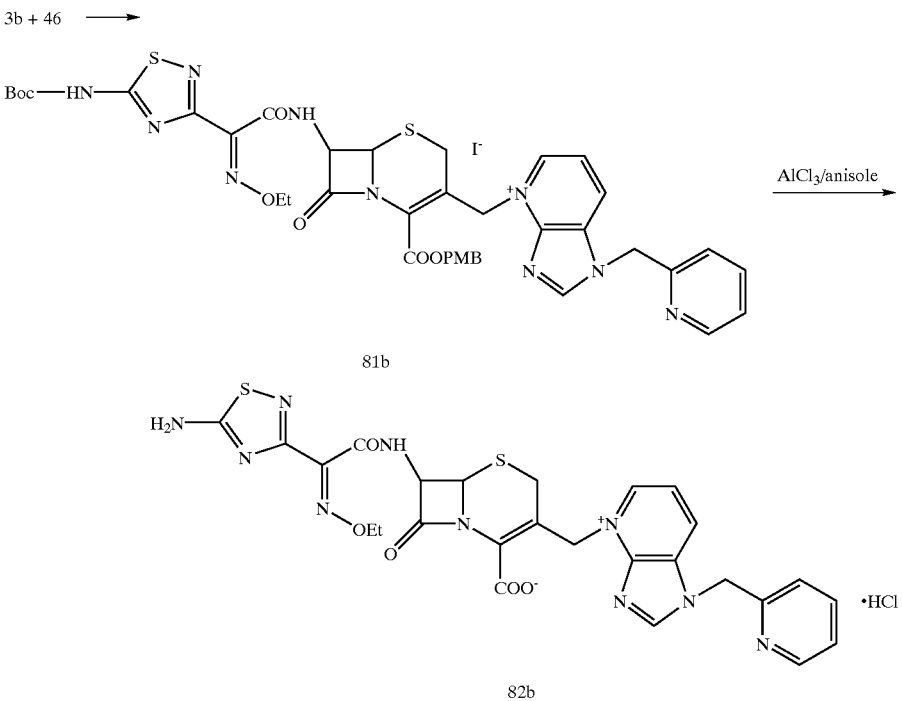

(1) Compound 46 (0.318 g, 1.51 mmol) of Reference Example 16 and compound 3b (1.38 g, 1.2 eq) were dissolved in DMF 7 ml and the mixture was stirred at room temperature for 45 min. The reaction mixture was added to Et$_2$O 300 ml under stirring, then the precipitate was filtered to give compound 81b (1.48 g, yield 100%).

$^1$H-NMR (DMSO-d6) δ: 1.24 (3H, t, J=7.2 Hz), 1.51 (9H, S), 3.76 (3H, S), 4.20 (2H, q, J=7.2 Hz), 5.11 (1H, d, J=5

Hz), 5.29 (2H, m), 5.60, 6.14 (2H, ABq, J=18.6 Hz), 6.0 (3H, m), 6.93 (2H, d, J=8.6 Hz), 7.38 (2H, d, J=8.6 Hz), 7.60 (1H, d, J=7.2 Hz), 7.89 (4H, m), 8.50 (1H, m), 8.9 (2H, m), 9.19 (1H, S), 9.67 (1H, d, J=8.2 Hz), 12.59 (1H, S). IR (Nujol) cm$^{-1}$: 1790, 1715, 1675, 1550, 1461, 1380.

(2) Compound 81b (1.46 g, 1.5 mmol) was dissolved in $CH_2Cl_2$ 30 ml and $MeNO_2$ 10 ml under stirring and cooling. Anisole 1.97 ml (12 eq) and an $AlCl_3/MeNO_2$ solution (1M, 15 ml, 10 eq) were added thereto and the mixture was stirred at 5° C. for 1.5 hr. The reaction mixture was poured into 0.25N HCl 70 ml and $Et_2O$ 140 ml with stirring. The water layer was separated, washed with $Et_2O$ 140 ml, and purified with HP-20. Lyophilization gave compound 82b (0.40 g, yield 38%).

$^1$H-NMR ($D_2O$) δ: 1.30 (3H, t, J=7.4 Hz), 3.32, 3.64 (2H, ABq, J=18.2 Hz), 4.32 (2H, q, J=7.4 Hz), 5.24 (1H, d, J=5 Hz), 5.69, 5.94 (2H, ABq, J=14.6 Hz), 5.86 (1H, d, J=5 Hz), 5.95 (2H, S), 7.59 (2H, m), 7.82 (1H, dd, J=8.2 Hz, 6.2 Hz), 8.06 (1H, m), 8.52 (1H, m), 8.55 (1H, d, J=8.2 Hz), 8.89 (1H, d, J=6.2 Hz), 8.98 (1H, S), IR (KBr) cm$^{-1}$: 1776, 1672, 1617, 1525, 1483, 1461, 1438. Elementary Analysis as $C_{26}H_{24}N_{10}O_5S_2$·0.3HCl, 3.6$H_2O$; calc.: C, 44.84; H, 4.56; N, 20.11; S, 9.21; Cl, 1.53; found: C, 44.80; H, 4.58; N, 20.13; S, 9.05; Cl, 1.69.

EXAMPLE 16

(1) To a solution of compound 46 (0.42 g, 2 mmol) of Reference Example 16 and compound 3c (1.83 g, 1.2 eq) in DMF 8 ml and the mixture was stirred at room temperature for 1 hr. The reaction mixture was added to $Et_2O$ 300 ml under stirring, then the precipitate was filtered to give compound 81c (2.12 g, yield 100%).

$^1$H-NMR (DMSO-d6) δ: 1.51 (9H, S), 3.76 (3H, S), 5.13 (1H, d, J=5.2 Hz), 5.28 (2H, m), 5.66 (3H, m), 5.92 (3H, m), 6.92 (2H, d, J=8.4 Hz), 7.37 (2H, d, J=8.4 Hz), 7.60 (1H, d, J=7.8 Hz), 7.93 (2H, m), 8.49 (1H, m), 8.84 (1H, d, J=6.8 Hz), 8.94 (1H, d, J=8.2 Hz), 9.20 (1H, S), 12.7 (1H, S). IR (Nujol) cm$^{-1}$: 1785, 1710, 1655, 1540, 1459, 1375.

(2) Compound 81c (2.11 g, 2.17 mmol) was dissolved in $CH_2Cl_2$ 40 ml and $MeNO_2$ 20 ml under stirring and cooling. Anisole (2.83 ml, 12 eq) and $TiCl_4$ (2.38 ml, 10 eq) were added thereto and the mixture was stirred at 5° C. for 1.5 hr. The reaction mixture was poured into 0.25N HCl 120 ml and $Et_2O$ 250 ml with stirring. The water layer was separated, washed with $Et_2O$ 250 ml, and purified with HP-20. Lyophilization gave compound 82c (0.34 g, yield 22%).

$^1$H-NMR ($D_2O$) δ: 3.31, 3.64 (2H, ABq, J=17.4 Hz), 5.24 (1H, d, J=5 Hz), 5.69, 5.94 (2H, ABq, J=14.6 Hz), 5.88 (1H, d, J=5 Hz), 5.83 (2H, d, J=58 Hz), 5.97 (1H, S), 7.62 (2H, m), 7.80 (1H, dd, J=8.2 Hz, 6.2 Hz), 8.11 (1H, m), 8.54 (2H, m), 8.88 (1H, d, J=6.2 Hz), 8.97 (1H, S). IR (KBr) cm$^{-1}$: 1775, 1676, 1616, 1525, 1484, 1462, 1438. Elementary Analysis as $C_{25}H_{21}N_{10}O_5S_2F$·0.6HCl, 3.6$H_2O$; calc.: C, 42.21; H, 4.08; N, 19.69; S, 9.01; F, 2.67; Cl, 2.99; found: C, 42.29; H, 4.13; N, 19.63; S, 8.79; F, 2.62; Cl, 2.95.

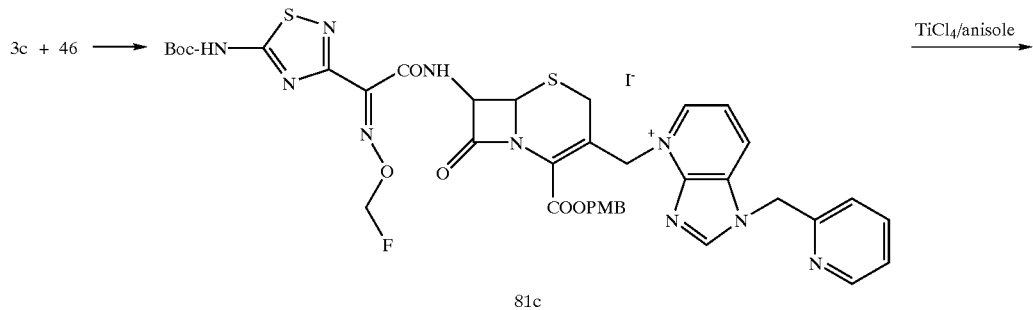

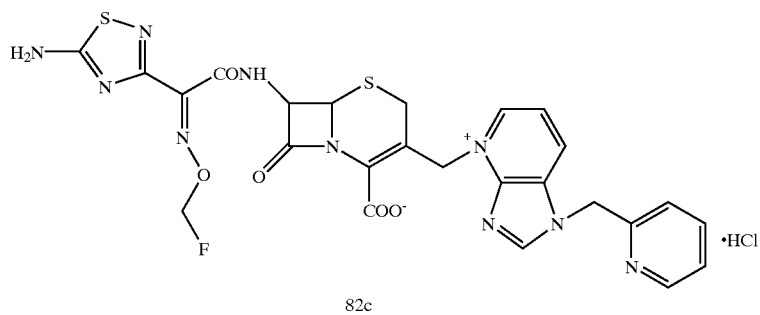

EXAMPLE 17

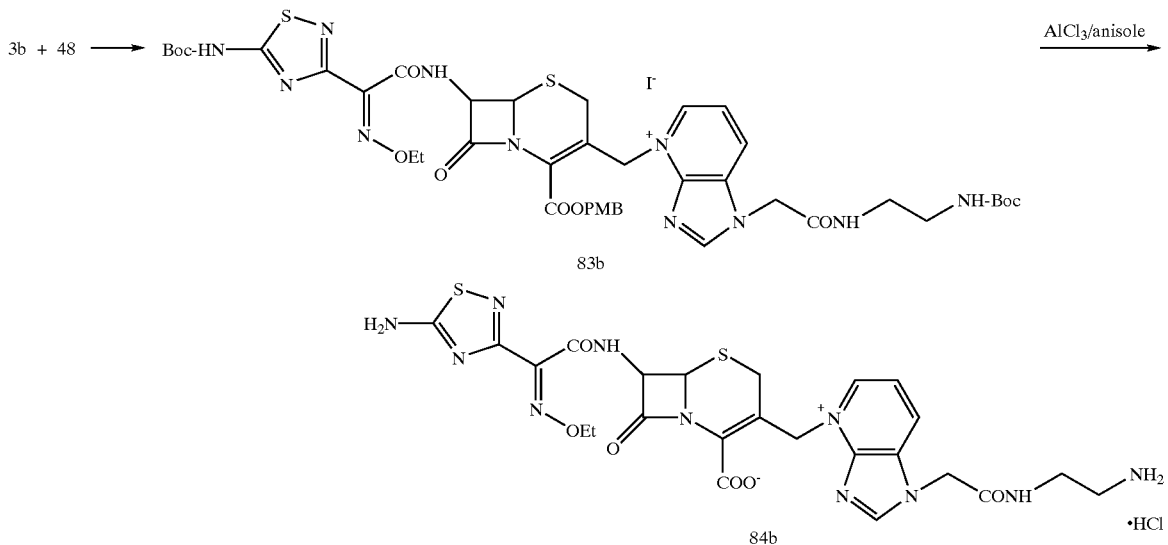

(1) Compound 48 (0.45 g, 1.71 mmol) of Reference Example 17 and compound 3b (1.69 g, 1.3 eq) of Example 10 were dissolved in DMF 7 ml and the mixture was stirred at room temperature for 1 hr. The reaction mixture was added to Et$_2$O 300 ml under stirring, then the precipitate was filtered to give compound 83b (2.03 g, yield 100%).

$^1$H-NMR (DMSO-d6) δ: 1.22 (9H, S), 1.23 (3H, t, J=7 Hz), 1.50 (9H, S), 3.77 (3H, S), 4.19 (2H, q, J=7 Hz), 4.52 (2H, m), 5.09 (1H, d, J=5.2 Hz), 5.29 (2H, m), 5.62, 6.09 (2H, ABq, J=14.6 Hz), 5.94 (1H, dd, J=8.2 Hz, 5.2 Hz), 6.95 (2H, d, J=9 Hz), 7.39 (2H, d, J=9 Hz), 7.98 (1H, m), 8.88 (1H, d, J=6.2 Hz), 8.96 (1H, d, J=8.2 Hz), 9.01 (1H, S), 9.65 (1H, d, J=8.2 Hz), 12.59 (1H, S). IR (CHCl$_3$) cm$^{-1}$: 1780, 1720, 1695, 1545, 1518, 1390.

(2) Compound 83b (1.83 g, 1.79 mmol) was dissolved in CH$_2$Cl$_2$ 36 ml and MeNO$_2$ 12 ml and the mixture was stirred under cooling. Anisole (2.34 ml, 12 eq) and 1 mol AlCl$_3$/MeNO$_2$ (17.9 ml,10 eq.) was added thereto under stirring at 5° C. for 1.5 hr. The reaction mixture was poured into a mixture of 0.25N HCl 80 ml and Et$_2$O 160 ml with stirring. The water layer was separated, washed with Et$_2$O 160 ml, and purified with HP-20. Lyophilization gave compound 84b (0.44 g, yield 35%).

$^1$H-NMR (D$_2$O) δ: 1.31 (3H, t, J=7.2 Hz), 3.32, 3.63 (2H, ABq, J=17.7 Hz), 3.67 (3H, m), 4.33 (2H, q, J=7.2 Hz), 4.91 (2H, t, J=6 Hz), 5.22 (1H, d, J=5 Hz), 5.64, 5.94 (2H, ABq, J=14.8 Hz), 5.85 (1H, d, J=5 Hz), 7.92 (1H, dd, J=8.2 Hz, 6.4 Hz), 8.86 (1H, d, J=8.2 Hz), 8.87 (1H, d, J=6.4 Hz), 8.92 (1H, S). IR (KBr) cm$^{-1}$: 1772, 1669, 1634, 1524, 1488, 1464. Elementary Analysis as C$_{22}$H$_{24}$N$_{10}$O$_5$S$_2$·1.4HCl, 3.9H$_2$O; calc.: C, 38.08; H, 4.82; N, 20.18; S, 9.24; Cl, 7.15; found: C, 38.04; H, 4.96; N, 19.80; S, 9.09; Cl, 7.11.

EXAMPLE 18

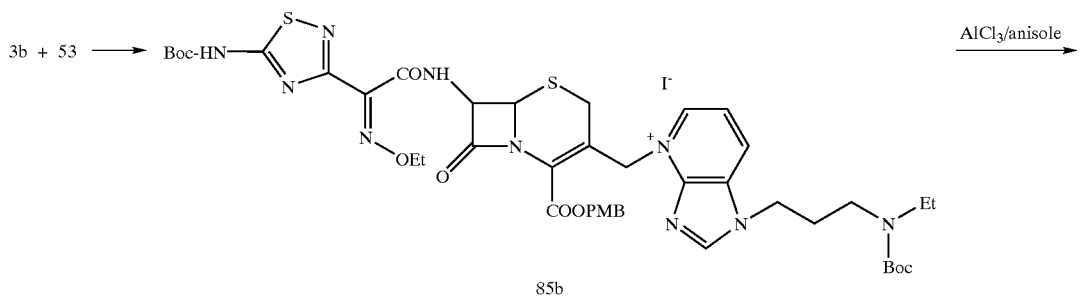

-continued

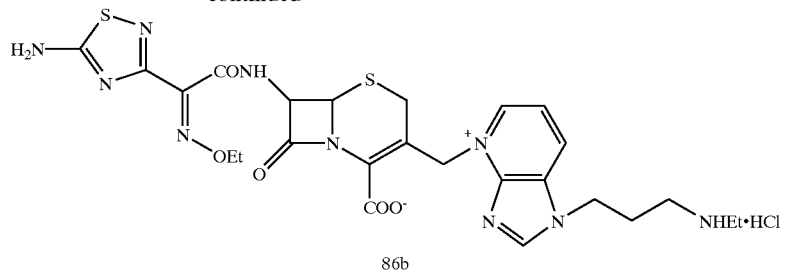

86b (1) To a solution of compound 53 (0.59 g, 1.94 mmol) of Reference Example 19 in MeCN 5 ml, was added a solution of compound 3b (1.62 g, 1.1 eq) in MeCN 10 ml under ice-cooling and the mixture was stirred at room temperature for 1.5 hr. From the reaction mixture was evaporated MeCN, then Et$_2$O 70 ml was added to the reside, then the precipitate was filtered to give compound 85b (1.69 g, yield 82%).

$^1$H-NMR (DMSO-d6) δ: 1.05 (3H, m), 1.23 (3H, t, J=6.6 Hz), 1.35 (9H, S), 1.51 (9H, S), 2.1 (2H, m), 3.19 (4H, m), 3.76 (3H, S), 4.20 (2H, q, J=7.2 Hz), 4.45 (2H, m), 5.1 (1H, d, J=4.8 Hz), 5.27, 5.31 (2H, ABq, J=12.3 Hz), 5.96 (1H, dd, J=8.7 Hz, 4.8 Hz), 5.59, 6.11 (2H, ABq, J=14.7 Hz), 6.93 (2H, d, J=8.7 Hz), 7.38 (2H, d, J=8.7 Hz), 7.96 (1H, m), 8.86 (1H, d, J=6.3 Hz), 9.03 (1H, d, J=8.1 Hz), 9.11 (1H, S), 9.68 (1H, d, J=8.7 Hz), 12.59 (1H, S). IR (Nujol) cm$^{-1}$: 1780, 1715, 1680, 1545, 1460, 1380.

(2) Compound 85b (1.67 g, 1.57 mmol) was dissolved in CH$_2$Cl$_2$ 30 ml and MeNO$_2$ 8 ml and the mixture was stirred under cooling. Anisole (2.05 ml, 12 eq) and 1 mol AlCl$_3$/MeNO$_2$ (15.7 ml, 10 eq) were added thereto and the mixture was stirred at 5° C. for 1.5 hr. The reaction mixture was poured in a mixture of 0.25N HCl 40 ml and Et$_2$O 80 ml with stirring. The water layer was separated, washed with Et$_2$O 80 ml, and purified with HP-20. Lyophilization gave compound 86b (0.40 g, yield 33%).

$^1$H-NMR (D$_2$O) δ: 1.29 (6H, m), 2.40 (2H, m), 312 (4H, m), 3.34, 3.65 (2H, ABq, J=18.4 Hz), 4.33 (2H, q, J=7.2 Hz), 4.64 (2H, t, J=7 Hz), 5.25 (1H, d, J=4.6 Hz), 5.70, 5.94 (2H, ABq, J=14.8 Hz), 5.88 (1H, d, J=4.6 Hz), 7.89 (1H, dd, J=8.2 Hz, 6.4 Hz), 8.81 (1H, d, J=8.2 Hz), 8.85 (1H, d, J=6.4 Hz), 8.89 (1H, S). IR (KBr) cm$^{-1}$: 1779, 1671, 1633, 1526, 1488, 1463. Elementary Analysis as: C$_{25}$H$_{30}$N$_{10}$O$_5$S$_2$.1.8HCl, 4.7H$_2$O; calc.: C, 39.24; H, 5.44; N, 18.31; S, 8.38; Cl, 8.34; found: C, 39.25; H, 5.20; N, 18.30; S, 8.43; Cl, 8.53.

EXAMPLE 19

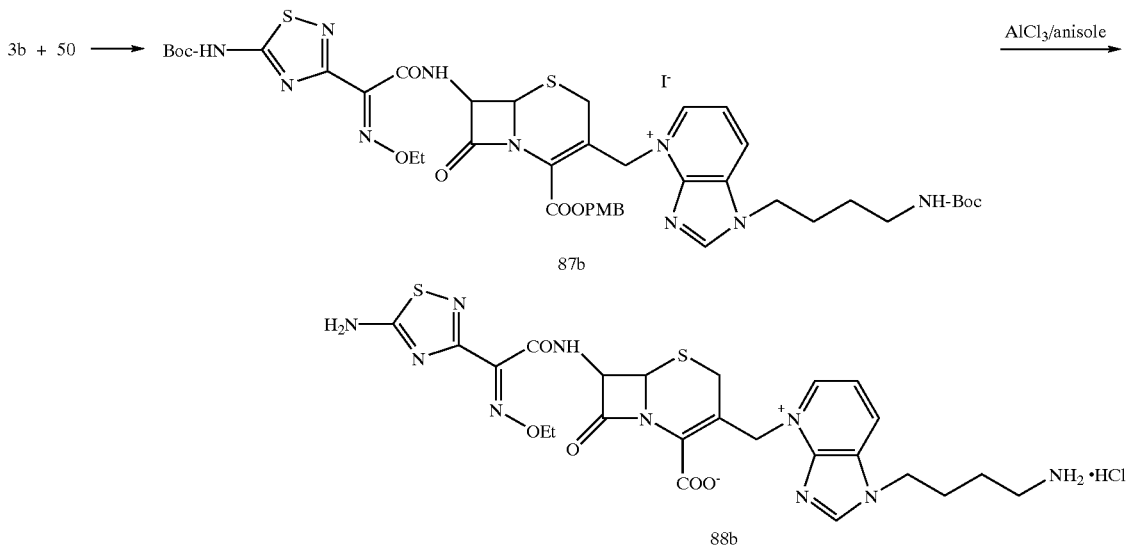

(1) Compound 50 (0.44 g, 1.52 mmol) of Reference Example 18 and compound 3b (1.38 g, 1.2 eq) were dissolved in DMF 7 ml and the mixture was stirred at room temperature for 1 hr. The reaction mixture was added to Et$_2$O 300 ml under stirring, then the precipitate was filtered to give compound 87b (1.51 g, yield 95%).

$^1$H-NMR (DMSO-d6) δ: 1.23 (3H, t, J=7.5 Hz), 1.36 (9H, S), 1.51 (9H, S), 1.85 (2H, m), 2.95 (2H, m), 3.77 (3H, S), 4.20 (2H, q, J=7.5 Hz), 4.50 (2H, m), 5.10 (1H, d, J=4.5 Hz), 5.27, 5.30 (2H, ABq, J=12.0 Hz), 5.57, 6.10 (2H, ABq, J=14.6 Hz), 5.95 (1H, dd, J=8.4 Hz, 4.5 Hz), 6.93 (2H, d, J=8.7 Hz), 7.38 (2H, d, J=8.7 Hz), 7.95 (1H, m), 8.85 (1H, d, J=6 Hz), 9.03 (1H, d, J=8.4 Hz), 9.07 (1H, S), 9.66 (1H, d, J=8.4 Hz), 12.6 (1H, S). IR (Nujol) cm$^{-1}$: 1790, 1710, 1690, 1545, 1515, 1460, 1380.

(2) Compound 87b (1.49 g, 1.42 mmol) was dissolved in CH$_2$Cl$_2$ 30 ml and MeNO$_2$ 10 ml and the mixture was stirred under cooling. Anisole (1.85 ml, 10 eq) and 1 mol AlCl$_3$/MeNO$_2$ (14.2 ml, 10 eq) were added thereto and the mixture was stirred at 5° C. for 1.5 hr. The reaction mixture was poured into a mixture of 0.25N HCl 60 ml and Et₂O 120 ml with stirring. The water layer was separated, washed with Et₂O 120 ml, and purified with HP-20. Lyophilization gave compound 88b (0.28 g, yield 27%).

¹H-NMR (D₂O) δ: 1.30 (3H, t, J=7 Hz), 1.75 (2H, m), 2.05 (2H, m), 3.04 (2H, t, J=6.8 Hz), 3.31, 3.64 (2H, ABq, J=18.1 Hz), 4.33 (2H, q, J=7 Hz), 4.57 (2H, t, J=7 Hz), 5.23 (1H, d, J=5 Hz), 5.64, 5.89 (2H, ABq, J=14.8 Hz), 5.85 (1H, d, J=5 Hz), 7.86 (1H, dd, J=8.2 Hz, 6.6 Hz), 8.78 (1H, d, J=8.2 Hz), 8.81 (1H, d, J=6.6 Hz), 8.85 (1H, S). IR (KBr) cm⁻¹: 1774, 1671, 1617, 1523, 1489, 1462. Elementary Analysis as $C_{24}H_{28}N_{10}O_5S_2 \cdot 1.6HCl$, $4.3H_2O$; calc.: C, 39.14; H, 5.23; N, 19.02; S, 8.71; Cl, 7.70; found: C, 39.23; H, 5.17; N, 19.13; S, 8.57; Cl, 7.68.

EXAMPLE 20

4.19 (2H, q, J=7.2 Hz), 4.45 (2H, m), 5.11 (3H, m), 5.29 (1H, d, J=4.2 Hz), 5.59, 6.10 (2H, ABq, J=14.7 Hz), 5.79 (2H, m), 6.93 (2H, d, J=8.7 Hz), 7.38 (2H, d, J=8.7 Hz), 7.96 (1H, m), 8.86 (1H, d, J=6.6 Hz), 9.02 (1H, d, J=8.4 Hz), 9.10 (1H, S), 9.67 (1H, d, J=8.7 Hz), 12.59 (1H, S), 5.94 (1H, dd, J=4.8 Hz, 8.7 Hz). IR (Nujol) cm⁻¹: 1760, 1700, 1665, 1530, 1500.

(2) Compound 89b (1.31 g, 1.22 mmol) was dissolved in CH₂Cl₂ 23 ml and MeNO₂ 6 ml and the mixture was stirred under cooling. Anisole (1.59 ml, 12 eq) and 1 mol AlCl₃/MeNO₂ (12.2 ml, 10 eq) were added thereto and the mixture was stirred at 5° C. for 1.5 hr. The reaction mixture was poured into a mixture of 0.25N HCl 30 ml and Et₂O 60 ml with stirring. The water layer was separated, washed with Et₂O 60 ml, and purified with HP-20. Lyophilization gave compound 90b (0.23 g, yield 25%).

¹H-NMR (D₂O) δ: 1.30 (3H, t, J=7.2 Hz), 2.40 (2H, m), 3.17 (2H, m), 3.31, 3.64 (2H, ABq, J=18.0 Hz), 3.667 (2H,

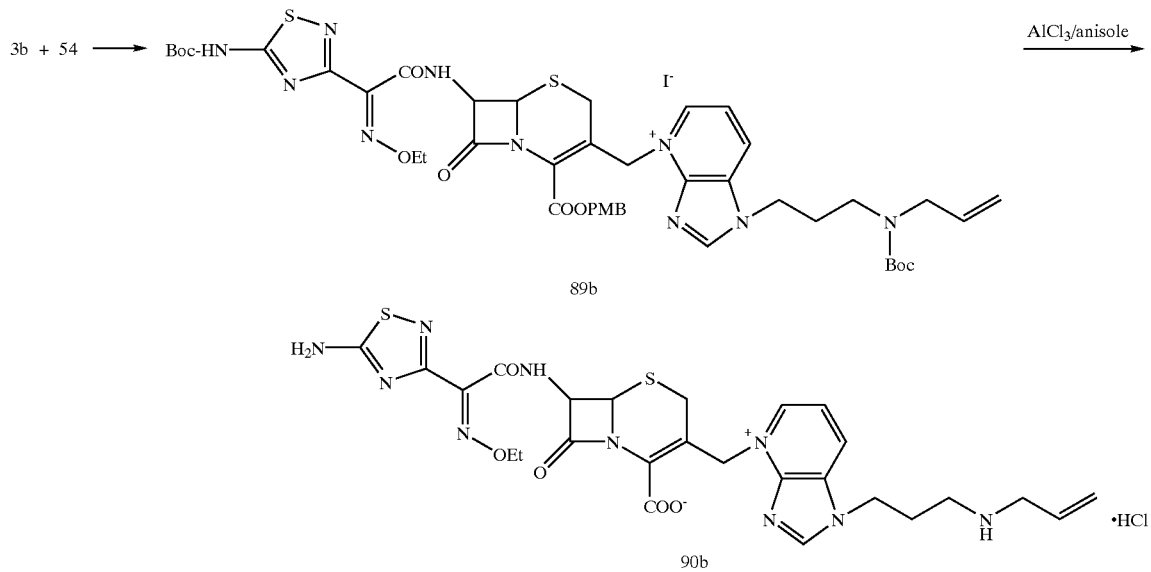

(1) To a solution of compound 54 (0.41 g, 1.3 mmol) of Reference Example 20 in MeCN 4 ml, was added a solution of compound 3b (1.08 g, 1.1 eq) in MeCN 8 ml under stirring and ice-cooling and the mixture was stirred at room temperature for 1.5 hr. From the reaction mixture, MeCN was evaporated under reduced pressure and the residue was washed with Et₂O 60 ml to give compound 89b (1.33 g, yield 95%).

¹H-NMR (DMSO-d6) δ: 1.23 (3H, t, J=7.2 Hz), 0.35 (9H, S), 1.51 (9H, S), 2.10 (2H, m), 3.20 (2H, m), 3.77 (3H, S),

S), 4.32 (2H, q, J=7.2 Hz), 4.64 (2H, t, J=7.5 Hz), 5.23 (1H, d, J=5.1 Hz), 5.53 (4H, m), 5.88 (3H, m), 7.89 (1H, dd, J=8.1 Hz, 6.3 Hz), 8.79 (1H, d, J=8.1 Hz), 8.85 (1H, d, J=6.3 Hz), 8.87 (1H, S). IR (KBr) cm⁻¹: 1774, 1670, 1613, 1526, 1488, 1462. Elementary Analysis as $C_{26}H_{80}N_{10}O_5S_2 \cdot 1.0HCl$, $5.0H_2O$; calc.: C, 41.46; H, 5.49; N, 18.60; S, 8.51; Cl, 4.71; found: C, 41.47; H, 5.31; N, 18.76; S, 8.29; Cl, 4.48.

EXAMPLE 21

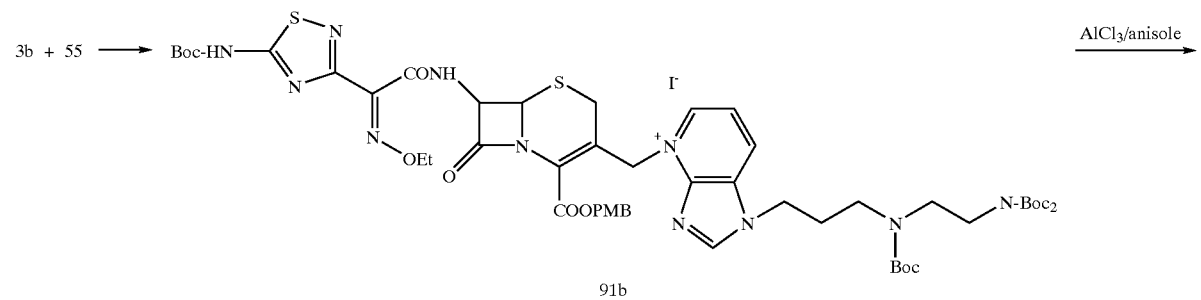

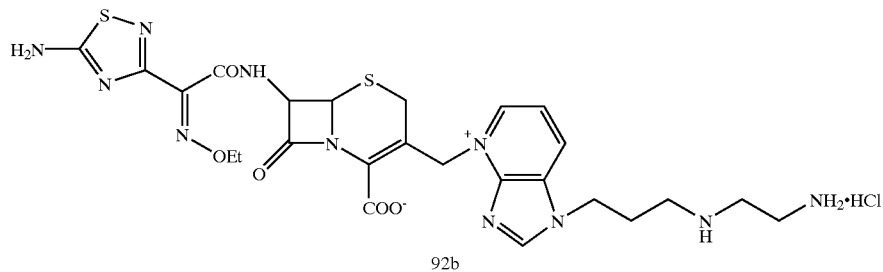

92b (1) Compound 55 (1.14 g, 2.19 mmol) of Reference Example 21 and compound 3b (2.0 g, 1.2 eq) were dissolved in MeCN 20 ml and the mixture was stirred at room temperature for 3 hr. From the reaction mixture, MeCN was evaporated under reduced pressure and the residue was washed with Et$_2$O 50 ml to give compound 91b (2.64 g, yield 94%).

$^1$H-NMR (DMSO-d6) δ: 1.24 (3H, t, J=7.2 Hz), 1.38 (9H, S), 1.43 (18H, S), 1.51 (9H, S), 2.06 (2H, m), 3.77 (3H, S), 4.20 (2H, q, J=7.2 Hz), 4.45 (2H, m), 5.10 (1H, d, J=5 Hz), 5.29 (2H, m), 5.60, 6.11 (2H, ABq, J=14.4 Hz), 5.95 (1H, dd, 5.23 (1H, d, J=5 Hz), 5.61, 5.91 (2H, ABq, J=14.8 Hz), 5.85 (1H, d, J=5 Hz), 7.89 (1H, dd, J=8 Hz, 6.4 Hz), 8.80 (1H, d, J=8 Hz), 8.84 (1H, d, J=6.4 Hz), 8.88 (1H, S). IR (KBr) cm$^{-1}$: 1772, 1668, 1610, 1524, 1488, 1462. Elementary Analysis as C$_{25}$H$_{81}$N$_{11}$O$_5$S$_2$.2.2HCl, 5.0H$_2$O; calc.: C, 37.53; H, 5.44; N, 19.26; S, 8.02; Cl, 9.75; found: C, 37.53; H, 5.41; N, 19.47; S, 7.96; Cl, 9.77.

EXAMPLE 22

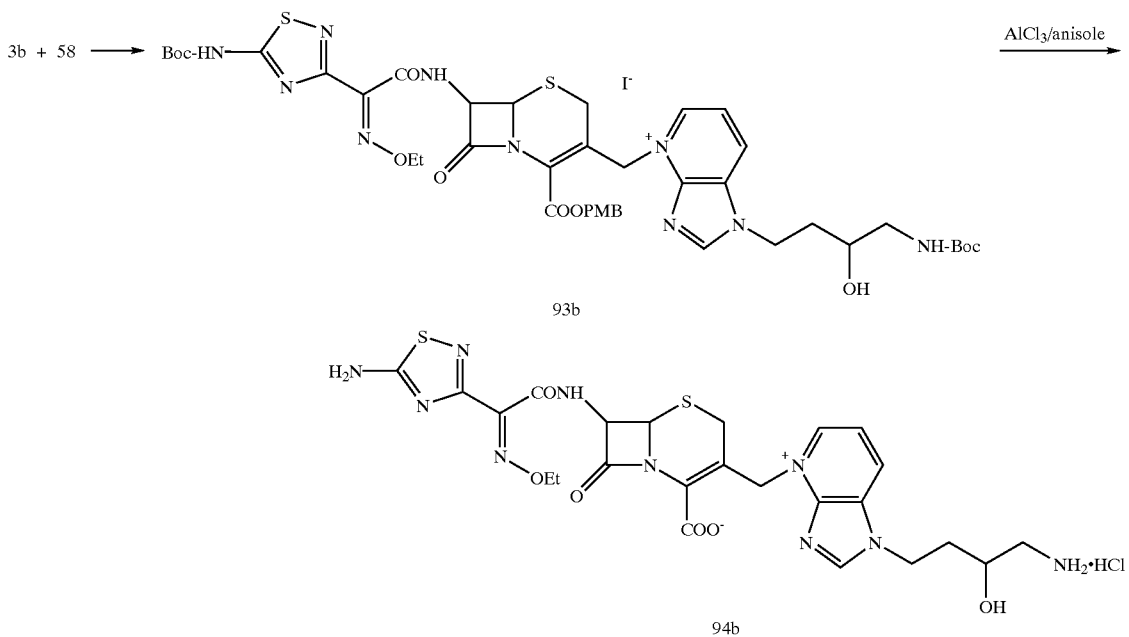

J=8.2 Hz, 55 Hz), 6.94 (2H, d, J=8.6 Hz), 7.39 (2H, d, J=8.6 Hz), 7.97 (1H, m), 8.87 (1H, d, J=5.4 Hz), 9.05 (1H, d, J=8.2 Hz), 9.10 (1H, S), 9.69 (1H, d, J=8.2 Hz), 12.61 (1H, S). IR (Nujol) cm$^{-1}$: 1781, 1715, 1690, 1545, 1518.

(2) Compound 91b (2.62 g, 2.05 mmol) was dissolved in CH$_2$Cl$_2$ 40 ml and MeNO$_2$ 10 ml and the mixture was stirred under cooling. Anisole (2.67 ml, 12 eq) and 1 mol AlCl$_3$/MeNO$_2$ (20.5 ml, 10 eq) were added thereto and the mixture was stirred at 5° C. for 1.5 hr. The reaction mixture was poured into a mixture of 0.25N HCl 50 ml and Et$_2$O 100 ml with stirring. The water layer was separated, washed with Et$_{20\ 100}$ ml and purified with HP-20. Lyophilization gave compound 92b (0.23 g, yield 14%).

$^1$H-NMR (D$_2$O) δ: 1.31 (3H, t, J=7 Hz), 2.45 (2H, m), 3.42 (6H, m), 4.33 (2H, q, J=7 Hz), 4.66 (2H, d, J=7.4 Hz), (1) Compound 58 (0.36 g, 1.17 mmol) of Reference Example 23 and compound 3b (1.07 g, 1.2 eq) were dissolved in DMF 6 ml and the mixture was stirred at room temperature for 1.5 hr. The reaction mixture was added to Et$_2$O 300 ml under stirring, then the precipitate was filtered to give compound 93b (1.14 g, yield 92%).

$^1$H-NMR (DMSO-d6) δ: 1.24 (3H, t, J=7.2 Hz), 1.36 (9H, S), 1.51 (9H, S), 2.95 (2H, m), 3.77 (3H, S), 4.20 (2H, q, J=7.2 Hz), 4.55 (2H, m), 4.95 (1H, d, J=5.4 Hz), 5.10 (1H, d, J=5.2 Hz), 5.29 (2H, S), 5.58, 6.11 (2H, ABq, J=14.6 Hz), 5.95 (1H, dd, J=8.6 Hz, 5.2 Hz), 6.94 (2H, d, J=8.2 Hz), 7.38

(2H, d, J=8.2 Hz), 7.95 (1H, m), 8.85 (1H, d, J=6.6 Hz), 8.99 (1H, d, J=8 Hz), 9.68 (1H, d, J=8.6 Hz), 12.6 (1H, S). IR (Nujol) cm$^{-1}$: 1785, 1710, 1695, 1680, 1550, 1515.

(2) Compound 93b (1.14 g, 1.07 mmol) was dissolved in $CH_2Cl_2$ 20 ml and $MeNO_2$ 7 ml and the mixture was stirred under cooling. Anisole (1.40 ml, 12 eq) and 1 mol $AlCl_3$/$MeNO_2$ (10.7 ml, 10 eq) were added thereto and the mixture was stirred at 5° C. for 1.5 hr. The reaction mixture was poured into a mixture of 0.25N HCl 40 ml and $Et_2O$ 80 ml. The water layer was separated, washed with $Et_2O$ 80 ml, and purified with HP-20. Lyophilization gave compound 94b (0.35 g, yield 41%).

$^1$H-NMR ($D_2O$) δ: 1.30 (3H, t, J=7 Hz), 2.20 (2H, m), 3.20 (2H, m), 3.31, 3.63 (2H, ABq, J=18.3 Hz), 3.88 (1H, m), 4.33 (2H, q, J=7 Hz), 4.69 (2H, t, J=6.2 Hz), 5.23 (1H, d, J=5 Hz), 5.64, 5.90 (2H, ABq, J=14.1 Hz), 5.86 (1H, d, J=5 Hz), 7.87 (1H, dd, J=8.2 Hz, 6.2 Hz), 8.79 (1H, d, J=8.2 Hz), 8.82 (1H, d, J=6.2 Hz), 8.87 (1H, S). IR (KBr) cm$^{-1}$: 1772, 1673, 1632, 1523, 1489, 1462. Elementary Analysis as $C_{24}H_{28}N_{10}O_6S_2 \cdot 1.5HCl$, $4.5H_2O$; calc.: C, 38.30; H, 5.17; N, 18.61; S, 8.52; Cl, 7.07; found: C, 38.30; H, 5.00; N, 18.57; S, 8.29; Cl, 6.92.

EXAMPLE 23

(1) Compound 61 (0.392 g, 1.34 mmol) of Reference Example 25 and compound 3b (1.22 g, 1.2 eq) was dissolved in DMF 7 ml and the mixture was stirred at room temperature for 1 hr. The reaction mixture was added to $Et_2O$ 300 ml under stirring, then the precipitate was filtered to give compound 95b (1.33 g, yield 94%).

$^1$H-NMR (DMSO-d6) δ: 1.23 (3H, t, J=6.9 Hz), 1.51 (18H, S), 3.77 (3H, S), 4.19 (2H, q, J=6.9 Hz), 5.61, 6.09 (2H, ABq, J=15.0 Hz), 5.95 (1H, dd, J=8.1 Hz, 5.0 Hz), 6.95 (2H, d, J=8.7 Hz), 7.39 (2H, d, J=8.7 Hz), 8.01 (1H, m), 8.88 (1H, d, J=6.6 Hz), 8.98 (1H, d, J=10.8 Hz), 9.67 (1H, d, J=8.1 Hz), 12.59 (1H, S). IR (Nujol) cm$^{-1}$: 1785, 1708, 1680, 1540, 1515.

(2) Compound 95b (1.31 g, 1.25 mmol) was dissolved in $CH_2Cl_2$ 25 ml and $MeNO_2$ 8 ml and the mixture was stirred under cooling. Anisole (1.63 ml, 12 eq) and 1 mol $AlCl_3$/$MeNO_2$ (12.5 ml, 10 eq) were added thereto and the mixture was stirred at 5° C. for 1.5 hr. The reaction mixture was poured into a mixture of 0.25N HCl 50 ml and $Et_2O$ 100 ml, then the water layer was separated, washed with $Et_2O$ 100 ml, and purified with HP-20. Lyophilization gave compound 96b (0.29 g, yield 31%).

$^1$H-NMR ($D_2O$) δ: 1.31 (3H, t, J=7 Hz), 3.33, 3.64 (2H, ABq, J=17.9 Hz), 3.80 (5H, m), 4.33 (2H, q, J=7 Hz), 4.88 (2H, m), 5.23 (1H, d, J=4.8 Hz), 5.86 (1H, d, J=4.8 Hz), 5.65, 5.96 (2H, ABq, J=14.5 Hz), 7.92 (1H, dd, J=8.2 Hz, 6.6 Hz), 8.86 (1H, d, J=8.2 Hz), 8.89 (1H, d, J=6.6 Hz), 8.92 (1H, S). IR (KBr) cm$^{-1}$: 1772, 1633, 1523, 1488, 1463. Elementary Analysis as $C_{23}H_{26}N_{10}O_6S_2 \cdot 1.5HCl$, $4.6H_2O$; calc.: C, 37.31; H, 5.01; N, 18.92; S, 8.66; Cl, 7.19; found: C, 37.33; H, 4.93; N, 18.93; S, 8.58; Cl, 7.32.

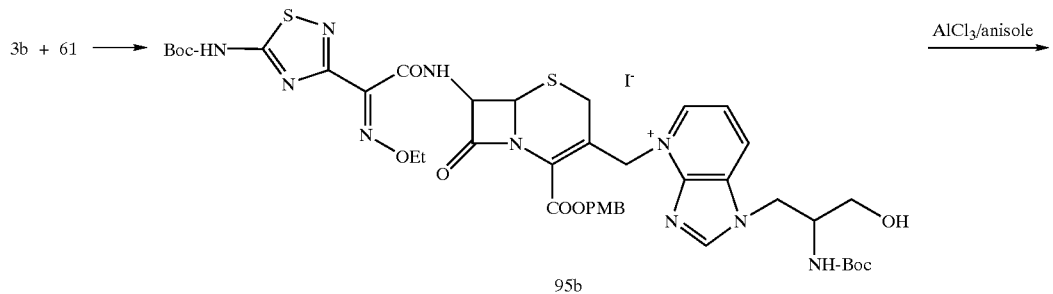

95b

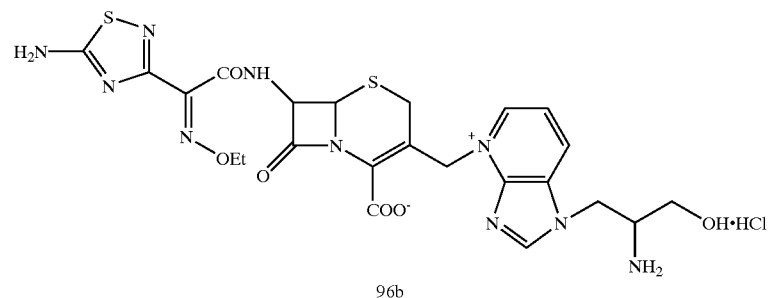

96b

EXAMPLE 24

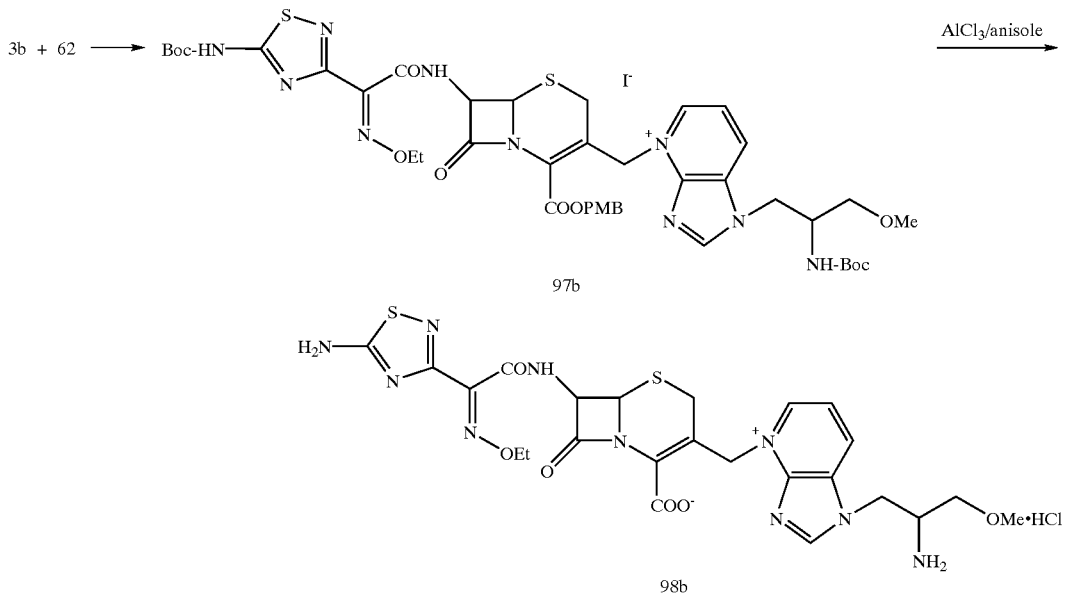

(1) Compound 62 (0.36 g, 1.18 mmol) of Reference Example 26 and compound 3b (1.07 g, 1.2 eq) were dissolved in DMF 8 ml and the mixture was stirred at room temperature for 1.5 hr. The reaction mixture was added to $Et_2O$ 300 ml under stirring, then the precipitate was filtered to give compound 97b (1.26 g, yield 100%).

$^1$H-NMR (DMSO-d6) δ: 1.23 (3H, t, J=6.8 Hz), 1.51 (18H, S), 3.77 (3H, S), 4.20 (2H, q, J=6.8 Hz), 6.94 (2H, d, J=7 Hz), 7.39 (2H, d, J=7 Hz), 8.0 (1H, m), 8.73 (1H, m), 8.90 (1H, S), 8.98 (1H, d, J=8.6 Hz), 9.68 (1H, d, J=8.4 Hz), 12.61 (1H, S). IR (Nujol) cm$^{-1}$: 1785, 1710, 1690, 1550, 1515.

(2) Compound 97b (1.65 g, 1.69 mmol) was dissolved in $CH_2Cl_2$ 30 ml and $MeNO_2$ 10 ml and the mixture was stirred under cooling. Anisole (2.20 ml, 12 eq) and 1 mol $AlCl_3$/$MeNO_2$ (16.9 ml, 10 eq) were added thereto and the mixture was stirred at 5° C. for 1.5 hr. The reaction mixture was poured into a mixture of 0.25N HCl 60 ml and $Et_2O$ 120 ml, then the water layer was separated, washed with $Et_2O$ 120 ml, and purified with HP-20. Lyophilization gave compound 98b (0.26 g, yield 21%).

$^1$H-NMR ($D_2O$) δ: 1.30 (3H, t, J=7 Hz), 3.33, 3.64 (2H, ABq, J=18.8 Hz), 3.41 (3H, S), 3.65 (2H, m), 3.14 (1H, m), 4.33 (2H, q, J=7 Hz), 4.89 (2H, d, J=7 Hz), 5.23 (1H, d, J=4.6 Hz), 5.67, 5.96 (2H, ABq, J=14.9 Hz), 5.86 (1H, d, J=4.6 Hz), 7.93 (1H, dd, J=8.2 Hz, 6.4 Hz), 8.83 (1H, d, J=8.2 Hz), 8.89 (1H, d, J=6.4 Hz), 8.91 (1H, S). IR (KBr) cm$^{-1}$: 1774, 1671, 1633, 1524, 1488, 1463. Elementary Analysis as $C_{24}H_{28}N_{10}O_6S_2 \cdot 1.6HCl$, $4.0H_2O$; calc.: C, 38.58; H, 5.08; N, 18.75; S, 8.58; Cl, 7.59; found: C, 38.61; H, 5.00; N, 18.57; S, 8.34; Cl, 7.56.

EXAMPLE 25

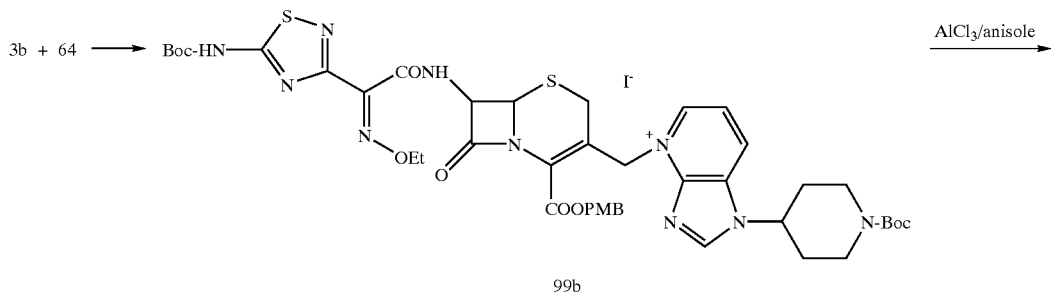

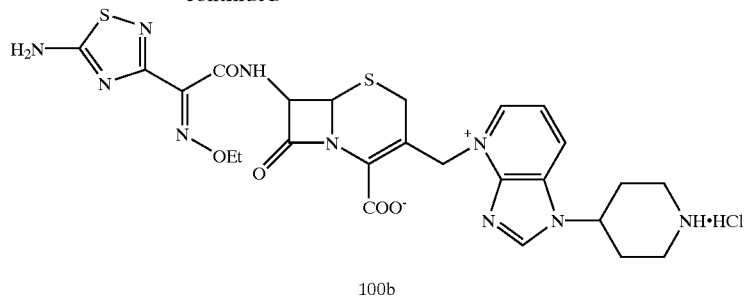

100b (1) Compound 64 (0.96 g, 3.17 mmol) of Reference Example 27 and compound 3b (2.89 g, 1.2 eq) were dissolved in DMF 13 ml and the mixture was stirred at room temperature for 1 hr. The reaction mixture was added to Et$_2$O 500 ml under stirring, then the precipitate was filtered to give compound 99b (3.36 g, yield 100%).

$^1$H-NMR (DMSO-d6) δ: 1.24 (3H, t, J=7 Hz), 1.45 (9H, S), 1.50 (9H, S), 3.76 (3H, S), 4.20 (2H, q, J=7 Hz), 5.11 (1H, d, J=4.2 Hz), 5.29 (2H, S), 5.56, 6.11 (2H, ABq, J=14.6 Hz), 5.94 (1H, dd, J=8.2 Hz, 4.2 Hz), 6.94 (2H, d, J=8.6 Hz), 7.39 (2H, d, J=8.6 Hz), 7.95 (1H, m), 8.76 (1H, d, J=6.4 Hz), 9.10 (1H, d, J=8.2 Hz), 9.18 (1H, S), 9.67 (1H, d, J=8.2 Hz), 12.59 (1H, S). IR (Nujol) cm$^{-1}$: 1785, 1710, 1665, 1545.

(2) Compound 99b (3.36 g, 3.17 mmol) was dissolved in CH$_2$Cl$_2$ 75 ml and MeNO$_2$ 35 ml and the mixture was stirred under cooling. Anisole (4.13 ml, 12 eq) and 1 mol AlCl$_3$/MeNO$_2$ (31.7 ml, 10 eq) were added thereto and the mixture was stirred at 5° C. for 1.5 hr with stirring. The reaction mixture was poured into a mixture of 0.25N HCl 130 ml and Et$_2$O 260 ml, then the water layer was separated, washed with Et$_2$O 260 ml, and purified with HP-20. Lyophilization gave compound 100b (0.62 g, yield 25%).

$^1$H-NMR (D$_2$O) δ: 1.30 (3H, t, J=7.5 Hz), 2.50 (4H, m), 3.33 (3H, m), 3.70 (3H, m), 4.33 (2H, q, J=7.5 Hz), 5.07 (1H, m), 5.23 (1H, d, J=4.8 Hz), 5.64, 5.91 (2H, ABq, J=14.7 Hz), 5.85 (1H, d, J=4.8 Hz), 7.89 (1H, m), 8.85 (2H, m), 8.98 (1H, S). IR (KBr) cm$^{-1}$: 1773, 1670, 1616, 1524, 1460. Elementary Analysis as C$_{25}$H$_{28}$N$_{10}$O$_5$S$_2$.1.4HCl, 4.3H$_2$O; calc.: C, 40.51; H, 5.17; N, 18.90; S, 8.65; Cl, 6.70; found: C, 40.52; H, 5.20; N, 18.91; S, 8.48; Cl, 6.48.

EXAMPLE 26

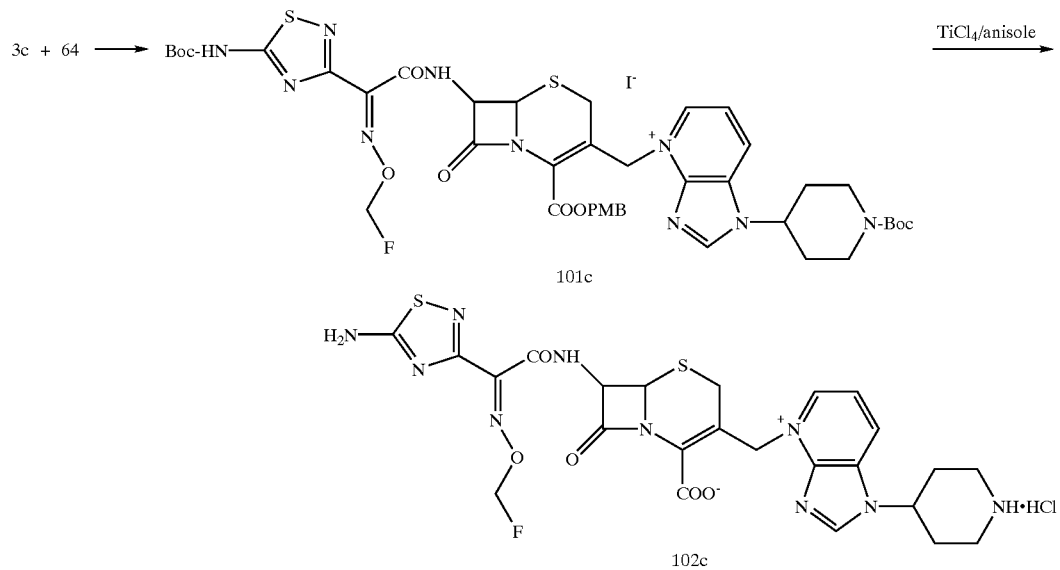

101c

102c (1) Compound 64 (0.454 g, 1.5 mmol) of Reference Example 27 and compound 3c (1.37 g, 1.2 eq) were dissolved in DMF 6 ml and the mixture was stirred at room temperature for 1 hr. The reaction mixture was added to Et$_2$O 300 ml, then the precipitate was filtered to give compound 101c (1.64 g, yield 100%).

$^1$H-NMR (DMSO-d6) δ: 1.44 (9H, S), 1.51 (9H, S), 2.10 (4H, m), 3.77 (3H, S), 4.19 (1H, m), 5.12 (1H, d, J=4.6z), 5.29 (2H, S), 5.57, 6.10 (2H, ABq, J=13.6 Hz), 6.93 (2H, d, J=9 Hz), 7.38 (2H, d, J=9 Hz), 7.95 (1H, m), 8.86 (1H, d, J=5.8 Hz), 9.10 (1H, d, J=7.8 Hz), 12.68 (1H, S). IR (Nujol) cm$^{-1}$: 1790, 1715, 1690, 1665, 1550.

(2) Compound 101c (1.62 g, 1.52 mmol) was dissolved in CH$_2$Cl$_2$ 27 ml and MeNO$_2$ 14 ml and the mixture was stirred under cooling. Anisole (1.98 ml) and TiCl$_4$ (1.67 ml, 10 eq) were added thereto and the mixture was stirred at 5° C. for 1.5 hr. The reaction mixture was poured into a mixture of 0.25N HCl 80 ml and Et$_2$O 160 ml, then the water layer was separated, washed with Et$_2$O 160 ml, and purified with HP-20. Lyophilization gave compound 102c (0.35 g, yield 30%).

$^1$H-NMR (D$_2$O) δ: 2.50 (4H, m), 3.34 (3H, m), 3.70 (3H, m), 5.05 (1H, m), 5.23 (1H, d, J=5 Hz), 5.65, 5.90 (2H, ABq, J=16.6 Hz), 5.82 (2H, d, J=54.4 Hz), 5.84 (1H, d, J=5 Hz), 7.87 (1H, dd, J=8.2 Hz, 6.2 Hz), 8.81 (1H, d, J=8.2 Hz), 8.87 (11H, d, J=6.2 Hz), 8.99 (1H, S). IR (KBr) cm$^{-1}$: 1774, 1674, 1616, 1525, 1460. Elementary Analysis as C$_{24}$H$_{25}$N$_{10}$O$_5$S$_2$F.1.5HCl, 2.6H$_2$O; calc.: C, 40.13; H, 4.46; N, 19.50; S, 8.93; F, 2.65; Cl, 7.41; found: C, 40.16; H, 4.48; N, 19.46; S, 7.69; F, 2.15; Cl, 7.18.

EXAMPLE 27

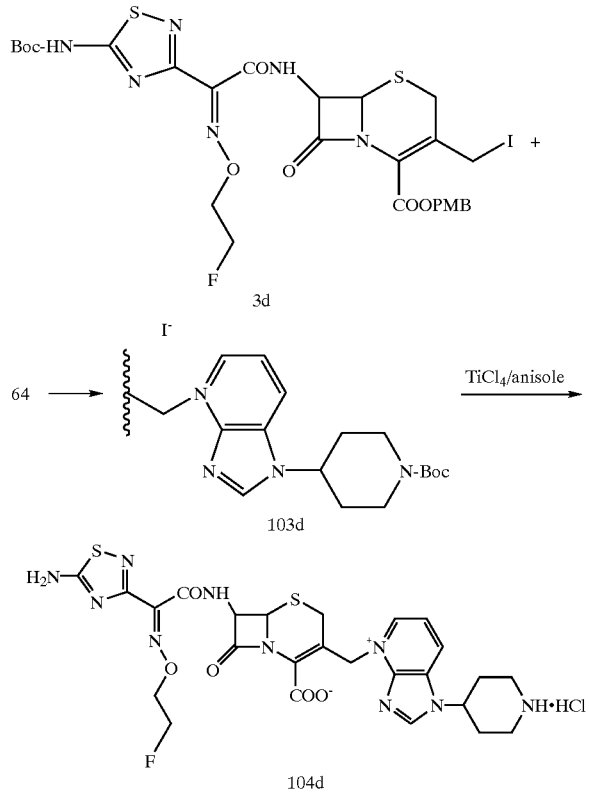

(1) Compound 64 (0.454 g, 1.5 mmol) of Reference Example 27 and compound 3d (1.51 g, 1.3 eq.) were dissolved in DMF 8 ml and the mixture was stirred at room temperature for 1.5 hr. The reaction mixture was added to Et$_2$O 300 ml under stirring, then the precipitation was filtered to give compound 103d (1.68 g, yield 100%).

$^1$H-NMR (DMSO-d6) δ: 1.44 (9H, S), 1.50 (9H, S), 3.77 (3H, S), 5.10 (1H, d, J=5 Hz), 5.29 (2H, S), 5.57, 6.12 (2H, ABq, J=14.6 Hz), 5.95 (1H, dd, J=8.6 Hz, 5 Hz), 6.94 (2H, d, J=8.6 Hz), 7.39 (2H, d, J=8.6 Hz), 7.96 (1H, m), 8.87 (1H, d, J=5.8 Hz), 9.10 (1H, d, J=8.6 Hz), 9.18 (1H, S), 9.74 (1H, d, J=8.6 Hz), 12.62 (1H, S). IR (Nujol) cm$^{-1}$: 1790, 1719, 1695, 1680, 1665, 1555, 1540, 1519.

(2) Compound 103d (1.66 g, 1.54 mmol) was dissolved in CH$_2$Cl$_2$ 27 ml and MeNO$_2$ 14 ml and the mixture was stirred under cooling. Anisole (2.01 ml, 12 eq) and TiCl$_4$ (1.69 ml, 10 eq) were added thereto and the mixture was stirred at 5° C. for 1.5 hr. The reaction mixture was poured into a mixture of 0.25N HCl 80 ml and Et$_2$O 160 ml, then the water layer was separated, washed with Et$_2$O 160 ml, and purified with HP-20. Lyophilization gave compound 104d (0.35 g, yield 29%).

$^1$H-NMR (D$_2$O) δ: 2.50 (4H, m), 3.35 (3H, m), 3.69 (3H, m), 5.25 (1H, d, J=4.6 Hz), 5.71, 5.94 (2H, ABq, J=14.8 Hz), 5.87 (1H, d, J=4.6 Hz), 7.89 (1H, dd, J=8.2 Hz, 6.4 Hz), 8.84 (1H, d, J=8.2 Hz), 8.88 (1H, d, J=6.4 Hz), 9.00 (1H, S). IR (KBr) cm$^{-1}$: 1774, 1671, 1615, 1524, 1460. Elementary Analysis as C$_{25}$H$_{27}$N$_{10}$O$_5$S$_2$F.1.6HCl, 4.8H$_2$O; calc.: C, 38.71; H, 4.97; N, 18.06; S, 8.27; F, 2.45; Cl, 7.32; found: C, 38.73; H, 4.93; N, 17.82; S, 8.10; F, 2.29; Cl, 7.23.

EXAMPLE 28

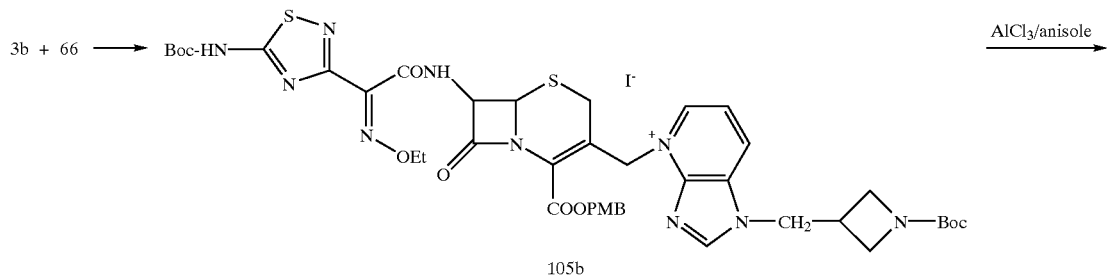

-continued

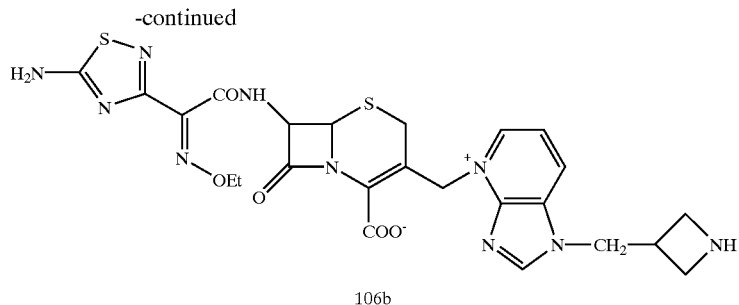

106b (1) Compound 66 (0.41 g, 1.42 mmol) of Reference Example 28 and compound 3b (1.29 g, 1.2 eq) were dissolved in DMF 10 ml and the mixture was stirred at room temperature for 1.5 hr. The reaction mixture was added to Et$_2$O 300 ml under stirring, then the precipitate was filtered to give compound 105b (1.38 g, yield 93%).

$^1$H-NMR (DMSO-d6) δ: 1.23 (3H, t, J=7 Hz), 1.38 (9H, S), 1.50 (1H, S), 3.77 (3H, S), 4.19 (2H, q, J=7 Hz), 5.09 (1H, d, J=5.2 Hz), 5.57, 6.10 (2H, ABq, J=14.6 Hz), 5.94 (1H, dd, J=8.2 Hz, 4.6 Hz), 6.94 (2H, d, J=8.6 Hz), 7.39 (2H, d, J=8.6 Hz), 7.95 (1H, m), 8.86 (1H, d, J=6.2 Hz), 9.08 (1H, d, J=8.2 Hz), 9.68 (1H, d, J=8.2Hz), 12.6 (1H, S). IR (Nujol) cm$^{-1}$: 1790, 1715, 1680, 1550, 1520.

(2) Compound 105b (1.36 g, 1.3 mmol) was dissolved in CH$_2$Cl$_2$ 24 ml and MeNO$_2$ 8 ml and the mixture was stirred under cooling. Anisole (1.69 ml, 12 eq) and 1 mol AlCl$_3$/MeNO$_2$ (13 ml, 10 eq) were added thereto and the mixture was stirred at 5° C. for 1.5 hr. The reaction mixture was poured into a mixture of 0.25N HCl 50 ml and Et$_2$O 100 ml, then the water layer was separated, washed with Et$_2$O 100 ml, and purified with HP-20. Lyophilization gave compound 106b (0.30 g, yield 31%).

$^1$H-NMR (D$_2$O) δ: 1.30 (3H, t, J=7 Hz), 3.31, 3.64 (2H, ABq, J=17.6 Hz), 5.23 (1H, d, J=4.6 Hz), 5.64, 5.91 (2H, ABq, J=15.4 Hz), 5.86 (1H, d, J=4.6 Hz), 7.90 (1H, dd, J=7.8 Hz, 6.4 Hz), 8.80 (1H, d, J=7.8 Hz), 8.86 (1H, d, J=6.4 Hz), 8.89 (1H, S). IR (KBr) cm$^{-1}$: 1773, 1670, 1616, 1524, 1487, 1463, 1450. Elementary Analysis as C$_{24}$H$_{26}$N$_{10}$O$_5$S$_2$.1.6HCl, 4.6H$_2$O; calc.: C, 38.95; H, 5.02; N, 18.93; S, 8.67; Cl, 7.67; found: C, 38.92; H, 15.08; N, 18.65; S, 8.33; Cl, 7.55.

EXAMPLE 29

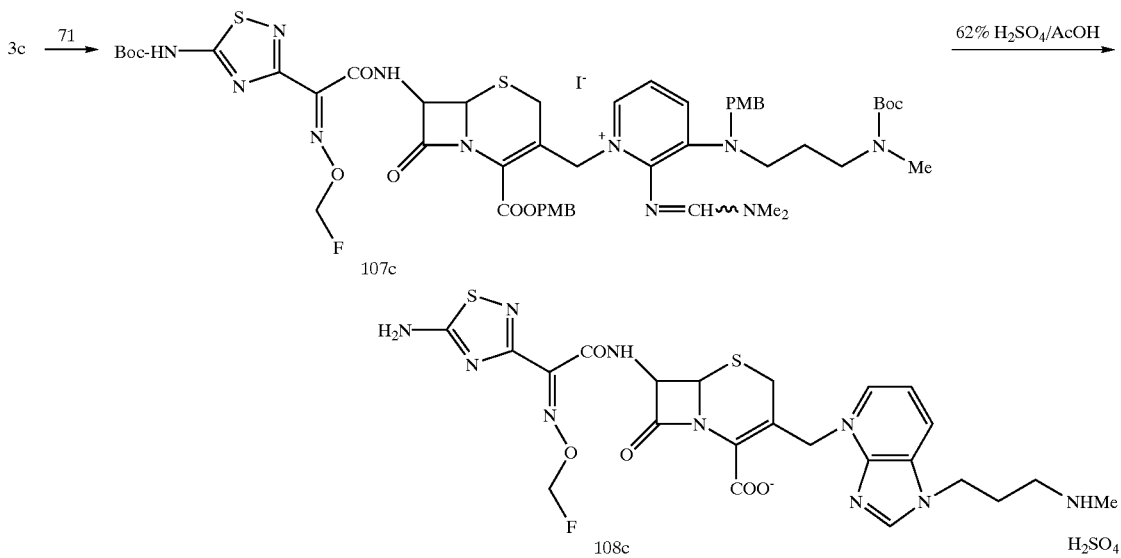

(1) Cmpound 3c (19.1 g, 25 mmol) and compound 71 (14.4 g, 1.2 eq) of Reference Example 31 were dissolved in DMF 40 ml and the mixture was stirred at room temperature for 2.5 hr. The reaction mixture was poured into 5% brine, then the precipitate was filtered, dried, and washed with AcOEt to give compound 107c (27.4 g, yield 96%).

$^1$H-NMR (DMSO-d6) δ: 1.32 (9H, S), 1.51 (9H, S), 2.71 (3H, S), 2.89 (3H, S), 3.10 (3H, S), 3.72 (3H, S), 3.76 (3H, S), 4.02 (2H, m), 5.10 (1H, d, J=4.8 Hz), 5.20 (4H, m), 5.82 (2H, d, J=54.6 Hz), 5.96 (1H, dd, J=8.1 Hz, 4.8 Hz), 6.87 (2H, q, J=8.4 Hz), 6.95 (2H, d, J=8.7 Hz), 7.00 (2H, d, J=8.4 Hz), 7.38 (2H, d, J=8.7 Hz), 7.22 (1H, m), 7.78 (1H, m), 8.16 (1H, m), 8.43 (1H, m). IR (CHCl$_3$) cm$^{-1}$: 1775, 1720, 1695, 1640, 1555, 1520.

(2) A solution of compound 107c (9.99 g, 8.2 mmol) in AcOH 18 ml was added to 62% H$_2$SO$_4$ 42 ml under keeping the reaction temperature at 5° C. After stirring at 5° C. for 1 hr, the reaction mixture was poured into i-PrOH, then the precipitate was filtered and dried under reduced pressure. The obtained precipitate was purified with HP-20 and crystallized from dil. H$_2$SO$_4$ to give compound 108c (1.90 g, yield 27%) as 1 sulfate 8-hydrate crystals.

¹H-NMR (D₂O) δ: 2.42 (2H, m), 2.73 (3H, S), 3.17 (2H, t, J=7.6 Hz), 3.30, 3.64 (2H, ABq, J=18.3 Hz), 4.62 (2H, t, J=7.4 Hz), 5.25 (1H, d, J=4.8 Hz), 5.70, 5.91 (2H, ABq, J=13.0 Hz), 5.82 (2H, d, J=54.6 Hz), 5.86 (4.8 Hz), 7.87 (1H, dd, J=8.2 Hz, 6.4 Hz), 8.80 (1H, d, J=8.2 Hz), 8.83 (1H, d, J=6.4 Hz), 8.88 (1H, S). IR (Nujol) δ: 1774, 1720, 1679, 1631, 1577, 1529, 1495, 1463, 1417. Elementary Analysis as C₂₃H₂₅N₁₀O₅S₂F·1.0H₂SO₄·8.2H₂O (calculated water content: 17.02%); calc.: C, 32.48; H, 5.14; N, 16.47; S, 11.31; F, 2.23; found: C, 32.57; H, 5.00; N, 16.49; S, 11.31; F, 2.22.

(3) An aqueous solution (45 ml) of the 8-hydrate crystal (31.7 g) obtained above (2) was subjected to HP-20 chromato with 0.001N HCl aq., and the eluted solution was mixed with poly(4-vinylpyridine) resin to adjust the pH to 4, then which was filtered. The filtrate was concentrated under reduced pressure up to 100 g, which was stirred under ice-cooling, then 2N H₂SO₄ was added thereto so as to adjust the pH to 1.5, whereby crystals were precipitated. After allowing to stand over night, the crystal was filtered, washed with cooled H₂O and cooled H₂O-EtOH successively, and dried under reduced pressure to give 1 sulfate·7-hydrate crystal of compound 108c 14 g.

Water content (KF: 15.43% Calc.: 15.21%)

The diffraction pattern of the 7-hydrate crystal is shown in Table A.

TABLE A

| 2 θ | I | 2 θ | I |
|---|---|---|---|
| 8.02 | 162 | 22.20 | 250 |
| 9.62 | 178 | 24.20 | 268 |
| 11.58 | 290 | 24.68 | 170 |
| 13.82 | 288 | 25.12 | 360 |
| 14.26 | 242 | 26.26 | 475 |
| 15.84 | 572 | 27.56 | 318 |
| 19.40 | 338 | 28.68 | 302 |
| 20.22 | 215 | 29.90 | 555 |
| 20.40 | 222 | 38.40 | 388 |
| 21.20 | 272 | | |

2 θ = diffraction angle (unit: degree),
I = intensity (measuring condition) Tube: Cu; Voltage: 40 KV; Current: 40 mA; Scanning: 3.0°/min; Step: 0.02°; Sampling angle: 5°; Termination angle: 40°.

The above 1 sulfate·7 hydrate crystal, i.e., compound 108c-2, has an inclination to become stable as 4- to 5-hydrate (calculated water content: 9.30~11.36%) upon dehydration. The crystals of 4- to 7-hydrate are deemed to show main peaks of the same diffraction pattern (2θ) as above, provided that the intensity (I) may be varied depending on the water content. The storage stability of vial preparations containing each crystal was examined to result in the order of stability: 4- to 5-hydrate>7-hydrate>8-hydrate.

EXAMPLE 30

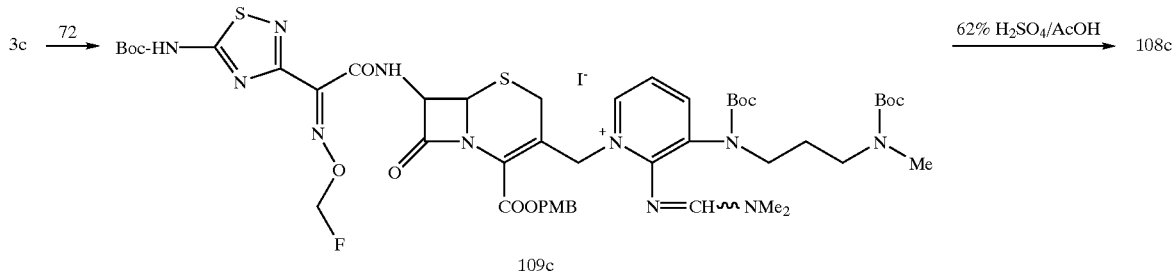

109c

1) Compound 3c (19.1 g, 25 mmol) of Reference Example 32 and compound 72 (13.2 g, 1 eq) were dissolved in DMF 40 ml and the mixture was stirred at room temperature for 17 hr. The reaction mixture was poured into diisopropylether, then the precipitated oily product was separated and dried under reduced pressure to give compound 109c (34.4 g, yield 100%).

¹H-NMR (DMSO-d6) δ: 1.38 (18H, S), 1.51 (9H, S), 2.78 (3H, S), 2.95 (3H, S), 3.08 (3H, S), 3.76 (3H, S), 5.21 (5H, m), 5.82 (2H, d, J=55.6 Hz), 5.95 (1H, m), 6.95 (2H, d, J=8 Hz), 7.38 (2H, d, J=8 Hz), 7.73 (1H, m), 8.24 (1H, m), 8.49 (1H, m). IR (CHCl₃) cm⁻¹: 1775, 1720, 1770, 1640, 1550, 1520, 1400.

(2) The same procedure as that of Example 29 (2), using compound 109c (9.7 g, 8.2 mmol), AcOH 18 ml, and 62% H₂SO₄ 42 ml, gave the above compound 108c (1.93 g, yield 28%).

EXAMPLE 31

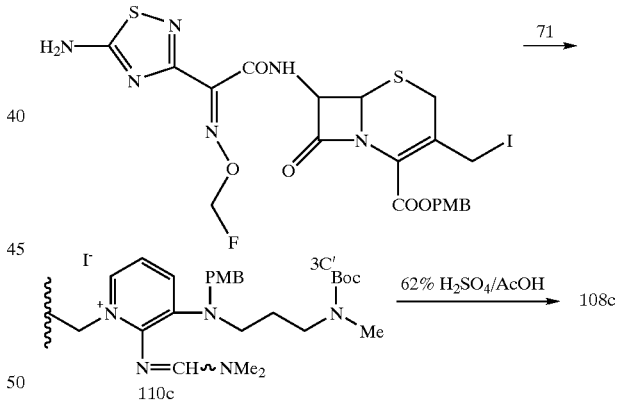

110c (1) Compound 3c' (25.6 g, 38.7 mmol) and compound 71 (22.3 g, 1.2 eq) of Reference Example 31 were dissolved in dimethylacetoamide 50 ml and the mixture was stirred at room temperature for 3.5 hr. The reaction mixture was poured into t-butyl acetate and the precipitate was filtered to give compound 110c (51.1 g, yield 100%).

¹H-NMR (DMSO-d6) δ: 1.32 (9H, S), 1.56 (2H, m), 2.70 (3H, S), 2.79 (3H, S), 3.10 (3H, S), 3.72 (3H, S), 3.76 (3H, S), 4.00 (2H, m), 5.08 (1H, d, J=4.7 Hz), 5.21 (5H, m), 5.60 (3H, m), 5.91 (3H, m), 6.96 (5H, m), 7.20 (1H, m), 7.37 (4H, d, J=8.7 Hz), 7.78 (1H, m), 8.18 (2H, m), 9.79 (1H, d, J=8.3 Hz). IR (CHCl₃) cm⁻¹: 1785, 1720, 1685, 1640, 1620, 1520, 1400.

(2) The same procedure as carried out in compound 110c (4.58 g, 4.1 mmol), AcOH 9 ml and 62% H₂SO₄ 21 ml, gave compound 108c (1.70 g, yield 49%).

EXAMPLE 32

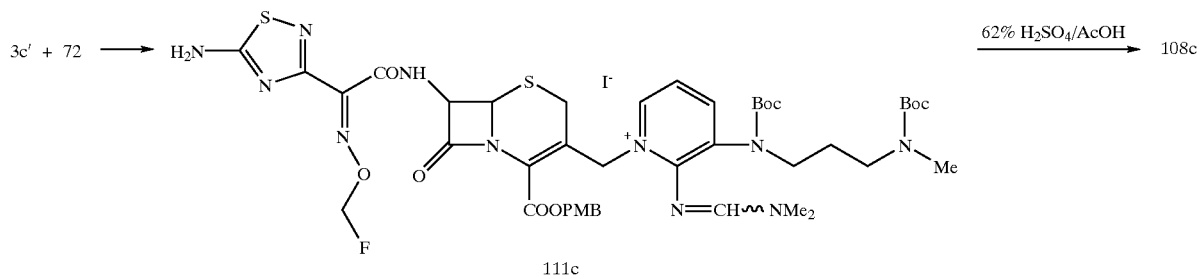

111c (1) Compound 3c' (18.15 g, 27.4 mmol) and compound 72 (13.1 g, 1.1 eq) of Reference Example 32 were dissolved in dimethylacetamide 40 ml and the mixture was stirred at room temperature for 17 hr. The reaction mixture was poured in 5% brine and the precipitate was filtered to give compound 111c (30.8 g, yield 100%).

$^1$H-NMR (DMSO-d6) δ: 1.39 (18H, S), 1.69 (2H, m), 2.79 (3H, S), 9.25 (3H, S), 3.08 (3H, S), 3.76 (3H, S), 5.24 (5H, m), 5.77 (2H, d, J=55.5 Hz), 5.91 (2H, m), 6.95 (2H, d, J=8.6 Hz), 7.38 (2H, d, J=8.6 Hz), 7.74 (1H, S), 8.22 (2H, m), 8.50 (1H, m). IR (CHCl$_3$) cm$^{-1}$: 1790, 1695, 1645, 1520, 1400.

(2) The same procedure as that of Example 29(2), using compound 111c (9.00 g, 8.2 mmol), AcOH 18 ml, and 62% H$_2$SO$_4$ 42 ml, gave the above compound 108c (3.70 g, yield 53%).

EXAMPLE 33

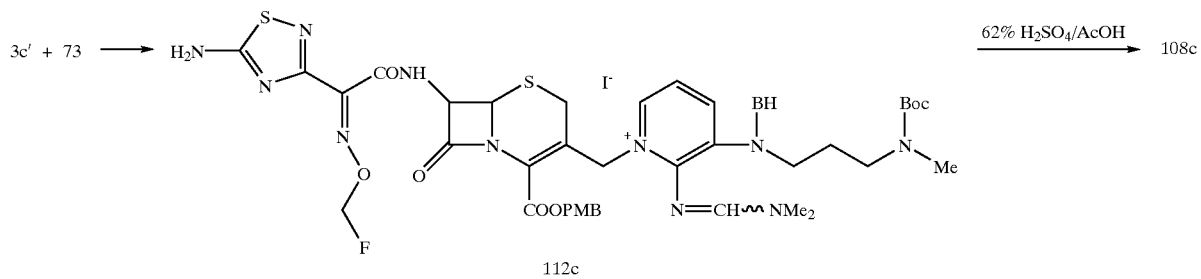

112c (1) To a solution of compound 73 (502 mg, 1 mmol) of Reference Example 33 in dimethylacetamide 1.2 ml, was added a solution of compound 3c' (662 mg, 1 eq) in dimethylacetamide 1.2 ml and the mixture was stirred at room temperature for 8 hr. The reaction mixture was poured in 5% brine, then the precipitate was filtered and dried to give compound 112c (1.11 g, yield 95%).

$^1$H-NMR (DMSO-d6) δ: 1.28 (9H, S), 2.70 (3H, S), 2.90 (3H, S), 3.05 (3H, S), 3.76 (3H, S), 5.15 (1H, d, J=4.8 Hz), 5.20 (3H, m), 5.57 (3H, m), 5.78 (2H, d, J=55.2 Hz), 5.92 (1H, dd, J=8.4 Hz, 4.8 Hz), 6.94 (2H, d, J=8.4 Hz), 7.20~7.39 (13H, m), 7.70 (1H, m), 8.23 (2H, m), 8.43 (1H, S). IR (CHCl$_3$) cm$^{-1}$: 780, 1675, 1635, 1605, 1510.

(2) The same procedure as carried out in Example 29(2), using compound 112c (2.63 g, 2.25 mmol), AcOH 5.2 ml, and 62% H$_2$SO$_4$ 16 g, gave the above compound 108c (0.96 g, yield 50%).

EXAMPLE 34

A variety of compound (I) was further synthesized according to the above general method (2). The structure of compound (I) and the aforementioned synthesis methods A to F of compound (IV), a material for the 3-side chain, are shown in Table 1, with the NMR, IR, and Elementary Analysis in Tables 2 to 4.

TABLE 1-1

Compound (I) R1 = amino R3 = H (provided R3 = Mein compound 246b)

| No. | X | R2 | R4 | R5 | Method of 3-side chain |
|---|---|---|---|---|---|
| 211b | N | Et | (s) CH$_2$CH$^+$(NH$_2$)Me | H | C |
| 211c | N | CH$_2$F | (s) CH$_2$CH$^+$(NH$_2$)Me | H | C |
| 212c | N | CH$_2$F | (CH$_2$)$_3$N(Me)CO$_2$$^t$Bu | H | E |
| 213b | N | Et | CH$_2$C(Me)$_2$NH$_2$ | H | B |
| 214b | N | Et | (CH$_2$)$_2$NHMe | H | C |
| 214c | N | CH$_2$F | (CH$_2$)$_2$NHMe | H | C |
| 215d | N | CH$_2$—CH$_2$F | (CH$_2$)$_3$NH(CH$_2$)$_2$—OSO3H | H | E |

TABLE 1-1-continued

Compound (I) R1 = amino R3 = H (provided R3 = Mein compound 246b)

| No. | X | R2 | R4 | R5 | Method of 3-side chain |
|---|---|---|---|---|---|
| 216d | N | CH$_2$—CH$_2$F | (CH$_2$)$_3$NH(CH$_2$)$_2$OH | H | E |
| 216b | CH | Et | (CH$_2$)$_3$NH(CH$_2$)$_2$OH | H | E |
| 216g | N | H | (CH$_2$)$_3$NH(CH$_2$)$_2$OH | H | E |
| 220b | N | Et | H | Me | D |
| 221b | N | Et | (CH$_2$)$_3$NH$_2$ | Me | C |
| 221c | N | CH$_2$F | (CH$_2$)$_3$NH$_2$ | Me | C |
| 221d | N | CH$_2$—CH$_2$F | (CH$_2$)$_3$NH$_2$ | Me | C |
| 221a | N | Me | (CH$_2$)$_3$NH$_2$ | Me | C |
| 222b | N | Et | (CH$_2$)$_3$NHMe | Me | C |
| 222c | N | CH$_2$F | (CH$_2$)$_3$NHMe | Me | C |
| 223c | N | CH$_2$F | (CH$_2$)$_2$NH—(CH$_2$)$_2$OH | Me | C |
| 224b | N | Et | (CH$_2$)$_2$NHMe | Me | A |
| 224c | N | CH$_2$F | (CH$_2$)$_2$NHMe | Me | C |

TABLE 1-2

| No. | X | R2 | R4 | R5 | Method of 3-side chain |
|---|---|---|---|---|---|
| 225c | N | CH₂F | (CH₂)₃NH₂ | Et | C |
| 226b | N | Et | (CH₂)₃NHMe | Et | C |
| 226c | N | CH₂F | (CH₂)₃NHMe | Et | C |
| 227c | N | CH₂F | (CH₂)₃NHMe | CF₃ | C |
| 231b | N | Et | H | OH | D |
| 232b | N | Et | H | NH₂ | C |
| 233b | N | Et | H | (CH₂)₃NH₂ | D |
| 234b | N | Et | Me | (CH₂)₃NH₂ | E |
| 234c | N | CH₂F | Me | (CH₂)₃NH₂ | E |
| 240b | N | Et | (CH₂)₂OH | H | A |
| 240c | N | CH₂F | (CH₂)₂OH | H | A |
| 241b | N | Et | CHF₂ | H | A |
| 241c | N | CH₂F | CHF₂ | H | A |
| 241g | N | H | CHF₂ | H | A |
| 242b | N | Et | CH₂CH=CH₂ | H | A |
| 242c | N | CH₂F | CH₂CH=CH₂ | H | A |
| 243b | N | Et | CH₂OMe | H | A |
| 244b | N | Et | (CH₂)₃Cl | H | A |

TABLE 1-3

| No. | X | R2 | R4 | R5 | Method of 3-side chain |
|---|---|---|---|---|---|
| 245b | N | Et | —(CH2)₃NH—◁ | H | E |
| 246b*¹ | N | Et | Me | H | C |
| 250b | N | Et | (azetidinyl-NH) | H | A |
| 250c | N | CH₂F | (azetidinyl-NH) | H | A |
| 251b | N | Et | (3R-pyrrolidinyl) | H | A |
| 252b | N | Et | (pyrrolidinyl-CH=NH) | H | E |
| 253b | N | Et | (pyrrolidinyl-C(Me)=NH) | H | E |
| 254b | N | Et | (N-Me-pyrrolidinyl) | H | E |
| 255c | N | CH₂F | -R4-R5- = —(CH₂)₃—N(Me)— | | F |

(*¹) R3 is p-Me for N⁺.

TABLE 2-1

| No. | ¹H-NMR (D₂O) δ: |
|---|---|
| 211b | 1.31(3H, d, J=7.2Hz), 1.45(3H, d, J=6.6Hz), 3.32 and 3.63(2H, ABq, J=18Hz), 4.07(1H, q like, J=6.6Hz), 4.36(2H, q, J=7.2Hz), 4.8(2H, m), 5.22(1H, d, J=4.5Hz), 5.63 and 5.93(2H, ABq, J=14.7Hz), 5.86(1H, d, J=4.5Hz), 7.93(1H, dd, J=6.6, 7.5Hz), 8.84(1H, d, J=7.5Hz) 8.88(1H, d, J=6.6Hz), 8.92(1H, s). |
| 211c | 1.44(3H, d, J=6.6Hz), 3.29 and 3.64(2H, ABq, J=18Hz), 4.06(1H, q like, J=6.6Hz), 4.36(2H, q, J=7.2Hz), 4.8(2H, m), 5.23(1H, d, J=4.8Hz), 5.63 and 5.92(2H, ABq, J=14.7Hz), 5.82(2H, J=54.3Hz), 5.86(1H, d, J=4.8Hz), 7.91(1H, dd, J=6.6, 8.4Hz), 8.83(1H, d, J=8.4Hz), 8.89(1H, d, J=6.6Hz), |
| 212c | [D6-DMSO]: 1.34(9H, br s), 2.07–2.16(2H, t-like), 2.79(3H, s), 2.96 and 3.55(2H, ABq, J=18Hz), 3.24(2H, t, J=6.9Hz), 4.46(2H, t, J=6.6Hz), 5.04(1H, d, J=5.1Hz), 5.63–5.70(3H, m), 5.71(2H, d, J=55.5Hz), 7.96(1H, t-like), 8.18(2H, s), 8.94(1H, d, J=8.1Hz), 9.13(1H, s), 9.65–9.70(2H, m). |
| 213b | 1.31(3H, d, J=7.2Hz), 1.51(6H, s), 3.33 and 3.63(2H, ABq, J=17.7Hz),, 4.33(2H, q, J=7.2Hz), 4.87–4.91(>1H, m), 5.22(1H, d, J=4.8Hz), 5.63 and 5.95(2H, ABq, J=14.7Hz), 5.86(1H, d, J=4.8Hz), 7.94(1H, dd, J=6.6, 8.4Hz), 8.84(1H, d, J=8.4Hz), 8.89(1H, d, J=6.6Hz), 8.91(1H, s). |
| 214b | 1.30(3H, d, J=6.9Hz), 2.79(3H, s), 3.31 and 3.63(2H, ABq, J=18Hz), 3.72(2H, t, J=6.3Hz), 4.33(2H, q, J=6.9Hz), 4.95(2H, t, J=6.3Hz), 5.22(1H, d, J=4.8Hz), 5.63 and 5.94(2H, ABq, J=14.7Hz), 5.85(1H, d, J=4.8Hz), 7.93(1H, dd, J=6.3, 8.4Hz), 8.85(1H, d, J=8.4Hz), 8.90(1H, d, J=6.3Hz), 8.94(1H, s). |
| 214c | 2.79(3H, s), 3.29 and 3.63(2H, ABq, J=18Hz), 3.71(2H, t, J=6.3Hz), 4.94(2H, t, J=6.3Hz), 5.23(1H, d, J=4.8Hz), 5.63 and 5.92(2H, ABq, J=14.7Hz), 5.82(2H, d, J=54.6Hz), 5.85(1H,d, J=4.8Hz), 7.9(1H, dd, J=6.3, 8.4Hz), 8.83(1H, d, J=8.4Hz), 8.90(1H, d, J=6.3Hz), 8.93(1H,s). |
| 215d | 2.38–2.48(2H, m), 3.23(2H, t, J=8Hz), 3.29 and 3.63(2H, ABq, J=18Hz), 3.41(2H, t, J=5 Hz), 4.28(2H, t, J=4.8Hz), 4.49–4.85(ca 6H, m), 5.23(1H, d, J=4.8Hz), 5.62 and 5.88(2H, ABq, J 15Hz),, 5.86(1H, d, J=4.8Hz), 7.89(1H, dd, J=6.3, 8.4Hz), 8.80(1H, d, J=8.4Hz), 8.86(1H, d, J=6 Hz), 8.87(1H, s). |

TABLE 2-1-continued

| No. | $^1$H-NMR (D$_2$O) δ: |
|---|---|
| 216d | 2.36–2.46(2H, m), 3.18–3.24(4H, m), 3.30 and 3.64(2H, ABq, J=18Hz), 3.82(2H, t, J=5.1Hz), 4.48–4.8 (ca 6H, m), 5.24(1H, d, J=4.8Hz), 5.63 and 5.89(2H, ABq, J=14.7Hz),, 5.86(1H, d, J=4.8Hz), 7.89(11 dd, J=6.3, 8.1Hz), 8.81(1H, d, J=8.1Hz), 8.84(1H, d, J=6.3Hz), 8.87(1H, s) s). |
| 216b | 1.30(3H, t, J=7.2Hz), 2.43–2.53(2H, m), 3.24–3.29(4H, m), 3.33 and 3.66(2H, ABq, J=18.3Hz), 3.88 (2H, t, J=5.1Hz), 4.29(2H, q, J=7.2Hz), 4.68(2H, t, J=7.2Hz), 5.26(1H, d, J=5.1Hz), 5.67 and 5.92 (2H, ABq, J=14.7Hz), ), 5.84(1H, d, J=5.1Hz), 7.00(1H, s). 792(1H, dd, J=6.6, 7.8Hz), 8.86(1H, d, J=7.8Hz), 8.89(1H, d, J=6.6Hz), 8.93(1H, s). |

TABLE 2-2

| No. | $^1$H-NMR(D$_2$O) δ: |
|---|---|
| 216g | 2.38–2.49(2H, m), 3.19–3.25(4H, m), 3.31 and 3.64(2H, ABq, J=18Hz), 3.84(2H, t, J=5.1Hz), 4.65 (2H, t, J=7.2Hz), 5.25(1H, d, J=4.8Hz), 5.69 and 5.93(2H, ABq, J=14.7Hz), ), 5.90(1H, d, J=4.8Hz), 7.88(1H, dd, J=6.3, 8.1Hz), 8.81(1H, d, J=8.1Hz), 8.85(1H, d, J=6.3Hz), 8.89(1H, s). |
| 220b | [D6-DMSO]: 1.18(3H, t, J=7.2Hz), 2.62(3H, s), 3.02 and 3.54(2H, ABq, J=18Hz), 4.10(2H, q, J=7.2 Hz), 5.10(1H, d, J=4.8Hz), 5.55(2H, br s), 5.76(1H, dd, J=4.8, 8.4Hz), 7.52(1H, dd, J=6.6, 7.8Hz), 8.10(2H, s), 8.39(1H, d, J=7.8Hz), 8.78(1H, br d, J=5.1Hz), 9.51(1H, d, J=8.4Hz), 12–14(1H, br). |
| 221b | 1.30(3H, t, J=6.9Hz), 2.23–2.33(2H, m), 2.84(3H, s), 3.15(2H, t, J=8.0Hz), 3.24 and 3.61(2H, ABq, J=18Hz), 4.33(2H, q, J=6.9Hz), 4.47–4.60(2H, m), 5.21(1H, d, J=5.1Hz), 5.55 and 5.77(2H, ABq, J=14.4Hz), 5.85(1H, d, J=5.1Hz), 7.77(1H, dd, J=6.2, 7.8Hz), 8.62(1H, d, J=8.1Hz), 8.68(1H, d, J=6.2 Hz). |
| 221c | 2.22–2.33(2H, m), 2.83(3H, s), 3.15(2H, t, J=8.0Hz), 3.26 and 3.63(2H, ABq, J=18Hz), 4.54(2H, t, J=7.5Hz), 5.25(1H, d, J=4.8Hz), 5.60 and 5.75(2H, ABq, J=15Hz), 5.82(2H, d, J=54.3Hz), 5.88 (1H, d, J=4.8Hz), 7.77(1H, dd, J=6.6, 8.4Hz), 8.61(1H, d, J=8.4Hz), 8.68(1H, d, J=6.6Hz). |
| 221d | 2.22–2.33(2H, m), 2.84(3H, s), 3.15(2H, t, J=8.0Hz), 3.26 and 3.62(2H, ABq, J=18Hz), 4.45–4.87(ca 6H, m), 5.24(1H, d, J=4.8Hz), 5.59 and 5.79(2H, ABq, J=14.7Hz), 5.87(1H, d, J=4.8Hz), 7.77(1H, dd, J=6.3, 8.4Hz), 8.63(1H, d, J=8.4Hz), 8.68(1H, d, J=6.3Hz). |
| 221a | 2.22–2.33(2H, m), 2.83(3H, s), 3.14(2H, t, J=8.0Hz), 3.26 and 3.62(2H, ABq, J=17.7Hz), 4.05(3H, s), 4.54(2H, t, J=7.2Hz), 5.23(1H, d, J=4.8Hz), 5.55 and 5.77(2H, ABq, J=15Hz), 5.85(1H, d, J= 4.8Hz), 7.77(1H, dd, J=6.6, 8.4Hz), 8.62(1H, d, J=8.4Hz), 8.68(1H, d, J=6.6Hz). |
| 222b | 1.30(3H, t, J=6.9Hz), 2.25–2.34(2H, m), 2.73(3H, s), 2.84(3H, s), 3.19(2H, t, J=8.1Hz), 3.26 and 3.61 (2H, ABq, J=18Hz), 4.33(2H, q, J=6.9Hz), 4.50–4.58(2H, m), 5.23(1H, d, J=4.8Hz), 5.55 and 5.78 (2H, ABq, J=15.0Hz), 5.85(1H, d, J=4.8Hz), 7.78(1H, dd, J=6.6, 8.1Hz), 8.62(1H, d, J=8.1Hz), 8.69 (1H, d, J=6.6Hz). |
| 222c | 2.25–2.35(2H, m), 2.73(3H, s), 2.83(3H, s), 3.18(2H, t, J=8.1Hz), 3.24 and 3.61(2H, ABq, J=18Hz), 4.54(2H, t, J=7.5Hz), 5.24(1H, d, J=4.8Hz), 5.55 and 5.77(2H, ABq, J=14.4Hz), 5.86(1H, d, J= 4.8Hz), 5.82(2H, d, J=54.3Hz), 7.77(1H, dd, J=6.3, 7.8Hz), 8.61(1H, d, J=7.8Hz), 8.69(1H, d, J= 6.3Hz). |
| 223c | 2.27–2.37(2H, m), 2.84(3H, s), 3.14–3.25(4H, m), 3.26 and 3.63(2H, ABq, J=17.7Hz), 3.82(2H, t, J 5.1Hz), 4.51–4.62(ca 2H, m), 5.24(1H, d, J=4.8Hz), 5.54 and 5.77(2H, ABq, J=14.7Hz), 5.82(1H, d, = 54.3Hz), 5.87(1H, d, J=4.8Hz), 7.77(1H, dd, J=6.3, 8.1Hz), 8.62(1H, d, J=8.1Hz), 8.69(1H, d, J 6.3Hz). |

TABLE 2-3

| No. | $^1$H-NMR(D$_2$O) δ: |
|---|---|
| 224b | 1.30(3H, t, J=7.2Hz), 2.79(3H, s), 2.87(3H, s), 3.27 and 3.61(2H, ABq, J=18Hz), 3.61(2H, t, J=6.6Hz), 4.33 (2H, q, J=7.2Hz), 4.64–4.87(2H, m), 5.22(1H, d, J=4.8Hz), 5.56 and 5.82(2H, ABq, J=15Hz), 5.85(1H, d, J=4.8Hz), 7.81(1H, dd, J=6.6, 8.1Hz), 8.66(1H, d, J=8.1Hz), 8.73(1H, d, J=6.6Hz) |
| 224c | 2.79(3H, s), 2.86(3H, s), 3.24 and 3.62(2H, ABq, J=18Hz), 3.61(2H, t, J=6.3Hz), 4.71–4.85(2H, m), 5.23 (1H, d, J=4.8Hz), 5.56 and 5.81(2H, ABq, J=14.4Hz), 5.82(2H, d, J=54.6Hz), 5.86(1H, d, J=4.8Hz), 7.80 (1H, dd, J=6.6, 8.1Hz), 8.65(1H, d, J=8.1Hz), 8.74(1H, d, J=6.6Hz) |
| 225c | 4.47(3H, t, J=7.2Hz), 2.22–2.32(2H m), 3.10–3.18(4H, m), 3.29 and 3.64(2H, ABq, J=18Hz), 4.52–4.61(2H, m), 5.24(1H, d, J=5.1Hz), 5.58 and 5.82(2H, ABq, J=14.7Hz), 5.82(2H, d, J=54.6Hz), 5.88 (1H, d, J=4.8Hz), 7.76(1H, dd, J=6.6, 8.1Hz), 8.61(1H, d, J=8.1Hz), 8.67(1H, d, J=6.6Hz). |
| 226b | 1.30(3H, t, J=7.2Hz), 1.47(3H, t, J=7.5Hz), 2.24–2.36(2H, m), 2.73(3H, s), 3.14(2H, q, J=7.5Hz), 3.18(2H, m), 3.35 and 3.64(2H, ABq, J=18Hz), 4.33(2H, q, J=7.2Hz), 4.55(2H, d, J=8.1Hz), 5.24 (1H, d, J=5.1Hz), 5.62 and 5.90(2H, ABq, J=14.7Hz), 5.88(1H, d, J=5.1Hz), 7.77(1H, dd, J=6.6, 8.4Hz), 8.63(1H, d, J=8.4Hz), 8.68(1H, d, J=6.6Hz). |
| 226c | 1.47(3H, t, J=7.5Hz), 2.25–2.32(2H, m), 2.73(3H, s), 3.11–3.22(4H, m), 3.30 and 3.63(2H, ABq, J= 18.3Hz), 4.54(2H, t, J=7.2Hz), 5.24(1H, d, J=5.1Hz), 5.58 and 5.86(2H, ABq, J=14.7Hz), 5.86(1H, d, J=5.1Hz), 5.82(2H, d, J=54.6Hz), 7.76(1H, dd, J=6.6, 8.1Hz), 8.61(1H, d, J=8.1Hz), 8.68(1H, d, J=6.6Hz). |
| 227c | [D6-DMSO]: 2.36(center, 2H, m), 2.57(3H, s), 3.13(center, 2H, m), 3.17 and 3.59(2H, ABq, J=18Hz), 4.81(center, 2H, m), 5.09(1H, d, J=4.8Hz), 5.51–5.78(3H, m), 5.71(2H, d, J=53.1Hz), 8.05(1H, d, J= 6.6Hz), 8.26(2H, br s), 9.33(1H, d, J=7.8Hz), 9.65–9.68(2H, m). |
| 231b | 1.20(3H, t, J=7.2Hz), 2.97 and 3.52(2H, ABq, J=18.3Hz), 4.12(2H, q, J=7.2Hz), 5.15(H, d, J= 4.8Hz), 5.18(2H, m), 5.81(1H, dd, J=4.8, 8.4Hz), 6.95(1H, t, J=7.2Hz), 7.26(1H, d, J=7.2Hz), 7.85 (1H, d, J=6.6Hz), 8.10(2H, br s), 9.57(1H, d, J=8.4Hz), 11.10(1H, s). |

TABLE 2-3-continued

| No. | $^1$H-NMR(D$_2$O) δ: |
|---|---|
| 232b | 1.20(3H, t, J=7.2Hz), 3.32 and 3.47(2H, ABq, J=18Hz), 4.13(2H, q, J=7.2Hz), 5.13(1H, d, J=5.1 Hz), 5.30 and 5.52(2H, ABq, J=15Hz), 5.87(1H, dd, J=5.1, 8.4Hz), 7.23(1H, t, J=7.5Hz), 7.80(1H, d, J=7.8Hz), 8.09(1H, d, J=6.6Hz), 8.14(2H, s), 8.34(2H, s), 9.56(1H, d, J=8.4Hz), 12.37(!H, br s). |
| 233b | 1.22(3H, t, J=7.2Hz), 2.19(center, 2H, m), 2.86(center, 2H, m), 3.16 and 3.30(2H, ABq, J=17Hz), 3.00–3.15(3H, m), 4.13(2H, q, J=7.2Hz), 5.00(1H, d, J=4.8Hz), 5.36(1H, J=13.2Hz), 5.83(1H, dd, J=4.8, 8.4Hz), 6.17(1H, br m), 7.65(1H, t, J=7.2Hz), 8.15(2H, s), 8.22(2H, br s), 8.54(1H, d, J= 8.4Hz), 8.77(1H, d, J=5.7Hz), 9.52(1H d, J=8.4Hz). |

TABLE 2-4

| No. | $^1$H-NMR(D6-DMSO) δ: |
|---|---|
| 234b | 1.22(3H, t, J=7.2Hz), 2.22(center, 2H, m), 2.85(center, 2H, m), 3.00 and 3.37(2H, ABq, J=17Hz), 3.00–3.16(3H, m), 3.92(3H, s), 4.15(2H, q, J=7.2Hz), 4.89(1H, d, J=5.1Hz), 5.24 and 6.63(2H, ABq, J=14Hz), 5.83(1H, dd, J=5.1, 8.4Hz), 7.83(1H, dd, J=6.3, 8.3Hz), 8.16(2H, s), 8.50(2H, br s), 8.32 (1H, d, J=8.3Hz), 8.98(1H, d, J=6.3Hz), 9.48(!H d, J=8.4Hz). |
| 234c | 2.21(center, 2H, m), 2.86(center, 1H, m), 3.08 and 3.37(2H, ABq, J=17Hz), 3.02–3.19(3H, m), 3.93 (3H, s), 4.94(1H, d, J=4.8Hz), 5.32 and 6.52(2H, ABq, J=14Hz), 5.76(2H, d, J=54Hz), 5.85(!H, m), 7.85(1H, dd, J=6, 8.1Hz), ), 8.25(2H, s), 8.45(2H, br s), 8.83(1H, d, J=8.1Hz), 8.98(1H, d, J=6 Hz), 9.71(1H, d, J=8.1Hz). |
| 240b | 1.16(3H, t, J=7.2Hz), 3.01 and 3.56(2H, ABq, J=17.7Hz), 3.80(2H, t, J=4.5Hz), 4.08(2H, q, J 7.2Hz), 4.55(2H, m), 5.02(1H, d, 5.1Hz), 5.61 and 5.70(2H, ABq, J=13.5Hz), 5.69(1H, dd, J=5.1, 8.4Hz 7.91(1H, dd, J=6.0, 8.1Hz), 8.15(2H, br s), 8.91(1H, d, J=8.1Hz), 9.05(1H, s), 9.45(1H, d, J=8.4Hz |
| 240c | 2.99 and 3.56(2H, ABq, J=17.4Hz), 3.82(2H, t, J=4.5Hz), 4.55(2H, t, J=4.5Hz), 5.04(1H, d, 5.1Hz, 5.67 (3H, m), 5.71(1H, d, J=55.2Hz), 7.94(1H, dd, J=6.0, 8.1Hz), 8.20(2H, br s), 8.91(1H, d, J=8.1Hz 9.05 (1H, s), 9.63(1H, d, J=6.0Hz), 9.68(1H, d, J=8.1Hz). |
| 241b | [D$_2$O Addition]: 1.16(3H, t, J=7.2Hz), 3.12 and 3.50(2H, ABq, J=17.1Hz), 4.10(2H, q, J=7.2Hz), 5.0 (1H, d, 4.8Hz), 5.64 and 5.76(2H, ABq, J=14.4Hz), 5.69(1H, d, J=4.8Hz), 8.02(1H, m), 8.10(1H, d,= 59.1Hz), 8.92(1H, d, J=7.8Hz), 9.34(1H, s), 9.50(1H, d, J=6.3Hz). |
| 241c | [D$_2$O Addition]: 3.11 and 3.51(2H, ABq, J=17.7Hz), 5.02(1H, d, J=4.8Hz), 5.63 and 5.75(2H, ABq, = 15Hz), 5.69(1H, d, J=4.8Hz), 5.71(2H, d, J=55.5Hz), 8.02(1H, dd, J=6.3, 7.2Hz), 8.09(1H, d, J=58.8Hz 8.92(1H, d, J=7.27Hz), 9.34(1H, s), 9.50(1H, d, J=6.3Hz). |
| 241g | [D$_2$O Addition]: 3.13 and 3.52(2H, ABq, J=18.3Hz), 5.03(1H, d, J=5.1Hz) 5.67 and 5.77(2H, ABq, J= 13.5Hz), 5.71(1H, d, J=5.1Hz), 8.06(1H, dd, J=6.1, 8.3 ヘルツ ), 8.16(1H, d, J=58.5Hz), 8.96(1H, d, J=8.3Hz), 9.40(1H, s), 9.60(1H, d, J=6.1Hz). |

TABLE 2-5

| No. | $^1$H-NMR(D6-DMSO) δ: |
|---|---|
| 242b | 1.18(3H, t, J=7.2Hz), 3.03 and 3.53(2H, ABq, J=17.7Hz), 4.11(2H, q, J=7.2Hz), 5.02(1H, d, 4.5Hz), 5.13 and 5.19(2H, ABq, J=14Hz), 5.29–5.31(1H, m), 5.35(1H, d, J=1.2Hz), 5.66–5.70(3H, m), 6.03–6.19(1H, m), 7.95(1H, dd, J=6.0, 8.4Hz), 8.11(2H, br s), 8.83(1H, d, J=7.8Hz), 9.09(1H, s), 9.44(1H, d, J=8.4Hz), 9.68(1H, d, J=6.0Hz). |
| 242c | 3.02 and 3.54(2H, ABq, J=17.4Hz), 5.04(1H, d, J=5.1Hz), 5.14 and 5.19(2H, ABq, J=14Hz), 5.30(1H, d, J=2.7Hz), 5.35(1H, s), 5.67(3H, m), 5.71(2H, d, J=55.8Hz), 6.00–6.20(1H, m), 7.95(1H, dd-like), 8.19(2H, br s), 8.83(1H, d, J=7.8Hz), 9.09(1H, s), 9.67(1H, d, J=8.1Hz), 9.68(1H, d, J=5.4Hz). |
| 243b | 1.18(3H, t, J=7.2Hz), 3.07 and 3.53(2H, ABq, J=17.7Hz), 3.32(3H, s), 4.10(2H, q, J=7.2Hz), 5.02 (1H, d, 5.1Hz), 5.64–5.71(3H, m), 5.85(2H, s), 8.00(1H, dd, J=6.3 8.1Hz), 8.11(2H, br s), 8.92(1H, d, J=8.1Hz), 9.25(1H, s), 9.45(1H, d, J=8.7Hz), 9.70(1H, d, J=6.3Hz). |
| 244b | 1.18(3H, t, J=7.2Hz), 2.33–2.42(2H, m), 3.00 and 3.52(2H, ABq, J=17.4Hz), 3.69(2H, t, J=6.6Hz), 4.07(2H, q, J=7.2Hz), 4.62(2H, t, J=7.2Hz), 5.02(1H, d, J=4.8Hz), 5.67–5.70(3H, m), 7.97(1H, dd, J=6.6, 8.1Hz), 8.12(2H, br s), 8.94(1H, d, J=8.1Hz), 9.12(1H, s), 9.45(1H, d, J=9.0Hz), 9.70(1H, d, J=6.6Hz). |
| 245b | 0.68(2H, d, J=6Hz), 0.88(2H, br s), 1.18(3H, t, J=7.2Hz), 2.31(center, 2H, m), 2.61(1H, m), 3.03 (2H, t, J=7.2Hz), 3.08 and 3.47(2H, ABq, J=16Hz), 4.10(2H, q, J=7.2Hz), 4.64(2H, t, J=7.2Hz), 5.04(1H, d, J=4.8Hz), 5.56 and 5.74(2H, ABq, J=14.4Hz), ), 5.75(1H, d, J=4.8Hz), 7.87(1H, dd, J=6.2, 8.1Hz), 8.12(2H, br s), 9.00(1H, d, J=8.4Hz), 9.16(1H, s), 9.26(1H, d, J=6.2Hz), 9.46(1H, d, J=8.1Hz). |
| 246b | 1.18(3H, t, J=7.2Hz), 2.92 and 3.50(2H, ABq, J=18Hz), 2.95(3H, s), 4.10(2H, q, J=7.2Hz), 4.21 (3H, s), 5.01(1H, d, J=4.8Hz), 5.58(2H, br s), 5.67(1H, dd, J=4.8, 8.7Hz), 7.71(1H, d, J=6.9Hz), 8.13(2H, br s), 8.91(1H, s), 9.45(1H, d, J=6.9Hz), 9.49(1H, d, J=8.7Hz). |

TABLE 2-6

| No. | $^1$H-NMR(D$_2$O) δ: |
|---|---|
| 250b | [D6-DMSO]: 1.18(3H, t, J=7.2Hz), 3.10 and 3.45(2H, ABq, J=17.7Hz), 4.11(2H, q, J=7.2Hz), 4.50–4.68(4H, m), 5.07(1H, d, J=4.8Hz), 5.63(1H, J=13.5Hz), 5.75(1H, dd, J=4.8, 8.4Hz), 5.85–5.89 (2H, m), 8.01(1H, dd, J=6.3, 8.1Hz), 8.15(2H, s), 9.19(1H, d, J=8.1Hz), 9.41(1H, d, J=6.3Hz), 9.49 (1H, d, J=8.4Hz), 9.56(1H, s). |
| 250c | 3.09 and 3.46(2H, ABq, J=18Hz), 4.50–4.63(4H, m), 5.04(1H, d, J=5.1Hz), 5.66(2H, d, J=53Hz), 5.62–5.87(4H, m), 7.95(1H, t-like), 8.18(2H, s), 9.12(1H, d, J=8.1Hz), 9.30(1H, d, J=9Hz), 9.51(1H, s), 9.68(1H, d, J=8.1Hz), |
| 251b | [D6-DMSO]: 1.17(3H, t, J=6.6Hz), 2.69(center, 2H, m), 3.15 and 3.47(2H, ABq, J=18Hz), 3.47–3.81 (4H, m), 4.10(2H, q, J=6.6Hz), 5.04(1H, d, J=5.1Hz), 5.31 and 5.88(2H, ABq, J=13.5Hz), 5.60(1H, m), 5.80(1H, dd, J=5.1, 8.4Hz), 7.94(1H, dd, J=7.2, 7.5Hz), 8.12(2H, s), 9.03–9.05(2H, m), c9.50(1H, d, J=8.4Hz), |
| 252b | [65/35 mixture] 1.30(3H, t, J=7.2Hz), 2.67–2.98(2H, m), 3.31 and 3.62(2H, ABq, J=18Hz), 3.83–3.90 (1H, m), 4.00–4.17(1H, m), 4.26–4.38(2H, m), 4.33(2H, q, J=7.2Hz), 5.22(1H, d, J=4.8Hz), 5.61 and 5.93(2H, ABq, J=14.4Hz), 5.85(1H, d, J=4.8Hz), 7.91(1H, dd, J=6.3, 8.1Hz), 8.13 and 8.15(ca0.65H and 0.35H, each s), 8.84(1H, d, J=8.1Hz), 8.87(1H, d, J=6.3Hz), 8.90 and 8.95(ca 0.65H and 0.35H, each s). |
| 253b | [55/45 mixture] 1.30(3H, t, J=7.2Hz), 2.36 and 2.40(1.65H and 1.35H, each s), 2.67–2.98(2H, m), 3.35 and 3.66(2H, ABq, J=18Hz), 3.82–3.89(1H, m), 3.99–4.08(1H, m), 4.21–4.51(2H, m), 4.32(2H, q, J= 7.2Hz), 5.25(1H, d, J=4.8Hz), 5.62–5.74(1H, m), 5.72 and 5.99(2H, ABq, J=14.7Hz), 5.87(1H, d, J= 4.8Hz), 7.92(1H, dd, J=6.3, 8.1Hz), 8.86(1H, d, J=8.1Hz), 8.92(1H, d, J=6.3Hz), 8.93 and 8.95 (ca0.55H and 0.45H, each s). |
| 254b | 1.30(3H, t, J=7.2Hz), 2.74–2.84(1H, m), 3.01(center, 1H, m), 3.11(3H, s), 3.31 and 3.63(2H, ABq, J= 17.7Hz), 3.35–4.25(4H, m), 4.33(2H, q, J=7.2Hz), 5.22(1H, d, J=4.8Hz), 5.61 and 5.94(2H, ABq, J= 14.7Hz), 5.76(center, 1H, m), 5.85(1H, d, J=4.8Hz), 7.92(1H, dd, J=6.3, 8.1Hz), 8.82(1H, d, J= 8.1Hz), 8.88(1H, d, J=6.3Hz), 9.05(1H, s). |
| 255c | [D6-DMSO]: 2.20(2H, br s), 3.15 and 3.45(2H, ABq, J=17.7Hz), 3.28(3H, s), 3.56(2H, br s), 4.10(2H, br s), 5.05(1H, d, J=4.8Hz), 5.32 and 5.33(2H, ABq, J=14.4Hz), 5.74(2H, d, J=55.2Hz), 5.73(1H, dd, J=4.8, 8.1Hz), 7.21(1H, t, J=6.9Hz), 7.90(1H, d, J=7.5Hz), 8.22(2H, br s), , 8.61(1H, d, J=6Hz), 9.71 (1H, d, J=8.1Hz). |

TABLE 3-1

| No. | IR(KBr) cm$^{-1}$ (Data in "[ ]" is of 4-ester of quaternary ammonium salt ???) |
|---|---|
| 211b | 3406, 2979, 1772, 1614, 1527, 1389, 1117, 1037, 619. |
| | [CHCl$_3$: 3260, 3220, 1773, br1704, 1633, 1611, 1240, 1151, 1037.] |
| 211c | 3388, 1772, 1672, 1612, 1527, 1396, 1117, 619. |
| | [CHCl$_3$: br 3218, 1771, br1713, 1634, 1611, 1243, 1154.] |
| 212c | 3405, 2975, 1780, 1675, 1616,, 1529, 1487, 1461, 1394, 1153, 1062, 991, 862, 760 |
| 213b | 3405, 1774, 1672, 1631, 1525, 1385, 1117, 1037, 611. |
| | [Nujol: 3213, 1788, br1713, 1633, 1612, 1248, 1157, 1038, .] |
| 214b | 3398, 1772, 1668, 1610, 1527, 1389, 1234, 1117, 1038, 619. |
| | [Nujol: 3210, 1788, 1716, 1686, 1635, 1612, 1247, 1174, 1155, 1038.] |
| 214c | 3425, 1772, 1672, 1612, 1525, 1394, 1120, 1081, 619. |
| | [Nujol: 3210, 1788, 1716, 1686, 1635, 1612, 1247, 1174, 1155, 1038.] |
| 215d | 3409, 1774, 1671, 1633, 1527, 1389, 1230, 1151, 1063, 1018, 759, 625, 581. |
| 216d | 3394, 1772, 1672, 1635, 1612, 1527, 1390, 1120, 1065, 619. |
| | [CHCl$_3$: 3401, 3223, br1774, 1718, 1684, 1635, 1612, 1247, 1174, 1155, 1062.] |
| 216b | 3374, 1776, 1664, br 1635, 1535, 1464, 1385, 1115, 1034, 758, 619. |
| | [CHCl$_3$: 3406, 1792, 1722, 1681, 1635, 1612, 1228, 1155, 1037.] |
| 216g | 3384, 1772, 1670, br 1612, 1527, 1464, 1389, 1066, 1018, 760. |
| 220b | 3423, 1756, 1666, 1647, 1603, 1539, 1458, 1396, 1038, 762. |
| 221b | 3408, 1770, 1668, 1616, 1525, 1463, 1398, 1119, 1037, 619. |
| | [Nujol: 3267, 3221, 1772, 1714, 1686, 1637, 1612, 1250, 1159, 1109, 1037.] |

TABLE 3-2

| No. | IR(KBr) cm$^{-1}$ |
|---|---|
| 221c | Nujol: 3278, 3116, 3045, 1772, 1714, 1685, 1641, 1277, 1234, 1090. |
| | (Nujol: 3267, 3217, 1770, 1712, 1691, 1637, 1614, 1250, 1174, 1157, 1120, 1005.] |
| 221d | 3408, 3174, 3030, 1778, 1674, 1635, 1525, 1463, 1400, 1113, 1065, 619. |
| 221a | 3409, 3035, 1772, 1670, 1616, 1463, 1398, 1118, 1039, 619. |
| | [CHCl$_3$: 3406, 3213, 1770, 1713, 1637, 1612, 1247, 1174, 1155, 1039.] |
| 222b | 3413, 1774, 1672, 1635, 1525, 1464, 1398, 1117, 1039, 619. |
| 222c | 3406, 1774, 1674, 1616, 1527, 1463, 1398, 1119, 1083, 619. |
| 223c | 3406, 1774, 1673, 1614, 1527, 1463, 1400, 1117, 1082, 619. |
| | [Nujol: 3400, 3214, 1789, 1714, 1682, 1614, 1250, 1155, 860.] |
| 224b | Nujol: 3309, 1763, br1680, 1610, 1039. |
| | [Nujol: 3434, 3219, 1784, 1716, 1686, 1637, 1612, 1585, 1248, 1157, 1038.] |
| 224c | Nujol: 3310, 1768, 1672, 1603, 1057. |
| | [Nujol: 3433, 3201, 1768, 1732, 1712, 1689, 1639, 1614, 1248, 1155, 1120, 1001.] |

TABLE 3-2-continued

| No. | IR(KBr) cm$^{-1}$ |
|---|---|
| 225c | 3400, 1774, 1676, 1616, , 1527, 1466, 1400, 1113, 1072, 617. |
| 226b | 3406, 3184, 2983, 1782, 1674, 1637, 1525, 1467, 1221, 1153, 1110, 1039, 617, 588. [Nujol: 3430, 3271, 3213, 1770, 1714, 1684, 1639, 1614, 1248, 1157, 1035,.] |
| 226c | 3409, 3030, 2810, 1776, 1676, 1635, 1616, , 1527, 1465, 1402, 1119, 1080, 619 [Nujol: 3428, 3265, 3201, 1767, 1730, 1711, 1689, 1639, 1614, 1248, 1155, 1120, 1057.] |

TABLE 3-3

| No. | IR(KBr) cm$^{-1}$ |
|---|---|
| 227c | 3401, 1770, 1674, 1523, 1475, 1265, 1203, 1132, 721. |
| 231b | 3412, 1771, 1655, 1625, 1522, 1399, 1358, 1298, 1153, 1038, 758. |
| 232b | 3340, 3190, 1776, 1661, 1567, 1524, 1490, 1402, 1311, 1217, 1162, 1035, 760. |
| 233b | 3398, 3171, 3023, 1772, 1670, br1613, 1526, 1461, 1401, 1356, 1037, 760. |
| 234b | 3398, 3034, 1767, 1670, 1614, 1525, 1475, 1394, 1356, 1319, 1148, 1037, 758. |
| 234c | 3398, 3023, 1774, 1676, 1616, 1523, 1475, 1396, 1321, 1139, 1078, 1060, 991, 758. |
| 240b | 3399, 1774, 1670, br 1613, 1527, 1386, 1292, 1234, 1038, 759. |
| 240c | 3422, 1773, 1672, br 1614, 1525, 1389, 1292, 1235, 1069, 991, 760. |
| 241b | 3396, 1774, 1669, 1611, 1528, 1458, 1411, 1320, 1083, 1038, 823. |
| 241c | 3414, 1774, 1674, 1613, 1527, 1459, 1413, 1321, 1227, 1081, 823. |
| 241g | 3414, 1773, 1670, 1612, 1525, 1459, 1413, 1394, 1321, 1242 1078, 823. |
| 242b | 3400, 1775, 1670 br 1613, 1528, 1383, 1290, 1234, 1038, 783. |

TABLE 3-4

| No. | IR (KBr) cm$^{-1}$ |
|---|---|
| 242c | 3386, 1776, 1674, br 1612, 1528, 1382, 1290, 1234, 1076, 784, 760, |
| 243b | 3400, 1776, 1671, br 1614, 1527, 1389, 1296, 1231, 1104, 1038, 757. |
| 244b | 3396, 1774, 1672, br 1614, 1527, 1462, 1387, 1234, 1037, 760. |
| 245b | 3398, 1774, 1670, 1635, 1612, 1527, 1387, 1236, 1065, 756. |
| 246b | 3398, 1764, 1680, br 1616, 1533, 1391, 1358, 1239, 1152, 1038, 631. |
| 250b | 3399, 1770, 1669, br 1611, 1525, 1484, 1390, 1353, 1146, 1037, 759. |
| 250c | 3410, 1772, 1674, 1612, 1525, 1462, 1394, 1352, 1138, 1063, 987, 760. |
| 251b | 3412, 1777, 1677, 1636, 1528, 1463, 1406, 1202, 1132, 1039, 800, 722. |
| 252b | 3392, 1772, 1707, br 1670, 1606, 1525, 1462, 1389, 1348, 1036, 758. |
| 253b | 3383, 1772, 1672, br 1630, 1462, 1389, 1360, 1038, 758. |
| 254b | 3415, 1770, 1668, br 1610, 1527, 1462, 1392, 1354, 1038, 760. |
| 255c | 3400, 1770, 1654, 1616, 1595, 1524, 1417, 1321, 1144, 1084, 758. |

TABLE 4-1

| No. | Elementary Anallysis | Calculated value (%) | | | | | | Measured value (%) | | | | | |
|---|---|---|---|---|---|---|---|---|---|---|---|---|---|
| | | C | H | N | S | F | Cl | C | H | N | S | F | Cl |
| 211b | C23H26N10O5S2 0.5 H2SO4.6 H2O | 37.14 | 5.29 | 18.83 | 10.78 | | | 37.06 | 5.10 | 18.69 | 10.79 | | |
| 211c | C22H23N10O5S2F 0.5H2SO4.5.5 H2O | 35.77 | 4.78 | 18.96 | 10.85 | 2.57 | | 35.63 | 4.66 | 18.97 | 11.08 | 2.45 | |
| 212c | C28H33N10O79S2F 0.5H2SO4.8 H2O | 44.32 | 5.18 | 18.46 | 8.45 | 2.50 | | 44.42 | 5.13 | 18.57 | 8.30 | 2.35 | |
| 213b | C24H28N10O5S21.0H2SO4.4.5 H2O | 36.97 | 5.04 | 17.96 | 12.34 | | | 36.84 | 4.85 | 18.10 | 12.51 | | |
| 214b | C23H26N10O5S2.0.5H2SO4.4 H2O | 39.03 | 4.98 | 19.79 | 11.33 | | | 38.95 | 4.79 | 19.68 | 11.14 | | |
| 214c | C22H23N10O5S2F.0.5H2SO4.5H2O | 36.21 | 4.70 | 19.19 | 10.99 | 2.60 | | 36.17 | 4.42 | 19.28 | 10.72 | 2.76 | |
| 215d | C25H29N10O9S3F.0.3 H2SO4.5 H2O | 35.40 | 4.71 | 16.51 | 12.48 | 2.24 | | 35.60 | 4.71 | 16.48 | 12.36 | 2.37 | |
| 216d | C25H29N10O6S2F.0.7 H2SO4.2 H2O. 0.33 iPrOH | 40.41 | 4.83 | 18.12 | 11.20 | 2.46 | | 40.36 | 4.70 | 18.05 | 11.47 | 2.50 | |
| 216b | C26H31N9O6S2.0.85 H2SO4. 2.5 H2O | 41.19 | 5.01 | 16.63 | 12.05 | | | 41.33 | 4.91 | 16.75 | 11.97 | | |
| 216g | C23H26N10O6S2.1.8 HCl.4.2 H2O | 37.13 | 4.90 | 18.83 | 8.62 | | 8.58 | 37.00 | 4.93 | 19.11 | 8.59 | | 8.52 |
| 220b | C21H21N9O5S2.4 H2O | 40.97 | 4.75 | 20.48 | 10.42 | | | 41.09 | 4.77 | 20.62 | 10.62 | | |
| 221b | C24H28H10O5S2.0.5 H2SO4. 5.5 H2O | 38.50 | 5.38 | 18.71 | 10.71 | | | 38.29 | 5.18 | 18.78 | 10.77 | | |
| 221c | C23H25N10O5S2F 1.0 H2SO4.8 H2O | 32.62 | 5.12 | 16.54 | 11.36 | 2.24 | | 32.72 | 4.93 | 16.58 | 11.51 | 2.22 | |
| 221d | C24H27N10O5S2F 0.8 H2SO4.2 H2O | 39.33 | 4.46 | 19.11 | 12.25 | 2.59 | | 39.33 | 4.33 | 18.96 | 12.42 | 2.48 | |
| 221a | C23H26N10O5S2 0.5 H2SO4.4.2 H2O.0.2 iPrOH | 39.24 | 5.02 | 19.39 | | 11.10 | | 39.23 | 5.03 | 19.21 | | 11.38 | |

*FAB$^+$-Mass 215d 9221: [M + 1]$^+$729, 216d 9197: [M + 1]$^+$649

TABLE 4-2

| No. | Elementary Anallysis | Calculated value (%) | | | | | | Measured value (%) | | | | | |
|---|---|---|---|---|---|---|---|---|---|---|---|---|---|
| | | C | H | N | S | F | Cl | C | H | N | S | F | Cl |
| 222b | C25H30N10O5S2 0.68 H2SO4.5.5 H2O | 38.47 | 5.47 | 17.95 | 11.01 | | | 38.25 | 5.08 | 18.21 | 11.01 | | |
| 222c | C24H27N10O5S2F.0.5 H2SO4.0.8 H2O | 38.22 | 5.03 | 18.57 | 10.63 | 2.52 | | 38.27 | 4.80 | 18.73 | 10.54 | 2.56 | |
| 223c | C25H29N10O6S2F. 0.7 H2SO4.7 H2O | 35.60 | 5.31 | 16.61 | 10.27 | 2.25 | | 35.59 | 5.17 | 16.79 | 10.22 | 2.54 | |
| 224b | C24H28N10O5S2. 0.5 H2SO4.5.8 H2O | 38.22 | 5.43 | 18.57 | 10.63 | | | 37.93 | 5.19 | 18.90 | 10.72 | | |
| 224c | C23H25N10O5S2F.0.65 H2SO4.6.4 H2O | 39.54 | 4.47 | 20.05 | 11.47 | 2.72 | | 39.62 | 4.45 | 20.25 | 11.29 | 2.68 | |
| 225c | C24H27N10O5S2F.0.65 H2SO4.6.4 H2O | 36.14 | 5.19 | 17.56 | 10.65 | 2.38 | | 36.09 | 5.11 | 17.75 | 10.70 | 2.24 | |
| 226b | C26H32N10O5S2 1.4 H2SO4.6 H2O | 35.73 | 5.40 | 16.02 | 12.47 | | | 35.43 | 5.11 | 16.11 | 12.55 | | |
| 226c | C25H29N10O5S2F 0.8 H2SO4.5.6 H2O | 36.98 | 5.19 | 17.25 | 11.06 | 2.34 | | 36.97 | 4.87 | 17.33 | 10.76 | 2.40 | |
| 227c | C24H24N10O5S2F4.0.8 CF3CO2H.0.8 HCl.4.5 H2O | 35.18 | 3.99 | 16.02 | 7.34 | 13.91 | 3.24 | 35.22 | 3.64 | 15.83 | 7.34 | 14.07 | 3.33 |
| 231b | C20H19N9O6S2..3.1 H2O | 40.06 | 4.20 | 21.02 | 10.70 | | | 39.85 | 4.29 | 20.99 | 10.66 | | |
| 232b | C20H20N10O5S2.1.3 HCl.3 H2O | 37.18 | 4.26 | 21.68 | | 9.93 | 7.13 | 37.46 | 4.37 | 21.30 | | 9.62 | 6.85 |
| 233b | C23H26N10O5S2.1.3 HCl.4.4 H2O | 38.73 | 5.10 | 19.64 | 8.99 | | 6.46 | 38.96 | 5.05 | 19.65 | 8.69 | | 6.40 |
| 234b | C24H28N10O5S2.1.3 HCl.5.5 H2O | 38.58 | 5.44 | 18.75 | 8.58 | | 6.17 | 38.84 | 5.51 | 18.97 | 8.35 | | 6.28 |
| 234c | C23H25N10O5S2F.1.5 HCl.4.8 H2O | 37.04 | 4.88 | 18.78 | 8.60 | 2.55 | 7.13 | 37.31 | 4.93 | 18.79 | 8.43 | 2.16 | 7.02 |
| 240b | C22H23N9O6S2.3 H2O | 42.10 | 4.66 | 20.08 | 10.22 | | | 41.89 | 4.61 | 20.20 | 10.26 | | |
| 240c | C21H20N9O6S2F.3.3 H2O | 39.60 | 4.21 | 19.79 | 10.07 | 2.98 | 39.59 | 4.20 | 20.14 | 10.17 | 2.82 | | |
| 241b | C21H19N9O5S2F2.2.6 H2O | 40.21 | 3.89 | 20.12 | 10.24 | 6.07 | 40.34 | 4.05 | 20.18 | 10.12 | 5.89 | | |
| 241c | C20H16N9O5S2F3.2.2 H2O | 38.55 | 3.30 | 20.22 | 10.29 | 9.15 | | 38.51 | 3.53 | 20.50 | 9.98 | 9.34 | |

*LSIMS 231b 9991: [M + 1]+546

TABLE 4-3

| No. | Elementary Anallysis | Calculated value (%) | | | | | | Measured value (%) | | | | | |
|---|---|---|---|---|---|---|---|---|---|---|---|---|---|
| | | C | H | N | S | F | Cl | C | H | N | S | F | Cl |
| 241g | C19H15N9O5S2F2.3 H2O | 37.69 | 3.50 | 20.82 | 10.59 | 6.27 | | 37.89 | 3.73 | 20.00 | 10.79 | 6.29 | |
| 242b | C23H23N9O5S2.3 H2O | 44.29 | 4.69 | 20.21 | 10.28 | | | 44.23 | 4.74 | 20.34 | 10.01 | | |
| 242c | C22H20N9O5S2F.1.5 H2O | 44.00 | 3.86 | 20.99 | 10.68 | 3.16 | | 44.25 | 4.14 | 20.96 | 10.64 | 2.82 | |
| 243b | C22H23N9O6S2.3.2 H2O | 41.86 | 4.69 | 19.97 | 10.16 | | | 41.78 | 4.59 | 20.14 | 10.06 | | |
| 244b | C23H24N9O5S2Cl.4.6 H2O | 40.74 | 4.76 | 18.59 | 9.46 | | 5.23 | 40.90 | 4.85 | 18.34 | 9.33 | | 5.06 |
| 245b | C26H30N10O5S2.1.2 HCl.5 H2O | 41.06 | 5.46 | 18.42 | 8.43 | | 5.59 | 41.11 | 5.47 | 18.47 | 8.28 | | 5.79 |
| 246b | C22H23N9O5S2.4.6 H2O | 41.26 | 5.07 | 19.68 | 10.01 | | | 41.44 | 5.11 | 19.80 | 9.74 | | |
| 250b | C23H24N10O5S2.1.25 HCl.4.5 H2O | 38.84 | 4.85 | 19.69 | 9.02 | | 6.23 | 39.08 | 4.77 | 19.84 | 8.67 | | 6.15 |
| 250c | 22H21N10O5S2F.1.07 HCl.5 H2O | 36.82 | 4.50 | 19.52 | 8.94 | 2.65 | 5.29 | 36.82 | 4.36 | 19.52 | 8.66 | 2.60 | 5.00 |
| 251b | C24H26N10O5S2.1.55 HCl.5.5 H2O | 35.33 | 4.02 | 14.11 | 6.46 | 14.93 | | 35.38 | 3.81 | 14.08 | 6.45 | 14.77 | |
| 252b | C25H27N11O5S2.2.6 CF3CO2H.5.5 H2O | 39.54 | 5.07 | 20.29 | 8.44 | | 5.60 | 39.70 | 5.05 | 20.17 | 8.05 | | 5.67 |
| 253b | C26H29N11O5S2.1.23 HCl.5.5 H2O | 39.85 | 5.30 | 19.66 | 8.18 | | 5.57 | 39.74 | 5.29 | 19.80 | 8.09 | | 5.44 |
| 254b | C25H28N10O5S2.1.3 HCl.5.5 H2O | 39.55 | 5.35 | 18.45 | 8.45 | | 6.07 | 39.61 | 5.25 | 18.43 | 8.22 | | 6.10 |
| 255c | C23H23N10O5S2.1.3 HCl.5.5 H2O | 38.62 | 4.62 | 19.58 | 9.41 | 2.66 | 2.97 | 38.73 | 4.38 | 19.17 | 9.17 | 2.38 | 2.92 |

*LSIMS 252b 9156: [M + 1]+626, FAB+-Mass 255c 204–9211: [M + 1]+603, [M + Na]+625.

EXPERIMENTAL

The minimal inhibitory concentration (MIC) of compound (I) against various bacteria was determined by an agar dilution method. The result is shown in Table 5. As reference compounds, used were cefozopran hydrochloride (CZOP) described in JP(A) Kokai H03-47189, cefoselis sulfate (CFSL) described in JP(A) Kokai H07-196665 and WO97/41128, compound A of which 3-side chain is a type of imidazo[4,5-c]pyridiniummethyl, and vancomycin. In the table, "Ex5-3", for example, represents the end compound of the present invention obtained in Example 5-3, and the others are similarly expressed.

TABLE 5

| MIC (ug/ml) | | Ex 5-3 | Ex 6-2 | Ex 6-3 | Ex 4-1 | Ex 5-2 | CZOP | CFSL | A | VCM |
|---|---|---|---|---|---|---|---|---|---|---|
| G(+) | S. aureus SMITH | 0.78 | 1.56 | 0.78 | 0.78 | 0.78 | 0.78 | 0.78 | 0.78 | 0.78 |
| | S. aureus SR14 | 0.78 | 1.56 | 0.78 | 1.56 | 0.78 | 0.78 | 0.78 | 3.13 | 0.78 |
| | S. aureus SR3626 | 3.13 | 3.13 | 6.25 | 3.13 | 3.13 | 50 | 25 | 25 | 3.13 |
| | S. aureus SR3637 | 3.13 | 3.13 | 6.25 | 6.25 | 3.13 | 50 | 25 | 25 | 3.13 |
| | S. pneumoniae Type1 | 0.025 | 0.025 | 0.025 | 0.025 | 0.025 | 0.05 | 0.013 | 0.0125 | 0.39 |
| | S. pneumoniae SR16675 | 0.78 | 0.78 | 0.78 | 0.39 | 0.78 | 0.78 | 0.39 | 0.39 | 0.2 |
| | S. mitis SR16376 | 0.2 | 0.1 | 0.2 | 0.1 | 0.2 | 0.2 | NT | 0.1 | 0.39 |
| | E. faecalis SR1004 | 100 | 50 | 50 | 50 | 50 | 25 | >100 | 50 | |

TABLE 5-continued

| | | | | | | | | | |
|---|---|---|---|---|---|---|---|---|---|
| G(−) | E. coli NIH JC-2 | 0.1 | 0.39 | 0.2 | 0.2 | 0.39 | 0.05 | 0.05 | 0.05 |
| | E. coli SR5028 | 1.56 | 3.13 | 1.56 | 3.13 | 3.13 | 0.78 | 0.78 | 1.56 |
| | P. vulgaris CN-329 | 0.39 | 0.78 | 0.39 | 0.78 | 0.78 | 0.2 | 0.025 | 0.1 |
| | E. cloacae ATCC 13047 | 0.39 | 0.78 | 0.78 | 0.78 | 0.78 | 0.2 | 0.2 | 0.48 |
| | E. cloacae SR4321 | 12.5 | 25 | 12.5 | 25 | 25 | 6.25 | 12.5 | 12.5 |
| | S. marcescens ATCC 13880 | 0.1 | 0.39 | 0.2 | 0.2 | 0.39 | 0.1 | 0.1 | 0.1 |
| | P. aeruginosa SR24 | 1.56 | 1.56 | 3.13 | 0.78 | 0.78 | 0.78 | 3.13 | 0.78 |
| | P. aeruginosae SR5393 | 6.25 | 6.25 | 6.25 | 3.13 | 3.13 | 1.56 | 6.25 | 3.13 |
| | $ED_{50}$ (mg/kg) mouse/S. aureus SR3637 | 5.66 | 7.92 | 6.43 | 11.3 | | | 37.1 | 5.66 |

(Reference)

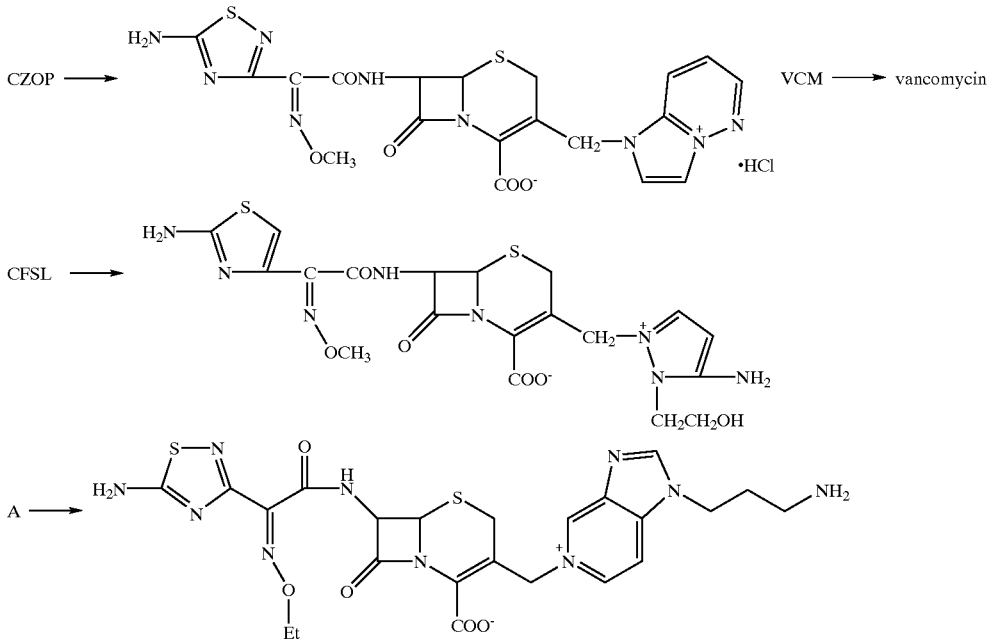

The result shows that the present compound (I) possesses potent antibacterial activities against various bacteria including MRSA (e.g., S.aureus SR3626 and S.aureus SR3637).

Preparation 1

Compound 37c obtained in Example 6-3(2) is lyophilized to give an injection.

Preparation 2

Powder of compound 108c obtained in Example 29(2) is filled to give an injection.

INDUSTRIAL APPLICABILITY

The compounds of the present invention are useful as antibacterial agents. The present invention further provides intermediates thereof.

What is claimed is:
1. A compound of formula(I):

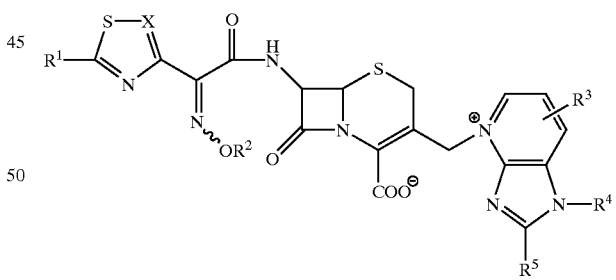

wherein,
X is N;
$R^1$ is amino;
$R^2$ is lower alkyl optionally substituted with halogen;
$R^3$ is hydrogen;
$R^4$ is lower alkyl optionally substituted with amino, lower alkylamino, amino(lower)alkylamino, and/or hydroxy;
$R^5$ is hydrogen; and
a wavy line means syn- or anti-isomerism or a mixture thereof, an ester, a pharmaceutically acceptable salt or a solvate thereof.
2. The compound described in claim 1, a pharmaceutically acceptable salt or hydrate thereof wherein $R^2$ is —$CH_2F$; $R^4$ is —$(CH_2)_3NHCH_3$; and the wavy line means syn-isomerism.

3. The compound described in claim 2 which is a sulfate or a hydrate thereof.

4. A method for preparing the compound described in claim 1, which comprises optionally protecting amino and hydroxy functional moieties and reacting a compound of formula(V):

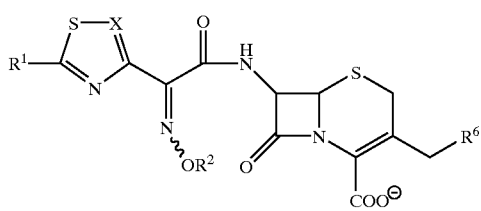

(V)

wherein $R^6$ is a leaving group and the other symbols are the same as defined in claim 1, an ester, or a salt thereof with a compound of formula(IV):

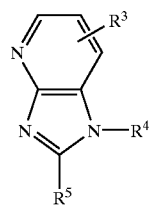

(IV)

wherein each symbol is the same as defined in claim 1, followed by optional deprotection.

5. A pharmaceutical composition which contains the compound described in claim 1 and a pharmaceutically acceptable carrier.

6. A method for preventing or treating bacterial infectious diseases, which comprises administering the compound described in claim 1.

7. A compound, pharmaceutically acceptable salt or hydrate thereof according to claim 1, wherein $R^2$ is lower alkyl; $R^4$ is lower alkyl optionally substituted with amino or lower alkylamino; and a wavy line means syn-isomerism.

8. A compound, pharmaceutically acceptable salt or hydrate thereof according to claim 1, wherein $R^2$ is —$CH_2CH_3$; $R^4$ is —$(CH_2)_3NH_2$, —$(CH_2)_3NHCH_3$, or —$CH_2CH(NH_2)CH_3$; and a wavy line means syn-isomerism.

9. A compound, pharmaceutically acceptable salt or hydrate thereof according to claim 1, wherein $R^2$ is —$CH_2CH_3$; $R^4$ is —$(CH_2)_3NHCH_3$; and a wavy line means syn-isomerism.

* * * * *